(12) United States Patent
Aronhime et al.

(10) Patent No.: US 7,435,827 B2
(45) Date of Patent: Oct. 14, 2008

(54) ZOLEDRONIC ACID CRYSTAL FORMS, ZOLEDRONATE SODIUM SALT CRYSTAL FORMS, AMORPHOUS ZOLEDRONATE SODIUM SALT, AND PROCESSES FOR THEIR PREPARATION

(75) Inventors: Judith Aronhime, Rehovot (IL); Revital Lifshitz-Liron, Herzlia (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 0 days.

(21) Appl. No.: 11/527,254

(22) Filed: Sep. 25, 2006

(65) Prior Publication Data

US 2007/0027323 A1 Feb. 1, 2007

Related U.S. Application Data

(62) Division of application No. 10/886,099, filed on Jul. 6, 2004, now abandoned.

(60) Provisional application No. 60/484,876, filed on Jul. 3, 2003.

(51) Int. Cl.
*C07F 9/6506* (2006.01)
(52) U.S. Cl. .................................................. 548/112
(58) Field of Classification Search .................. 548/112
See application file for complete search history.

(56) References Cited

U.S. PATENT DOCUMENTS

| | | | |
|---|---|---|---|
| 4,594,466 | A | 6/1986 | Reeves |
| 4,777,163 | A | 10/1988 | Bosies et al. |
| 4,939,130 | A | 7/1990 | Jaeggi et al. |
| 7,138,524 | B2 | 11/2006 | McCarty et al. |
| 7,250,527 | B2 | 7/2007 | Godbole et al. |
| 2004/0077683 | A1 | 4/2004 | Reddy et al. |

FOREIGN PATENT DOCUMENTS

WO    WO 03/093282    11/2003

OTHER PUBLICATIONS

Polymorphism in Pharmaceutical Solids (1999).*
US Pharmacopia #23, National Formulary #18 (1995).*
Drugs of the Future 2000, 25(3); 259-268.*
Bernstein, Polymorphism in Molecular Crystals, pp. 117-118 and 272 (2002).*
Rhaoi, "The Right Stuff", Chemical And Engineering News, p. 32-35, 2003.
Brittain et al., "Effects of pharmaceutical processing on drug polymorphs and solvates," Polymorphism in Pharmaceutical Solids (1999).
Byrn et al., "Solid-State Chemistry of Drugs" (1999) pp. 62-63.
Cattaneo, John S., Experiment with Acid Mine Water and Living History- A Coal Mine History (Jul. 2000).
de Dios, Angel C., "Le Chatelier's Principle- Chemical equilibrium" Lecture VIII, http://bouman.chem.georgetown.edu/S02/lect8/lect8. htm, retrieved Apr. 2006.
Gray, Analytical Chemistry Lecture Online: Complexation and Precipitation Titrations, http://sbuniv.edu/~ggray/CHE3345/chp15. html, retrieved Apr. 2006.
Hayes, Process Principles in Minerals and Material Production, (1993).
Kegley et al., Water Treatment: How Can We Make Our Water Safe to Drink?, http://chemistry.beloit.edu/Water/, retrieved Mar. 2005.
Koga, N. et al., "An Experimental Approach to the Precipitation Reaction of Basic Zinc Carbonate," The Chemical Educator, http:// chemeducator.org/sbibs/s0010006/spapers/106044nk.htm, retrieved Apr. 2006.
Li et al., "Improved process for the synthesis of zoledronic acid as a new drug for treating hyperlipidemia," Chinese J. New Drugs (2002) 12: 164-168.
Protein Purification Handbook, Amersham Biosciences, 2001.
Volumetric (Titrimetric) Analysis, retrieved (Apr. 2006).
Yan et al., Chinese J. Med. Chem. (2002) vol. 12(3)-5 pgs.
Zhu et al., "Synthesis of zoledronic acid," Chinese J. New drugs (2003) 12: 39-40.
http://www.expresspharmaonline.com/20031023/edit02.shtml.
International Search Report of Application PCT/US04/021626, dated May 10, 2005.

* cited by examiner

*Primary Examiner*—Rebecca L Anderson
*Assistant Examiner*—Yong Chu
(74) *Attorney, Agent, or Firm*—Kenyon & Kenyon LLP

(57) ABSTRACT

The invention relates to polymorphs of zoledronic acid and zoledronate sodium salts, amorphous zoledronate sodium salt, processes for making the polymorphs and amorphous zoledronate sodium salt, and pharmaceutical compositions containing the polymorphs and amorphous zoledronate sodium salt.

2 Claims, 44 Drawing Sheets

FIG. 24 TGA CURVE OF ZOLEDRONIC ACID FORM I

FIG.25 TGA CURVE OF ZOLEDRONIC ACID FORM II

FIG. 26 TGA CURVE OF ZOLEDRONIC ACID FORM XII

TGA CURVE OF ZOLEDRONIC ACID FORM XV

FIG.29 TGA CURVE OF ZOLEDRONIC ACID FORM XX

FIG. 30 TGA CURVE OF ZOLEDRONIC ACID FORM XXVI

FIG.31 TGA CURVE OF ZOLEDRONATE MONOSODIUM FORM VIII

TGA CURVE OF ZOLEDRONATE MONOSODIUM FORM XVI

FIG. 34 TGA CURVE OF ZOLEDRONATE DISODIUM FORM V

TGA CURVE OF ZOLEDRONATE DISODIUM FORM VI

FIG.36 TGA CURVE OF ZOLEDRONATE DISODIUM FORM VII

FIG.37 TGA CURVE OF ZOLEDRONATE DISODIUM FORM X

TGA CURVE OF ZOLEDRONATE DISODIUM FORM XIX

FIG. 41 TGA CURVE OF ZOLEDRONATE DISODIUM FORM XXV

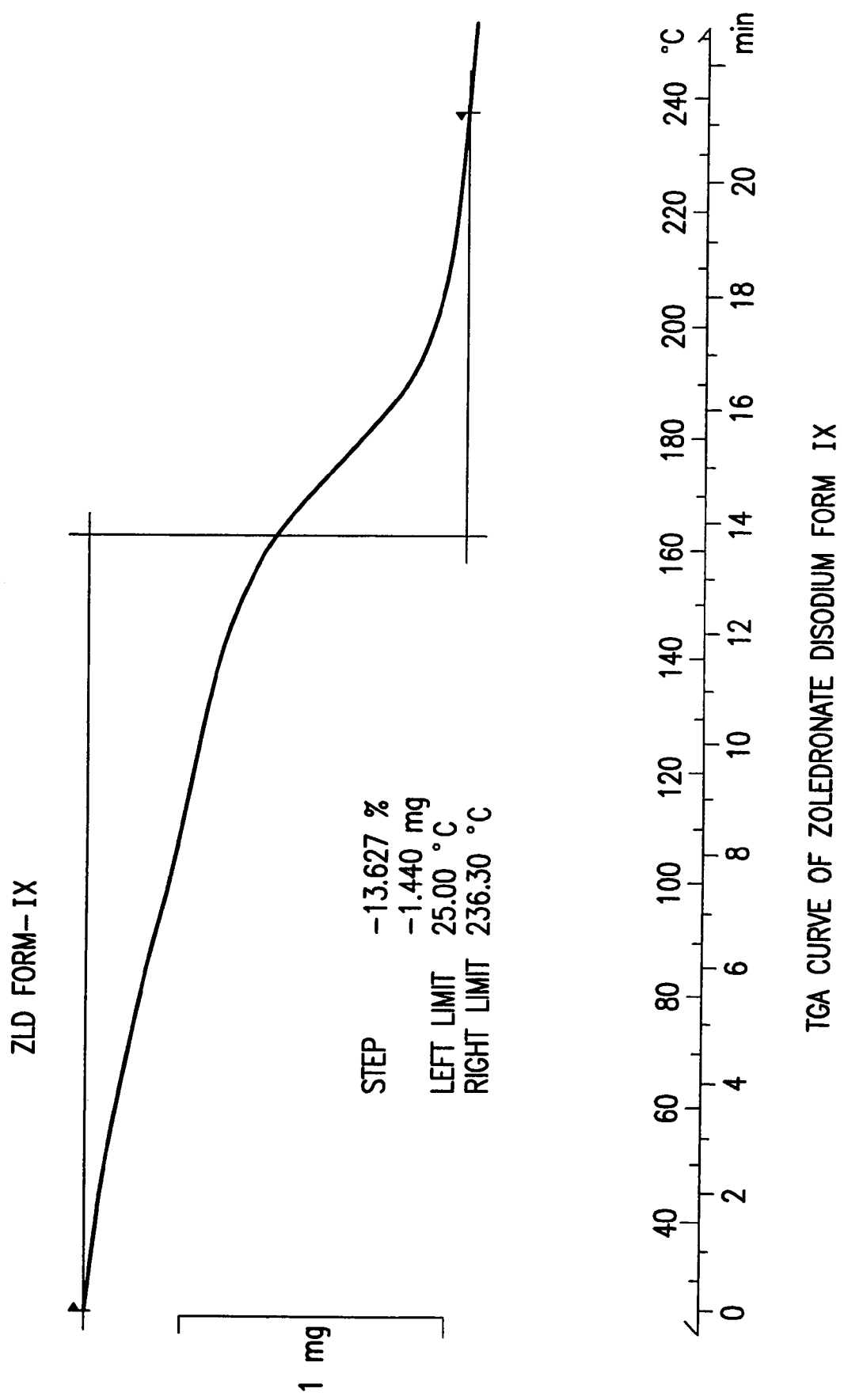
FIG. 43 TGA CURVE OF ZOLEDRONATE DISODIUM FORM IX

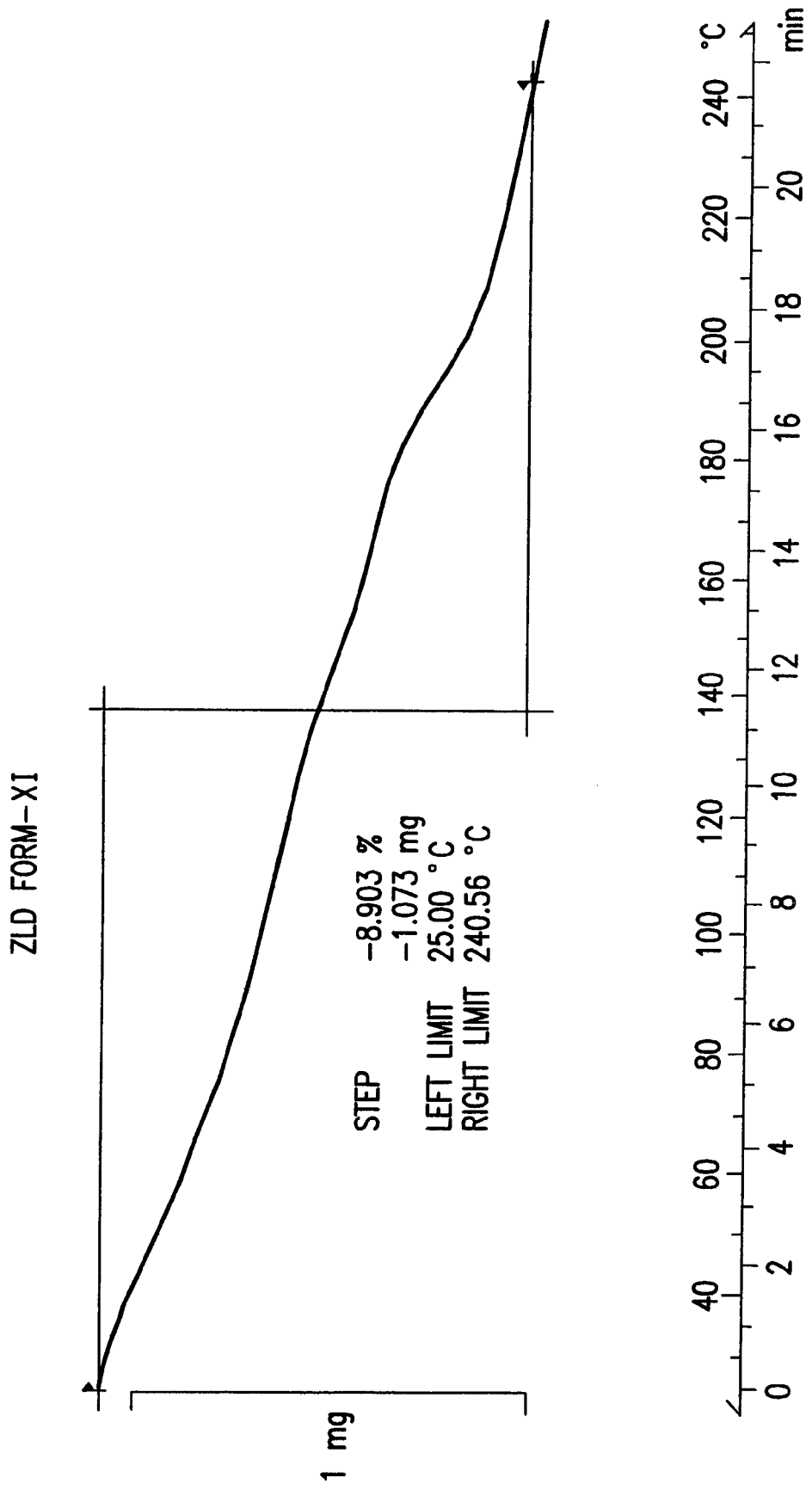
FIG.44 TGA CURVE OF ZOLEDRONATE DISODIUM FORM XI

ZOLEDRONIC ACID CRYSTAL FORMS, ZOLEDRONATE SODIUM SALT CRYSTAL FORMS, AMORPHOUS ZOLEDRONATE SODIUM SALT, AND PROCESSES FOR THEIR PREPARATION

CROSS REFERENCE TO RELATED APPLICATIONS

This application is a division of U.S. patent application Ser. No. 10/886,099, filed Jul. 6, 2004, now abandoned, which claims the benefit of U.S. provisional application Ser. No. 60/484,876, filed Jul. 3, 2003, the contents of all of which is incorporated herein.

FIELD OF THE INVENTION

The invention relates to polymorphs of zoledronic acid and zoledronate sodium salts, amorphous zoledronate sodium salt, processes for making the polymorphs and amorphous zoledronate sodium salt and pharmaceutical compositions containing the polymorphs and amorphous zoledronate sodium salt.

BACKGROUND OF THE INVENTION

Zoledronic acid is a bisphosphonic acid, which is an inhibitor of osteoclastic bone resorption. Zoledronic acid, designated chemically as (1-Hydroxy-2-imidazol-1-yl-phosphonoethyl) phosphonic acid is marketed in the U.S. under the name Zometa® (zoledronic acid for injection). Zometa® is available in vials as a sterile powder for reconstitution for intravenous infusion. The prescribing information for Zometa® states that each vial of Zometa® contains 4.264 mg of zoledronic acid monohydrate (corresponding to 4 mg zoledronic acid on an anhydrous basis).

U.S. Pat. No. 4,939,130 discloses a method for making substituted alkanediphosphonic acids. Example 10 describes a method for making zoledronic acid. In this example, at the end of the reaction, the product, which is recrystallized from water, has a melting point of 239° C. with decomposition. However, repetition of the procedure described in Example 10 (which requires stirring under reflux imidazol-1-ylacetic acid hydrochloride and phosphoric acid in chlorobenzene) did not lead to zoledronic acid; instead, the starting material was collected at the end of the reaction. Moreover, the last step of crystallization could not be repeated exactly since the detailed experimental parameters are not given (different cooling regimes, for instance, can produce different polymorphs when crystallized in the same solvent).

In the paper *Drugs of the future* 2000, 25(3): 259-268 the following forms of Zoledronate are listed:
1) Zoledronic acid disodium salt tetrahydrate CAS No. 165800-07-7
2) Zoledronic acid magnesium salt CAS No. 157432-59-2
3) Zoledronic acid zinc salt CAS No. 157432-58-1
4) Zoledronic acid disodium salt anhydrous CAS No. 131654-46-1
5) Zoledronic acid anhydrous CAS No. 118072-93-8
6) Zoledronic acid monohydrate CAS No. 165800-06-6

It is also disclosed in the paper that the free acid has a melting point of 239° C. with decomposition, and the disodium salt dihydrate has a melting point of 291-293° C. with decomposition. However, the paper does not describe any procedure to obtain the forms mentioned therein, nor does it give any additional data by which they can be identified.

Moreover, there is nothing in the literature that discloses polymorphs or different crystal forms of zoledronic acid.

The solid state physical properties of a compound can be influenced by controlling the conditions under which the compounds are obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are determined by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others. A particular polymorphic form may also give rise to distinct spectroscopic properties that may be detectable by powder X-ray diffraction (PXRD), solid state $^{13}C$ NMR spectrometry and infrared spectrometry.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. The invention provides for new polymorphic forms of zoledronic acid and zoledronate sodium, and for amorphous zoledronate sodium.

BRIEF DESCRIPTION OF THE FIGURES

FIG. 43 is a representative TGA curve of zoledronate disodium Form IX.

FIG. 44 is a representative TGA curve of zoledronate disodium Form XI.

SUMMARY OF THE INVENTION

Figure 1:
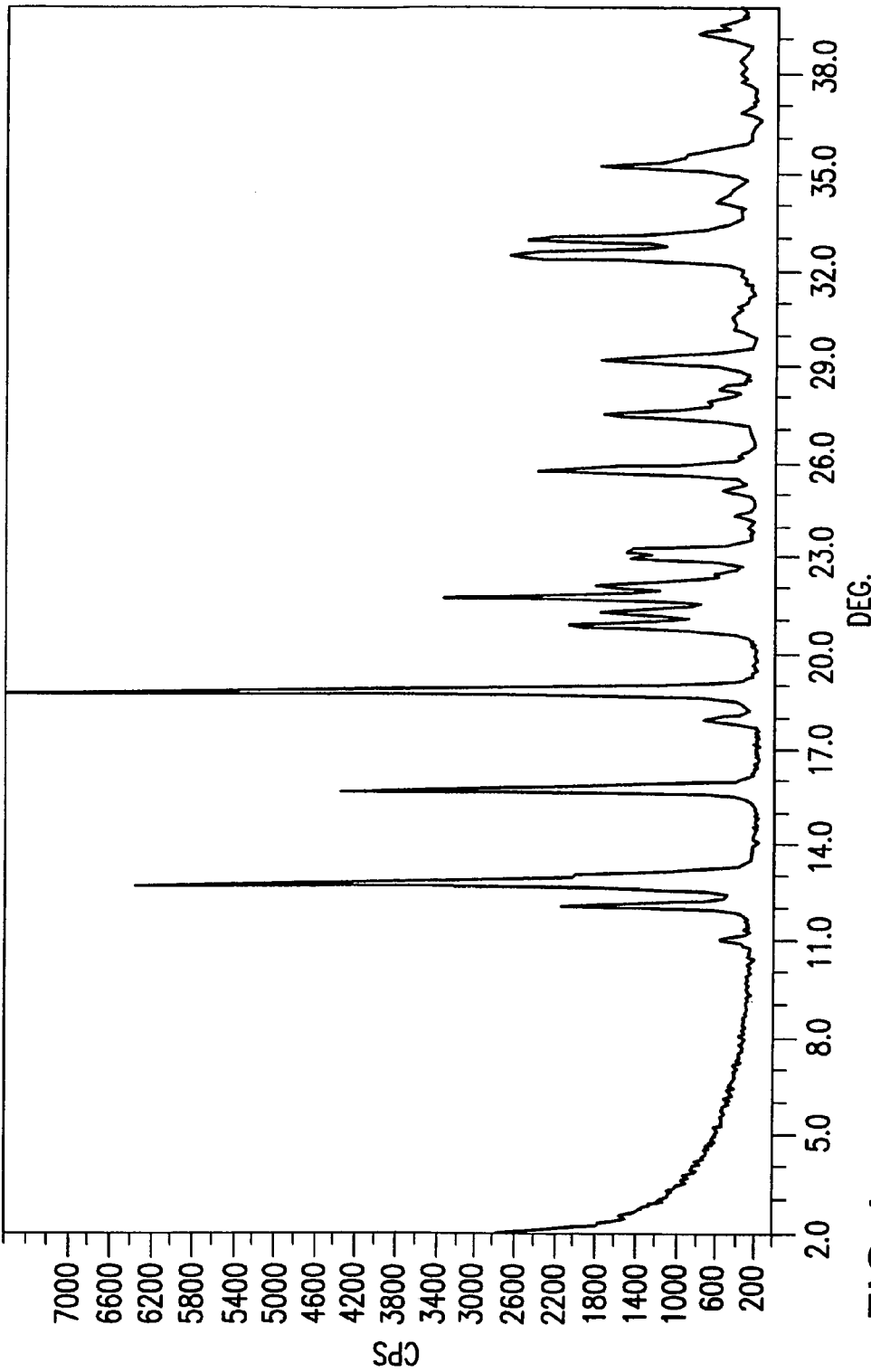
FIG. 1 is a representative PXRD pattern of zoledronic acid Form I.

The invention relates to polymorphs of zoledronic acid and zoledronate sodium salts, amorphous zoledronate sodium salt, processes for making the polymorphs and amorphous zoledronate sodium salt and pharmaceutical compositions containing the polymorphs and amorphous zoledronate sodium salt. The invention can be understood by reference to the following numbered embodiments.

1. Crystalline solid zoledronic acid (Form I) characterized by a powder X-ray diffraction pattern having peaks at 12.1°, 12.8°, 15.7°, and 18.9° 2θ±0.2° 2θ.

2. The crystalline solid zoledronic acid of embodiment 1, further characterized by a powder XRD pattern with peaks at 20.9°, 21.3°, 21.8°, 22.2°, 25.8°, 27.6°, 29.2°, 32.5°, and 32.9° 2θ±0.2° 2θ.

3. The crystalline solid zoledronic acid of embodiment 1, which contains less than about 5% of other polymorphic forms of zoledronic acid.

4. The crystalline solid zoledronic acid of embodiment 1, of which no more than about 5% transforms to zoledronic acid Form II upon exposure to 100% relative humidity (RH) for 7 days.

5. The crystalline solid zoledronic acid of embodiment 4, of which no more than about 5% transforms to other polymorphic forms of zoledronic acid upon exposure to 100% relative humidity (RH) for 7 days.

6. The crystalline solid zoledronic acid of embodiment 1, which, upon exposure to 100% relative humidity (RH) for 7 days, absorbs less than about 0.2% water.

7. The crystalline solid zoledronic acid of embodiment 1, which, upon exposure to 100% relative humidity (RH) for 7 days, retains its X-ray diffraction pattern substantially as shown in figure no. 1.

8. The crystalline solid zoledronic acid of embodiment 1, of which no more than about 5% transforms to zoledronic acid form II upon exposure to 75% relative humidity (RH) at 40° C. for 3 months.

9. The crystalline solid zoledronic acid of embodiment 8, of which no more than about 5% transforms to other polymorphic forms of zoledronic acid upon exposure to 75% relative humidity (RH) at 40° C. for 3 months.

10. The crystalline solid zoledronic acid of embodiment 1, which, upon exposure to 75% relative humidity (RH) at 40° C. for 3 months, absorbs less than about 0.2% water.

11. The crystalline solid zoledronic acid of embodiment 1, which, upon exposure to 75% relative humidity (RH) at 40° C. for 3 months, retains its X-ray diffraction pattern substantially as shown in figure no. 1.

12. A pharmaceutical composition comprising the crystalline zoledronic acid of any of embodiments 1 to 11.

13. The crystalline solid zoledronic acid of embodiment 1, which is a monohydrate.

14. Crystalline solid zoledronic acid (Form II) characterized by a powder X-ray diffraction pattern having peaks at 14.6°, 15.4°, 19.1°, 22.9°, and 23.9° 2θ±0.2° 2θ.

15. The crystalline zoledronic acid of embodiment 14, further characterized by a powder X-ray diffraction pattern with peaks at 20.8°, 21.7°, 25.1°, 26.7°, 29.5°, and 29.9° 2θ±0.2° 2θ.

16. The crystalline solid zoledronic acid of embodiment 14, which is a monohydrate.

17. Crystalline solid zoledronic acid (Form XII) characterized by a powder X-ray pattern having peaks at 9.0°, 13.9°, 14.8°, 21.5°, 24.7°, and 29.8° 2θ±0.2° 2θ.

18. The crystalline zoledronic acid of embodiment 17, further characterized by a powder X-ray diffraction pattern with peaks at 17.0°, 20.6°, 20.8°, 22.4°, 25.8°, 27.7°, 28.4°, 28.7°, 29.1°, 30.8°, 31.9°, 32.3°, and 32.9° 2θ±0.2° 2θ.

19. The crystalline solid zoledronic acid of embodiment 17, which is a monohydrate.

20. Crystalline solid zoledronic acid (Form XV) characterized by a powder X-ray diffraction pattern having peaks at 10.1°, 17.3°, 19.3°, and 23.2° 2θ±0.2° 2θ.

21. The crystalline zoledronic acid of embodiment 2, further characterized by a powder X-ray diffraction pattern with peaks at 14.5°, 16.7°, 18.1°, 24.5°, 25.1°, 25.7°, 28.5°, 29.1°, 29.6°, and 30.4° 2θ±0.2° 2θ.

22. The crystalline solid zoledronic acid of embodiment 20, which is anhydrous.

23. Crystalline solid zoledronic acid (Form XVIII) characterized by a powder X-ray diffraction pattern having peaks at 10.7°, 13.0°, 16.4°, 17.4°, and 28.5° 2θ±0.2° 2θ.

24. The crystalline zoledronic acid of embodiment 23, further characterized by a powder X-ray diffraction pattern with peaks at 13.3°, 18.1°, 19.3°, 21.3°, 23.7°, 25.9°, 31.5°, and 34.5° 2θ±0.2° 2θ.

25. The crystalline solid zoledronic acid of embodiment 23, which is a monohydrate.

26. Crystalline solid zoledronic acid (Form XX) characterized by a powder X-ray diffraction pattern having peaks at 12.2°, 19.3°, 20.2°, 21.3°, 25.1°, and 27.25° 2θ±0.2° 2θ.

27. The crystalline zoledronic acid of embodiment 26, further characterized by a powder X-ray diffraction pattern with peaks at 11.4°, 14.9°, 15.5°, 17.2°, 18.2°, and 30.5° 2θ±0.2° 2θ.

28. The crystalline solid zoledronic acid of embodiment 26, which is anhydrous.

29. Crystalline solid zoledronic acid (Form XXVI) characterized by a powder X-ray diffraction pattern having peaks at 9.8°, 14.5°, 17.1°, 17.6°, and 18.3° 2θ±0.2° 2θ.

30. The crystalline zoledronic acid of embodiment 29, further characterized by a powder X-ray diffraction pattern with peaks at 18.8°, 19.7°, 21.4°, 25.7°, 26.6°, and 28.1° 2θ±0.2° 2θ.

31. The crystalline solid zoledronic acid of embodiment 29, which is anhydrous.

32. A pharmaceutical composition comprising the crystalline solid zoledronic acid of any of embodiments 12 to 31.

33. Crystalline solid zoledronate monosodium.

34. Crystalline solid zoledronate monosodium hydrate.

35. The crystalline solid zoledronate monosodium of embodiment 33, characterized by a powder X-ray diffraction pattern having peaks at 8.2°, 15.5°, 18.6°, 23.6°, and 26.8° 2θ±0.2° 2θ (Form VIII).

36. The crystalline solid zoledronate monosodium of embodiment 35, further characterized by a powder X-ray diffraction pattern with peaks at 11.8°, 17.6°, 20.1°, 24.7°, 25.0°, 28.4°, 31.7°, and 32.8° 2θ±0.2° 2θ.

37. The crystalline solid zoledronate monosodium of embodiment 35, which is a trihydrate.

38. The crystalline solid zoledronate monosodium of embodiment 33, characterized by a powder X-ray diffraction pattern having peaks at 7.3°, 8.8°, 14.7°, 21.8°, and 29.6° 2θ±0.2° 2θ (form XVI).

39. The crystalline solid zoledronate monosodium of embodiment 38, further characterized by a powder X-ray diffraction pattern with peaks at 13.8°, 16.8°, 20.4°, 21.4°, 24.4°, 25.6°, 27.5°, 28.2°, and 31.7° 2θ±0.2° 2θ.

40. The crystalline solid zoledronate monosodium of embodiment 38, which is a dihydrate.

41. The crystalline solid zoledronate monosodium of embodiment 33, characterized by a powder X-ray diffraction pattern having peaks at 8.2°, 9.0°, 14.5°, 21.4°, 24.5°, and 29.2° 2θ±0.2° 2θ (Form XVII).

42. The crystalline solid zoledronate monosodium of embodiment 41, further characterized by a powder X-ray diffraction pattern with peaks at 13.9°, 15.5°, 16.8°, 18.6°, 22.3°, 23.6°, 26.7°, 27.7°, and 32.3° 2θ±0.2° 2θ.

43. The crystalline solid zoledronate monosodium of embodiment 41, which is a dihydrate.

44. Crystalline solid zoledronate disodium.

45. Crystalline solid zoledronate disodium hydrate.

46. Crystalline solid zoledronate disodium anhydrous.

47. The crystalline solid zoledronate disodium of embodiment 44, characterized by a powder X-ray diffraction pattern having at 11.3°, 14.8°, 15.5°, 17.4°, and 19.9° 2θ±0.2° 2θ (Form V).

48. The crystalline solid zoledronate disodium of embodiment 47, further characterized by a powder X-ray diffraction pattern with peaks at 18.0°, 18.9°, 19.7°, 22.7°, 25.0°, 26.7°, 30.9°, and 34.5° 2θ±0.2° 2θ.

49. The crystalline solid zoledronate disodium of embodiment 47, which is a dihydrate.

50. The crystalline solid zoledronate disodium of embodiment 44, characterized by a powder X-ray diffraction pattern having peaks at 7.2°, 13.3°, 13.7°, 14.5°, and 21.7° 2θ±0.2° 2θ (Form VI).

51. The crystalline solid zoledronate disodium of embodiment 50, further characterized by a powder X-ray diffraction pattern with peaks at 8.2°, 16.6°, 16.9°, 17.3°, 25.9°, 26.6°, 30.7°, 31.9°, and 32.9° 2θ±0.2° 2θ.

52. The crystalline solid zoledronate disodium of embodiment 50, which is a trihydrate.

53. The crystalline solid zoledronate disodium of embodiment 44, characterized by a powder X-ray diffraction pattern having peaks at 6.2°, 11.6°, 12.6°, and 13.7 2θ°±0.2° 2θ (Form VII).

54. The crystalline solid zoledronate disodium of embodiment 53, further characterized by a powder X-ray diffraction pattern with peaks at 22.0°, 23.2°, 26.4°, 27.1°, 28.6°, 28.8°, and 34.2° 2θ±0.2° 2θ.

55. The crystalline solid zoledronate disodium of embodiment 53, which is a tetrahydrate.

56. The crystalline solid zoledronate disodium of embodiment 44, characterized by a powder X-ray diffraction pattern having peaks at 6.7°, 14.4°, 18.2°, 20.4°, and 20.7° 2θ±0.2° 2θ (Form X).

57. The crystalline solid zoledronate disodium of embodiment 56, further characterized by a powder X-ray diffraction pattern with peaks at 8.8°, 13.7°, 17.0°, 19.8°, 21.3°, 24.4°, 27.5°, 27.9°, 30.9°, and 33.4° 2θ±0.2° 2θ.

58. The crystalline solid zoledronate disodium of embodiment 56, which is a hemihydrate.

59. The crystalline solid zoledronate disodium of embodiment 44, characterized by a powder X-ray diffraction pattern having peaks at 6.5°, 13.0°, 16.1°, 17.2°, and 30.7° 2θ±0.2° 2θ (Form XIII).

60. The crystalline solid zoledronate disodium of embodiment 59, further characterized by a powder X-ray diffraction pattern with peaks at 10.2°, 19.0°, 20.0°, 20.6°, 22.3°, 27.4°, 28.6°, 28.9°, and 34.8° 2θ±0.2° 2θ.

61. The crystalline solid zoledronate disodium of embodiment 59, which is a hemihydrate.

62. The crystalline solid zoledronate disodium of embodiment 44, characterized by a powder X-ray diffraction pattern having peaks at 6.6°, 19.9°, 28.5°, and 34.8° 2θ±0.2° 2θ (Form XIV).

63. The crystalline solid zoledronate disodium of embodiment 62, further characterized by a powder X-ray diffraction pattern with peaks at 13.0°, 15.1°, 17.1°, 20.5°, 27.7°, 29.6°, 30.7°, and 33.5° 2θ±0.2° 2θ.

64. The crystalline solid zoledronate disodium of embodiment 62, which is anhydrous.

65. The crystalline solid zoledronate disodium of embodiment 44, characterized by a powder X-ray diffraction pattern having peaks at 11.6°, 12.5°, 13.7°, 22.0°, and 23.1° 2θ±0.2° 2θ (Form XIX).

66. The crystalline solid zoledronate disodium of embodiment 65, further characterized by a powder X-ray diffraction pattern with peaks at 6.2°, 14.3°, 15.3°, 16.0°, 18.5°, 24.3°, and 28.6° 2θ±0.2° 2θ.

67. The crystalline solid zoledronate disodium of embodiment 65, which is a pentahydrate.

68. The crystalline solid zoledronate disodium of embodiment 44, characterized by a powder X-ray diffraction pattern having peaks at 7.4°, 13.7°, 17.6°, and 21.9° 2θ±0.2° 2θ (Form XXV).

69. The crystalline solid zoledronate disodium of embodiment 68, further characterized by a powder X-ray diffraction pattern with peaks at 6.3°, 9.5°, 12.6°, 14.6°, 26.2°, 27.1°, and 28.6° 2θ±0.2° 2θ.

70. The crystalline solid zoledronate disodium of embodiment 68, which is a sesquihydrate.

71. The crystalline solid zoledronate disodium of embodiment 44, which is a monohydrate characterized by a powder X-ray diffraction pattern having peaks at 6.4°, 8.2°, 16.0°, 17.4°, 19.0°, and 28.8° 2θ±0.2° 2θ (Form XXVII).

72. The crystalline solid zoledronate disodium of embodiment 71, further characterized by a powder X-ray diffraction pattern with peaks at 7.7°, 10.2°, 17.2°, 18.1°, 21.6°, 25.7°, and 25.9° 2θ±0.2° 2θ.

73. The crystalline solid zoledronate disodium of embodiment 71, which is a monohydrate.

74. Crystalline solid zoledronate trisodium.

75. The crystalline solid zoledronate trisodium of embodiment 74, characterized by a powder X-ray diffraction pattern having peaks at 8.3°, 10.9°, 15.0°, 16.6°, and 22.8° 2θ±0.2° 2θ (Form IX).

76. The crystalline solid zoledronate trisodium of embodiment 75, further characterized by a powder X-ray diffraction pattern with peaks at 13.1°, 20.2°, 20.6°, 20.9°, 25.0°, 27.8°, and 29.0° 2θ±0.2° 2θ.

77. The crystalline solid zoledronate trisodium of embodiment 75, which is a trihydrate.

78. The crystalline solid zoledronate trisodium of embodiment 74, characterized by a powder X-ray diffraction pattern having peaks at 6.2°, 7.9°, 8.8°, 10.6°, and 12.2° 2θ±0.2° 2θ (Form XI).

79. The crystalline solid zoledronate trisodium of embodiment 78, further characterized by a powder X-ray diffraction pattern with peaks at 15.0°, 15.4°, 17.5°, 18.8°, 19.6°, 20.5°, 22.3°, 23.7°, 25.7°, 29.6°, and 31.7° 2θ±0.2° 2θ.

80. The crystalline solid zoledronate trisodium of embodiment 78, which is a dihydrate.

81. A process for preparing a solid crystalline zoledronate sodium salt comprising:
a) dissolving zoledronic acid in water to form a solution;
b) adding a base, preferably sodium hydroxide, to the solution; and
c) cooling the solution, optionally with the addition of an organic solvent such as isopropyl alcohol, to precipitate crystalline zoledronate sodium.

82. The process of embodiment 81, wherein the crystalline solid zoledronate sodium salt is the monosodium salt.

83. The process of embodiment 82, wherein the crystalline solid zoledronate monosodium is selected from the group consisting of Form VIII, Form XVI and Form XVII.

84. The process of embodiment 81, wherein the crystalline solid zoledronate sodium salt is the disodium salt.

85. The process of embodiment 84, wherein the crystalline solid zoledronate disodium is selected from the group consisting of Form V, Form VI, Form VII, Form X, Form XIII, Form XIV, Form XIX, Form XXV, and Form XXVII.

86. The process of embodiment 81, wherein the crystalline solid zoledronate sodium salt is the trisodium salt.

87. The process of embodiment 86, wherein the crystalline solid zoledronate trisodium is selected from the group consisting of Form IX and Form XI.

88. A process for preparing a crystalline solid zoledronate sodium salt comprising:
a) suspending zoledronic acid in a mixture of alcohol/water, preferably at reflux temperature
b) adding to the suspension of a) a solution of a base, preferably sodium hydroxide, in an equivalent mixture of alcohol/water as that used in the suspension of a), to form a reaction mixture; and
c) stirring the reaction mixture for a time sufficient to precipitate a crystalline solid zoledronate sodium salt.

89. The process of embodiment 88, wherein the reaction mixture is stirred at reflux for about 10 to about 20 hours, preferably about 14-16.

90. The process of embodiment 88, wherein the volume ratio of alcohol/water to zoledronic acid in a) and b) is 6-14 volumes, preferably 10 volumes.

91. The process of embodiment 88, wherein the alcohol in a) and b) is selected from the group consisting of methanol, ethanol, isopropanol and dimethylformamide.

92. The process of embodiment 88, wherein the zoledronic acid is zoledronic acid Form I and the ratio of acid to base is 1:1.

93. The process of embodiment 88, wherein the zoledronic acid is zoledronic acid Form I and the ratio of acid to base is 1:2.

94. The process of embodiment 88, wherein the zoledronic acid is zoledronic acid Form XII and the ratio of acid to base is 1:1.1.

95. The process of embodiment 92, wherein the crystalline solid zoledronate sodium salt is the monosodium salt.

96. The process of embodiment 95, wherein the crystalline solid zoledronate monosodium is selected from the group consisting of Form VIII, Form XVI and Form XVII.

97. The process of embodiment 93 or embodiment 94, wherein the crystalline solid zoledronate sodium salt is the disodium salt.

98. The process of embodiment 97, wherein the crystalline solid zoledronate disodium is selected from the group consisting of Form V, Form VI, Form VII, Form X, Form XIII, Form XIV, Form XIX, Form XXV, and Form XXVII.

99. The process of embodiment 0, wherein the zoledronic acid is zoledronic acid Form XII and the ratio of acid to base is 1:2.1.

100. The process of embodiment 99, wherein the crystalline solid zoledronate sodium salt is the trisodium salt.

101. The process of embodiment 100, wherein the crystalline solid zoledronate trisodium is selected from the group consisting of Form IX and Form XI.

102. A process for preparing a solid crystalline zoledronate sodium salt comprising:
  a) dissolving a crystal form of zoledronate sodium in water, preferably at reflux, to form a solution; and
  b) cooling the solution to precipitate a crystal form of zoledronate sodium which is different from the starting form in a).

103. The process of embodiment 102, wherein the water is added in an amount of between 20-30 volumes, preferably 25 volumes, per volume of zoledronate sodium.

104. A process for preparing crystalline solid zoledronate monosodium Form VIII comprising:
  a) adding a solution of a base in an 80%/20% v/v mixture of water/ethanol to a suspension of zoledronic acid form I in an 80%/20% v/v mixture of water/ethanol at elevated temperature, preferably reflux temperature;
  b) stirring the mixture of a) at reflux temperature for about 10 to 20 hours, preferably 14-16 hours; and
  c) precipitating zoledronate monosodium Form VIII.

105. The process of embodiment 104, wherein the base is sodium hydroxide, which is added in an amount of a 1:1 molar ratio to the zoledronic acid.

106. The process of embodiment 104, wherein the volume ratio of water/ethanol to zoledronic acid form I in the suspension and the solution is between 6 and 14, preferably 10.

107. A process for preparing crystalline solid zoledronate monosodium Form VIII comprising:
  a) adding a solution of a base in an 80%/20% v/v mixture of water/methanol to a suspension of zoledronic acid form I in an 80%/20% v/v mixture of water/methanol at elevated temperature, preferably reflux temperature;
  b) stirring the mixture of a) at reflux temperature for about 10 to 20 hours, preferably 14-16 hours; and
  c) precipitating zoledronate monosodium Form VIII.

108. The process of embodiment 107, wherein the base is sodium hydroxide, which is added in an amount of a 1:1 molar ratio to the zoledronic acid.

109. The process of embodiment 107, wherein the volume ratio of water/methanol to zoledronic acid form I in the suspension and the solution is between 6-14, preferably 10.

110. A process for preparing crystalline solid zoledronate monosodium Form VIII comprising:
  a) adding a solution of a base in an 60%/40% v/v mixture of water/isopropanol to a suspension of zoledronic acid form I in an 60%/40% v/v mixture of water/isopropanol at elevated temperature, preferably reflux temperature;
  b) stirring the mixture of a) at reflux temperature for about 10 to 20 hours, preferably 14-16 hours; and
  c) precipitating zoledronate monosodium Form VIII.

111. The process of embodiment 110, wherein the base is sodium hydroxide, which is added in an amount of a 1:1 molar ratio to the zoledronic acid.

112. The process of embodiment 110, wherein the volume ratio of water/isopropanol to zoledronic acid form I in the suspension and the solution is between 6 and 14, preferably 10.

113. A process for preparing crystalline solid zoledronate monosodium Form XVI comprising:
  a) adding a solution of a base in a 50%/o/50% v/v mixture of water/ethanol to a suspension of zoledronic acid form I in a 50%/50% v/v mixture of water/ethanol at elevated temperature, preferably reflux temperature;
  b) stirring the mixture of a) at reflux temperature for about 10 to 20 hours, preferably 14-16 hours; and
  c) precipitating zoledronate monosodium Form XVI.

114. The process of embodiment 113, wherein the base is sodium hydroxide, which is added in an amount of a 1:1 molar ratio to the zoledronic acid.

115. The process of embodiment 113, wherein the volume ratio of water/ethanol to zoledronic acid form I in the suspension and the solution is between 6 and 14, preferably 10.

116. A process for preparing crystalline solid zoledronate monosodium Form XVI comprising:
  a) adding a solution of a base in a 50%/50% v/v mixture of water/isopropanol to a suspension of zoledronic acid Form I in a 50%/50% v/v mixture of water/isopropanol at elevated temperature, preferably reflux temperature;
  b) stirring the mixture of a) at reflux temperature for about 10 to 20 hours, preferably 14 to 16 hours; and
  c) precipitating zoledronate monosodium Form XVI.

117. The process of embodiment 116, wherein the base is sodium hydroxide, which is added in an amount of a 1:1 molar ratio to the zoledronic acid.

118. The process of embodiment 116, wherein the volume ratio of water/isopropanol to zoledronic acid form I in the suspension and the solution is between 6 and 14, preferably 10.

119. A process for preparing crystalline solid zoledronate monosodium Form XVI comprising:
  a) adding a solution of a base in a 50%/50% v/v mixture of water/methanol to a suspension of zoledronic acid form I in a 50%/50% v/v mixture of water/ethanol at elevated temperature, preferably reflux temperature;
  b) stirring the mixture of a) at reflux temperature for about 10 to 20 hours, preferably 14 to 16 hours; and
  c) precipitating zoledronate monosodium Form XVI.

120. The process of embodiment 119, wherein the base is sodium hydroxide, which is added in an amount of a 1:1 molar ratio to the zoledronic acid.

121. The process of embodiment 119, wherein the volume ratio of water/methanol to zoledronic acid form I in the solution is between 6 and 14, preferably 10, and the volume ratio of water/ethanol in the suspension is between 6 and 14, preferably 10.

122. A process for preparing solid crystalline zoledronate sodium Form XVII comprising:
  a) dissolving zoledronic acid Form I in water to form a solution;
  b) adding a base, preferably sodium hydroxide, to the solution; and
  c) cooling the solution, optionally with the addition of an organic solvent, to precipitate crystalline zoledronate sodium Form XVII.

123. A pharmaceutical composition comprising the crystalline solid zoledronate monosodium of any of embodiments 35 to 43.

124. A pharmaceutical composition comprising the crystalline solid zoledronate disodium of any of embodiments 47 to 73.

125. A pharmaceutical composition comprising the crystalline solid zoledronate trisodium of any of embodiments 75 to 80.

126. Amorphous monosodium zoledronate.

127. Amorphous disodium zoledronate.

128. Amorphous trisodium zoledronate.

129. A pharmaceutical composition comprising the amorphous solid zoledronate of any of embodiments 126, 127 and 128.

130. A process for preparing zoledronate amorphous sodium comprising: treating zoledronic acid and a base, preferably sodium hydroxide, in water at room temperature and precipitating zoledronate amorphous sodium.

131. The process of embodiment 130, wherein the ratio of acid:base is 1:1.1.

132. The process of embodiment 130, wherein the ratio of acid:base is 1:2.1.

DETAILED DESCRIPTION OF THE INVENTION

Powder X-ray diffraction ("PXRD") analysis was performed on a Scintag X-Ray powder diffractometer model X'TRA equipped with a solid state detector. Copper radiation of 1.5418 Å was used. A round aluminum sample holder with round zero background quartz plate, with a cavity of 25 mm diameter and 0.5 mm depth, was used.

Loss on drying ("LOD") was measured by Thermal Gravimetric Analysis ("TGA") using a Mettler TG50. The sample size was about 9-15 mg. The samples were scanned at a rate of 10° C./min from 25° C. to 250° C. The oven was constantly purged with nitrogen gas at a flow rate of 40 ml/min. Standard alumina crucibles covered by lids with one hole were used.

DSC analysis was done using a Mettler 821 Star$^e$. The weight of the samples was about 3 mg. The samples were scanned at a rate of 10° C./min from 30° C. to 300° C. The oven was constantly purged with nitrogen gas at a flow rate of 40 ml/min. Standard 40 ml aluminum crucibles covered by lids with three holes were used.

Applicants have discovered that different crystal forms of Zoledronic acid may be obtained. Different forms of the zoledronic acid may have improved properties with regards to dissolution (since the dosage form is for injection, the material needs to be reconstituted in water; faster dissolution rate would mean faster reconstitution). The recrystallization of Zoledronic acid leads to a material with a purity of at least 99.5% area by HPLC.

The novel forms of zoledronic acid are hydrated. The level of water in Zoledronic acid is estimated by TGA the (thermogravimetric analysis) weight loss.

Zoledronic acid can be found in the anhydrous state (weight loss up to 2%), monohydrate (weight loss 5-8%), sesquihydrate (weight loss 9-11%).

Figure 2:
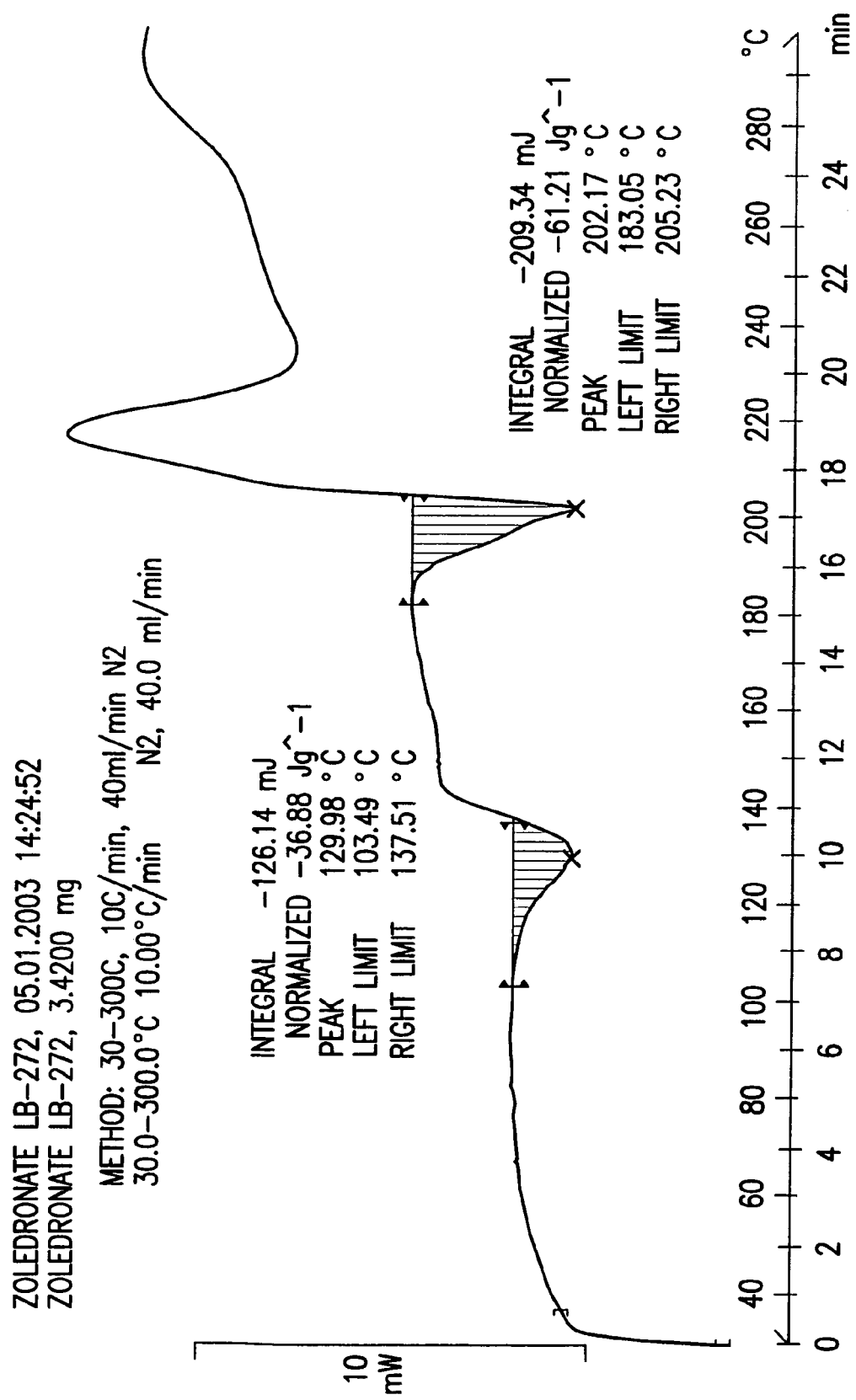
FIG. 2 is a representative DSC curve of zoledronic acid Form I.

A typical DSC scan of zoledronic acid shows an endothermic peak below about 160-170° C. due mainly to water desorption, and a subsequent endotherm at about 200° C. concomitant to an exotherm reaction (see FIG. 2). From this DSC scan there is no clear detection of a melting point.

Zoledronic Acid Form I

In a first aspect, the invention provides a novel crystalline solid form of Zoledronic acid that has been denominated Form I. Zoledronic acid Form I identified by its PXRD pattern, a representative example of which is provided in the diffractogram of FIG. 1. Particular characteristic peaks occur at 12.1, 12.8, 15.7, and 18.9±0.2° 2θ. Additional peaks occur at 20.9, 21.3, 21.8, 22.2, 25.8, 27.6, 29.2, 32.5, and 32.9±0.2° 2θ. The hydration level of Zoledronic acid Form I is indicated by a LOD of 5% to 8% (monohydrate) on heating from about 25-220° C.

Zoledronic acid Form I is substantially free of Zoledronic acid Form II. In addition, Zoledronic acid Form I is substantially free of other polymorphic forms of Zoledronic acid. Substantially free means less than about 5%. A suitable method for detecting other phases and mixtures of polymorphs is the X-Ray powder diffraction method (see "Polymorphism in molecular crystals", Joel Bernstein, Oxford Science Publications, or "Polymorphism in pharmaceutical solids" edited by Harry G. Brittain).

Zoledronic acid Form I is physically stable and does not substantially transform to any other crystal form when exposed to 100% relative humidity (RH) or less, for one week, or stored at 40° C. and 75% RH for 3 months. After exposure to 100% RH or less, for one week, there is no significant gain of moisture in Form I (not significant means that it absorbs less than about 0.2% water). "Substantially transforms to any other crystal form" means that more than about 5% of the crystal form converts or rearranges to Form II or any other crystal form.

Accordingly in one embodiment, the invention provides a pharmaceutical composition comprising zoledronic acid Form I substantially free of other polymorphic forms of zoledronic acid and at least one pharmaceutically acceptable excipient. Preferably the pharmaceutical composition is in the form of an oral solid dosage form.

In another embodiment, the invention provides a pharmaceutical composition comprising zoledronic acid Form I, which is physically stable and does not substantially transform to any other crystal form when stored at 40° C. and 75% RH for 3 months, and at least one pharmaceutically acceptable excipient. Preferably the pharmaceutical composition is in the form of an oral solid dosage form.

The novel crystal forms of Zoledronic acid preferably have a particle size distribution such that 100% of the particles have a size below 100 microns, preferably below 50 microns.

Accordingly, another aspect of the invention is a pharmaceutical composition comprising a novel crystal form of zoledronic acid, which has a particle size distribution such that 100% is below 100 microns, preferably below 50 microns, and at least one pharmaceutically acceptable excipient.

Zoledronic acid Form I can be prepared by a phosphorylation reaction of 1-Imidazoleacetic acid (IAA) in the presence of Phosphorous acid and Phosphorous oxychloride in a diluent, such as, Toluene, Chlorobenzene, PEG-400 and Silicon oil. Phosphorous oxychloride is added to a mixture of Phosphorous acid and IAA at 75° C. to 80° C. The reaction mixture is then stirred at 80° C.-100° C., preferably at 80° C. for 1-34 hours, preferably 5-25 hours. Then water is added at 80° C.-100° C. and the aqueous phase is separated. Hydrolysis occurs in about 10-20 hrs, preferably 14-16 hours. At the end of hydrolysis, a solvent like ethanol or acetone may be added to obtain a precipitate of ZLD-Ac after stirring at 5° C. for 1-6 hours, preferably 2.5-4 hours.

Zoledronic Acid Form II

Figure 3:
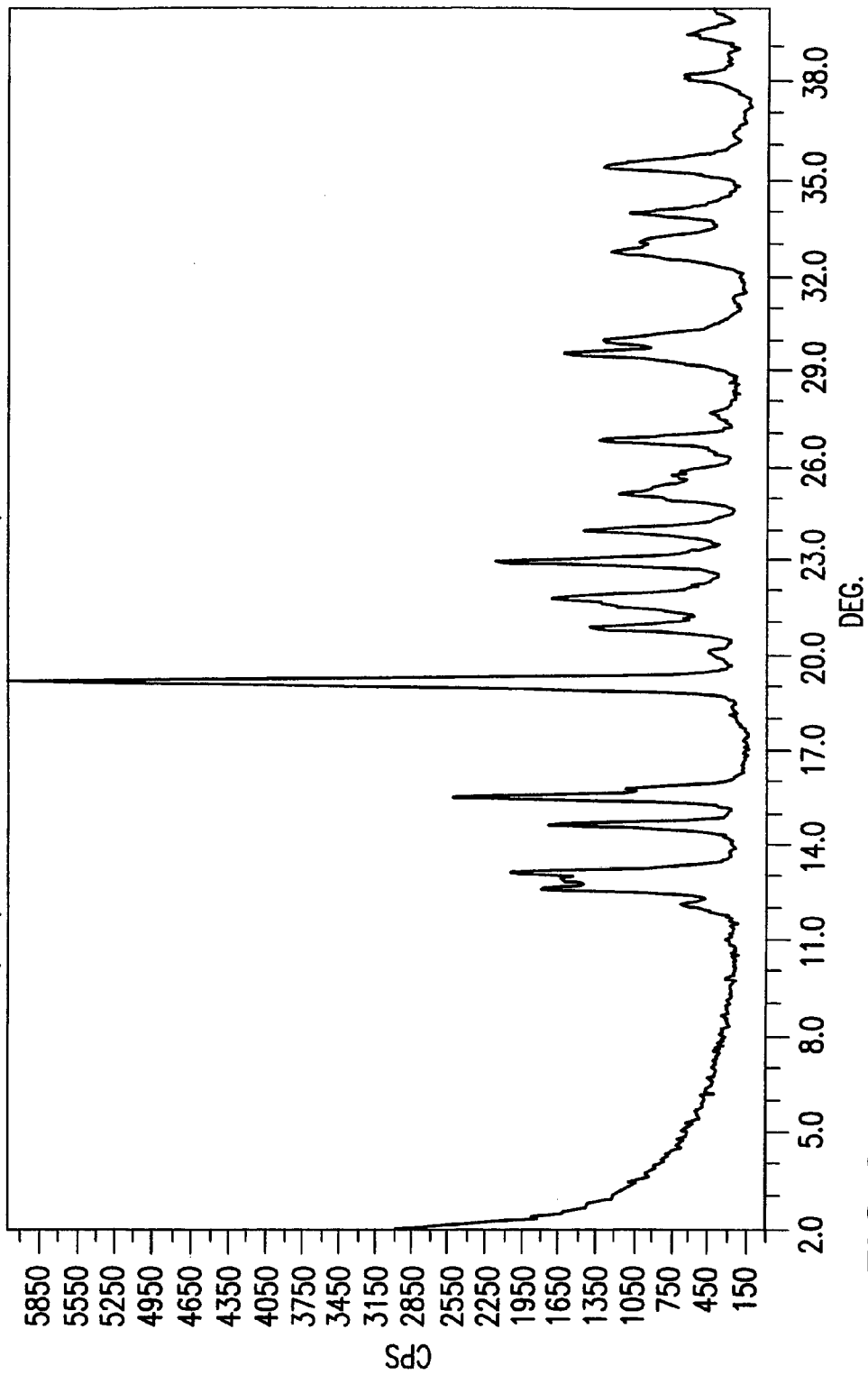
FIG. 3 is a representative PXRD pattern of zoledronic acid Form II.

In a second aspect, the invention provides a novel crystalline solid form of Zoledronic acid that has been denominated Form II. Zoledronic acid Form II can be identified by its PXRD pattern, a representative example of which is provided in the diffractogram of FIG. 3. Particular characteristic peaks occur at 14.6°, 15.4°, 19.1°, 22.9°, and 23.9° 2θ±0.2° 2θ. Additional peaks occur at 20.8°, 21.7°, 25.1°, 26.7°, 29.5°, and 29.9° 2θ±0.2° 2θ. The hydration level of Zoledronic acid Form II is indicated by a LOD of about 5% (monohydrate) on heating from about 25-220° C.

Form II can be prepared by a phosphorylation reaction of 1-Imidazoleacetic acid (IAA, 1 eq.) in the presence of Phosphorous acid (2 eq.) and Phosphorous oxychloride (.NET.) in silicon oil as a diluent. Phosphorous oxychloride is added to a mixture of phosphorous acid and IAA at 75° C. The reaction mixture is then heated to 80° C. for about 27 hours. Then water is added at 80° C. and the aqueous phase is separated. Hydrolysis usually occurs within about 10-20 hrs, preferably 14-16 hours. At the end of hydrolysis, ethanol is added to obtain a precipitate of ZLD-Ac after stirring at 5° C. for 1-6 hours, preferably 2.5-4 hours.

Zoledronic acid Form II can also be prepared by treating Zoledronic acid form I in Toluene, preferably at reflux temperature, for a duration of 5-20 hours, most preferably 10-16 hours.

Zoledronic Acid Form XI

Figure 4:
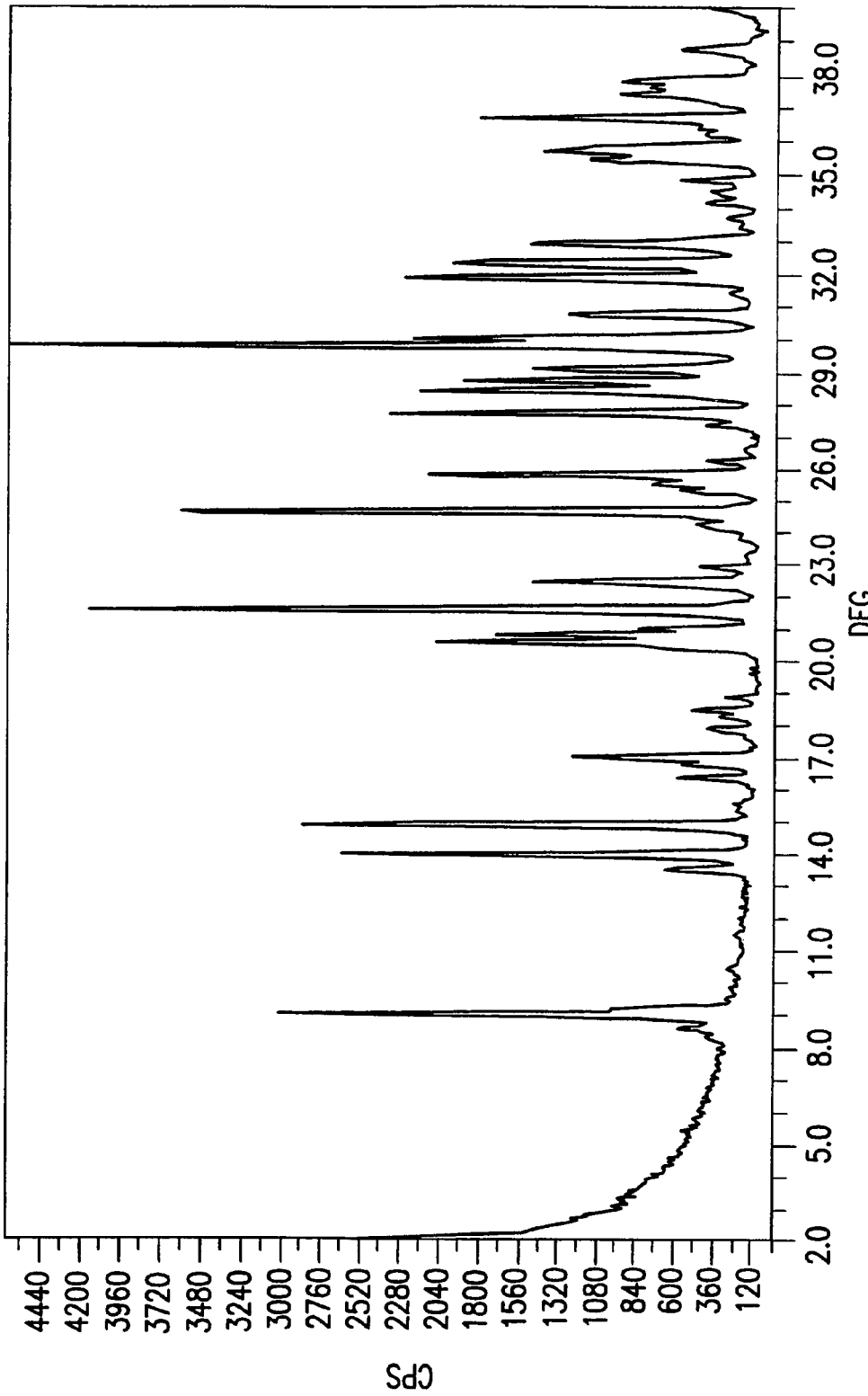
FIG. 4 is a representative PXRD pattern of zoledronic acid Form XII.

In a third aspect, the invention provides a novel crystalline solid form of Zoledronic acid that has been denominated Form XII. Zoledronic acid Form XII can be identified by its PXRD pattern, a representative example of which is provided in the diffractogram of FIG. 4. Particular characteristic peaks occur at 9.0, 13.9, 14.8, 21.5, 24.7, and 29.8±0.2° 2θ. Additional peaks occur at 17.0°, 20.6°, 20.8°, 22.4°, 25.8°, 27.7°, 28.4°, 28.7°, 29.1°, 30.8°, 31.9°, 32.3°, and 32.9° 2θ±0.2° 2θ. The hydration level of Zoledronic acid form XII is indicated by a LOD of about 6-10%, preferably 6% (monohydrate) on heating from about 25-220° C.

Zoledronic acid Form XII can be prepared by treating Zoledronic acid form XVIII in water at reflux temperature, the diluent/solid ratio being 10-30 volumes, preferably 24-26 volumes, and cooling the solution to room temperature or less.

Zoledronic Form XII can be also be prepared by stirring Form I in acetic acid.

Zoledronic Acid Form XV

Figure 5:
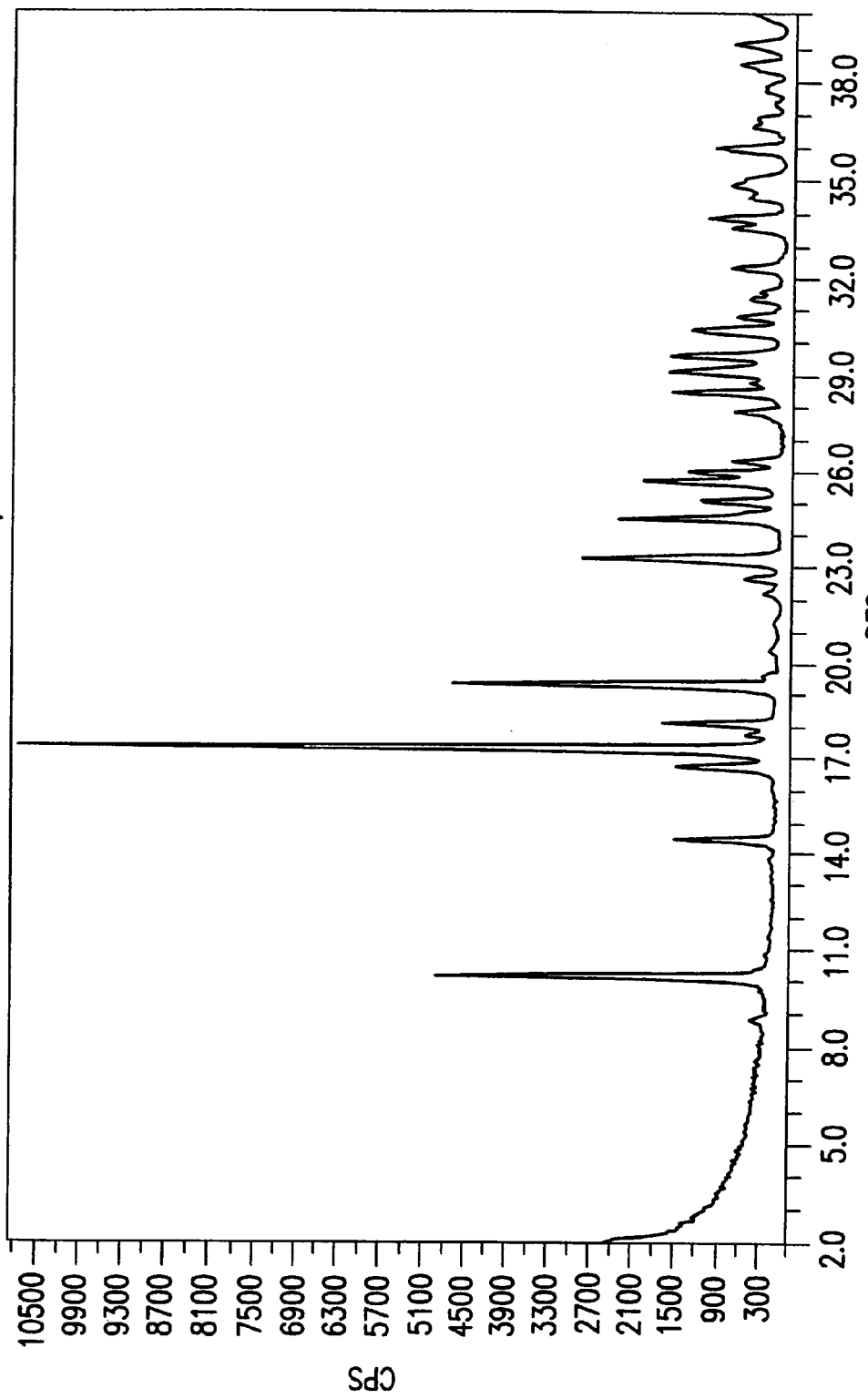
FIG. 5 is a representative PXRD pattern of zoledronic acid Form XV.

In a fourth aspect, the invention provides a novel crystalline solid form of Zoledronic acid denominated Form XV. Zoledronic acid Form XV can be identified by its PXRD pattern, a representative example of which is provided in FIG. 5. Particular characteristic peaks occur at 10.1°, 17.3°, 19.3°, and 23.2° 2θ±0.2° 2θ. Additional peaks occur at 14.5°, 16.7°, 18.1°, 24.5°, 25.1°, 25.7°, 28.5°, 29.1°, 29.6°, and 30.4° 2θ±0.2° 2θ. The TGA of form XV shows a LOD of 1% (anhydrous) within the temperature range 25-220° C.

Zoledronic acid Form XV can be prepared by treating any form of Zoledronic acid (preferably form I) and sodium hydroxide (1:1 mole ratio) in absolute ethanol (10 volumes per grams of ZLD-Ac) at reflux temperature for a duration of 5-20 hours, most preferably 10-16 hours.

Zoledronic acid Form XV can also be prepared by treating any form of Zoledronic acid (preferably form I or form XII) and sodium hydroxide (1:1 mole ratio) in methanol (10 volumes per grams of ZLD-Ac) at reflux temperature for a duration of 5-20 hours, most preferably 10-16 hours.

Zoledronic Acid Form XVIII

Figure 6:
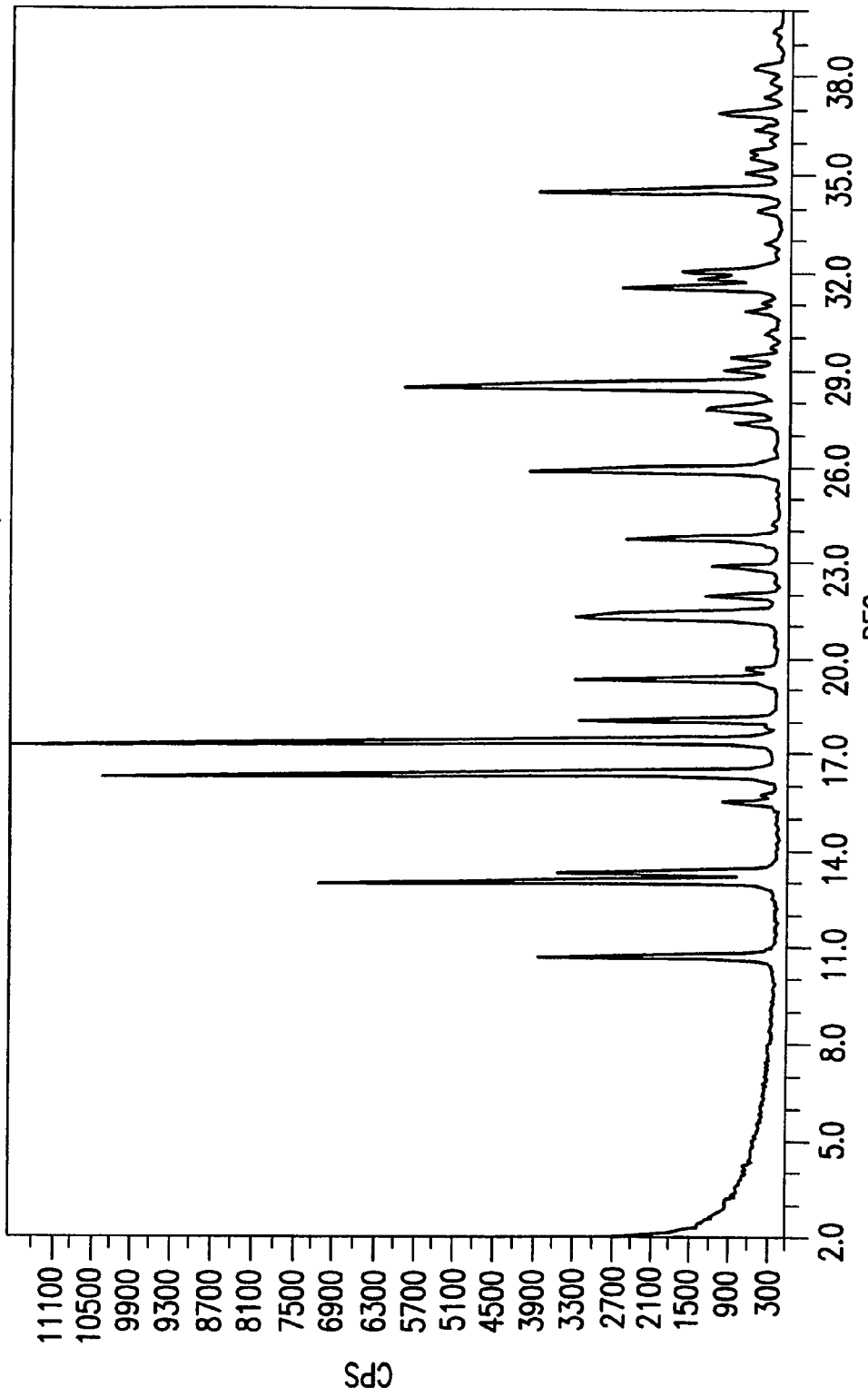
FIG. 6 is a representative PXRD pattern of zoledronic acid Form XVIII.

In a fifth aspect, the invention provides a novel crystalline solid form of Zoledronic acid denominated Form XVIII. Zoledronic acid Form XVIII can be identified by its PXRD pattern, a representative example of which is provided in FIG. 6. Particular characteristic peaks occur at 10.7°, 13.0°, 16.4°, 17.4°, and 28.5° 2θ±0.2° 2θ. Additional peaks occur at 13.3°, 18.1°, 19.3°, 21.3°, 23.7°, 25.9°, 31.5°, and 34.5° 2θ±0.2° 2θ. The TGA weight loss curve of Zoledronic acid form XVIII shows a LOD between 0.3% and about 6%, preferably 6% (monohydrate) within the temperature range 25-220° C.

Zoledronic acid Form XVIII can be prepared by a reaction of 1-Imidazoleacetic acid, Phosphorous acid and Silicon oil. Phosphorous oxychloride is added to the reaction mixture at 80° C. and the reaction mixture is stirred at this temperature for 22 hours. The aqueous phase is separated after addition of water and heated to reflux temperature for a 16 hours. Then absolute ethanol is added and the solution is kept at reflux temperature for 2 hours. Then the solution is cooled gradually to 25° C. to obtain a precipitate of ZLD-Ac.

Zoledronic acid Form XVIII can be also prepared by treating Zoledronic acid form I in methanol, 1-butanol, MTBE, acetonitrile, methanol/water 1:1 or ethanol water 1:1 (10 volumes per grams of ZLD-Ac), at room temperature or reflux temperature, for a duration of 5-20 hours, most preferably 10-16 hours.

Zoledronic Acid Form XX

Figure 7:
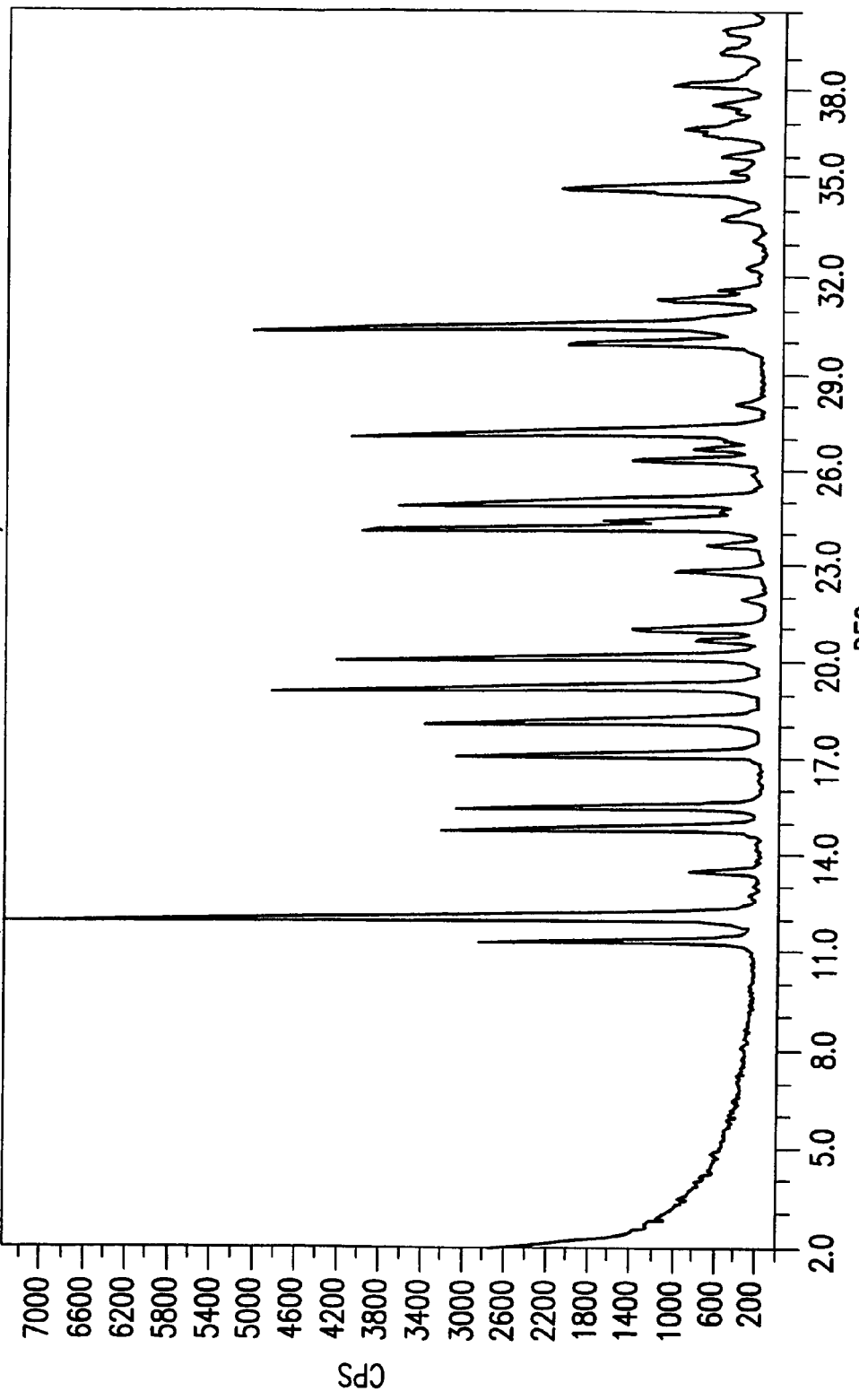
FIG. 7 is a representative PXRD pattern of zoledronic acid Form XX.

In a sixth aspect, the invention provides a novel crystalline solid form of Zoledronic acid denominated Form XX. Zoledronic acid Form XX can be identified by its PXRD pattern, a representative example of which is provided in FIG. 7. Particular characteristic peaks occur at 12.2°, 19.3°, 20.2°, 21.3°, 25.1°, and 27.2° 2θ±0.2° 2θ. Additional peaks occur at 11.4°, 14.9°, 15.5°, 17.2°, 18.2°, and 30.5° 2θ±0.2° 2θ. The TGA weight loss curve of Zoledronic acid form XX shows a LOD of about 0.5% (anhydrous) within the temperature range 25-220° C.

Zoledronic acid Form XX can be prepared by treating Zoledronic acid form I in ethanol, (preferably absolute), 1-propanol, 2-propanol (IPA), preferably at reflux temperature, the diluent/solid ratio being 15-25 volumes, preferably 10 volumes, for a duration of 5-20 hours, most preferably 10-16 hours.

Zoledronic Acid Form XXVI

Figure 8:
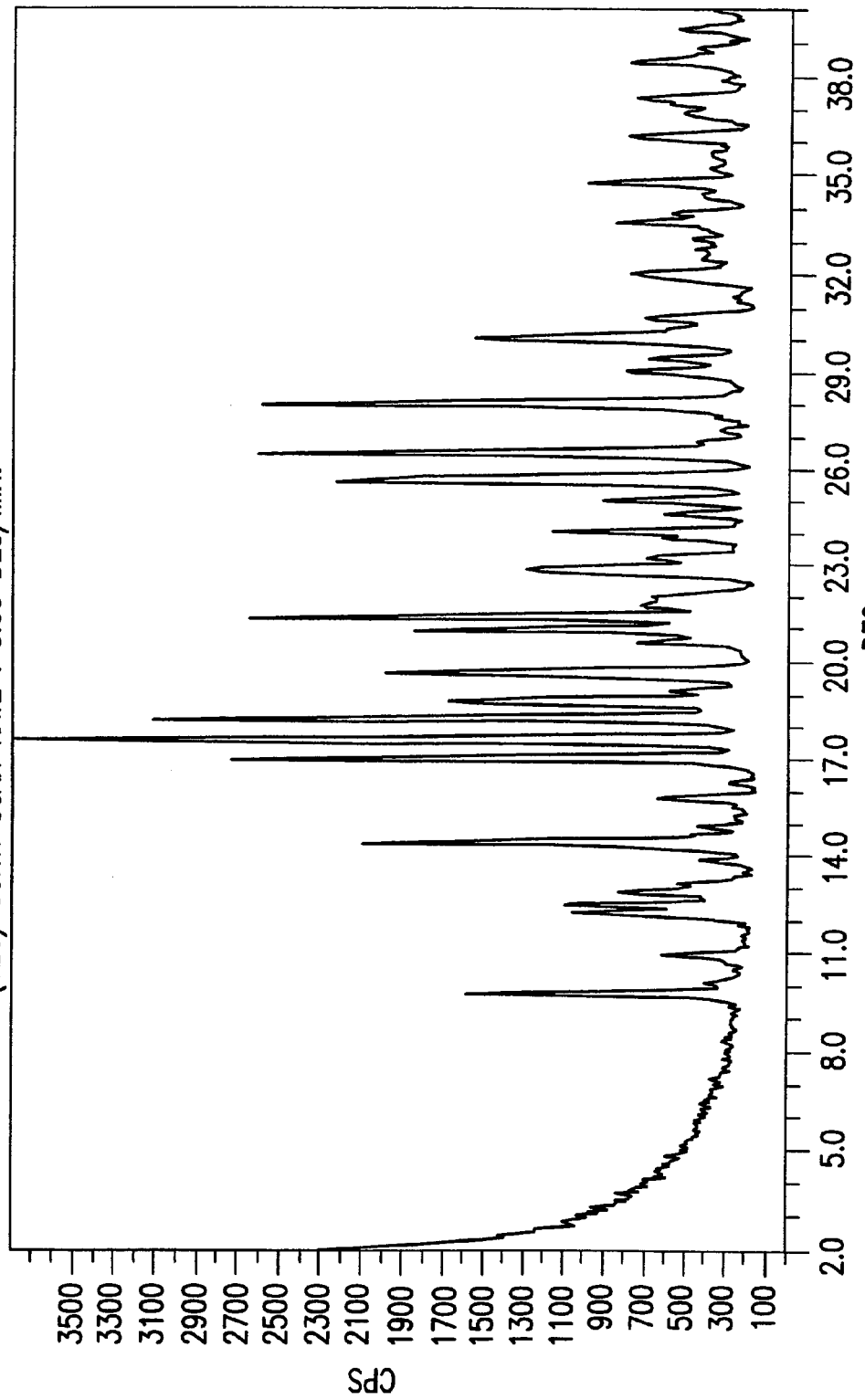
FIG. 8 is a representative PXRD pattern of zoledronic acid Form XXVI.
Figure 9:
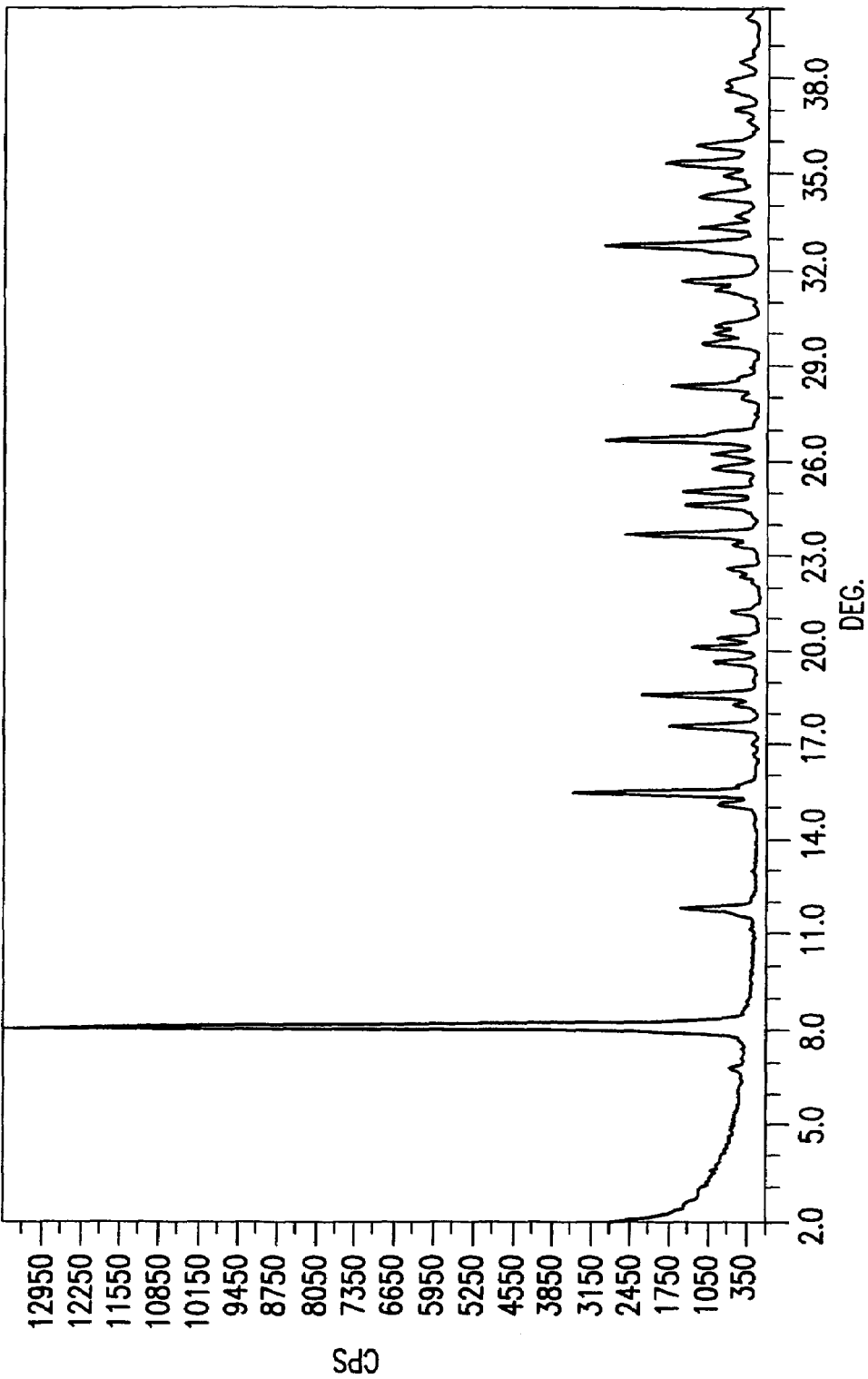
FIG. 9 is a representative PXRD pattern of zoledronate monohydrate Form VIII.
Figure 10:
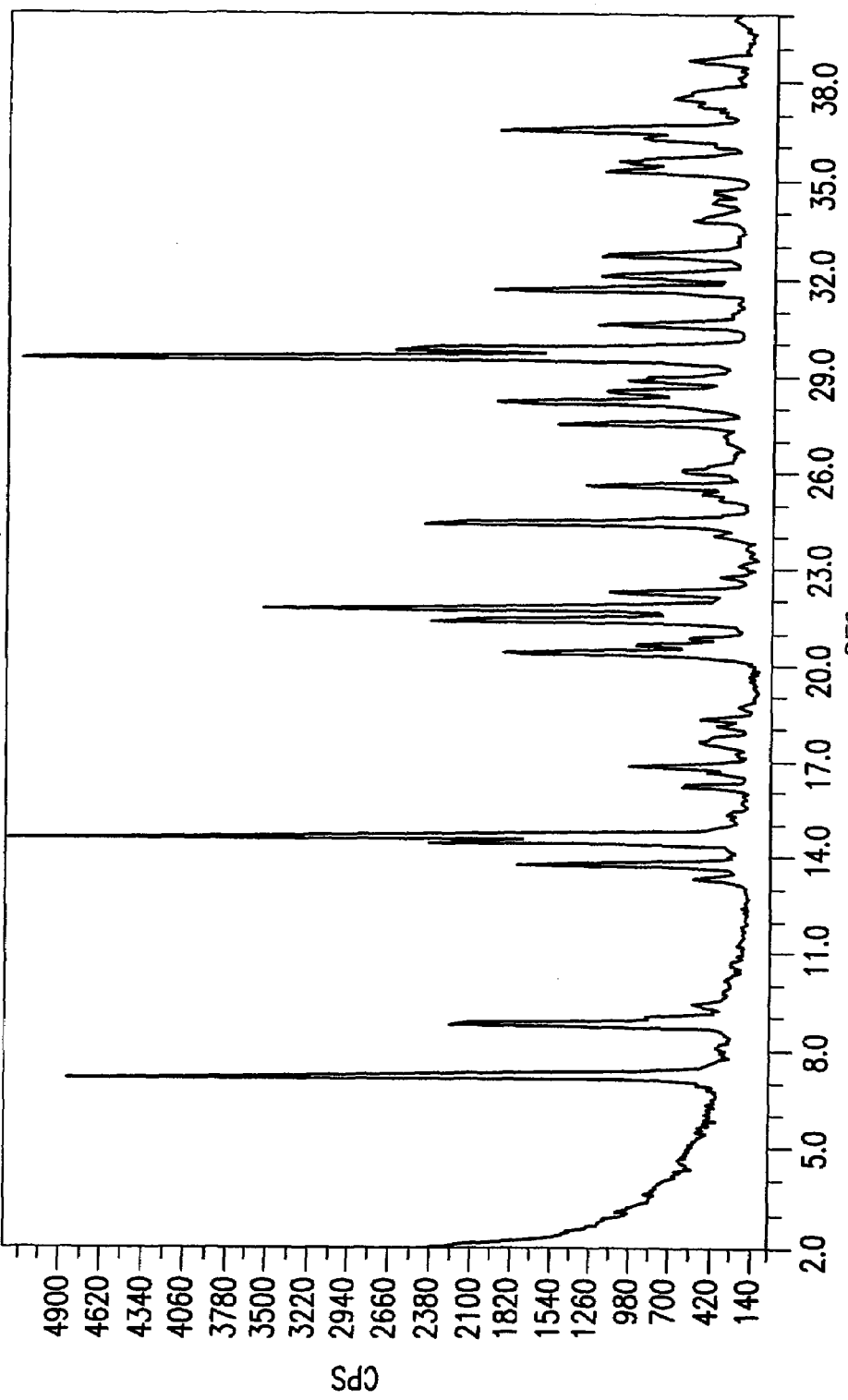
FIG. 10 is a representative PXRD pattern of zoledronate monosodium Form XVI.
Figure 11:
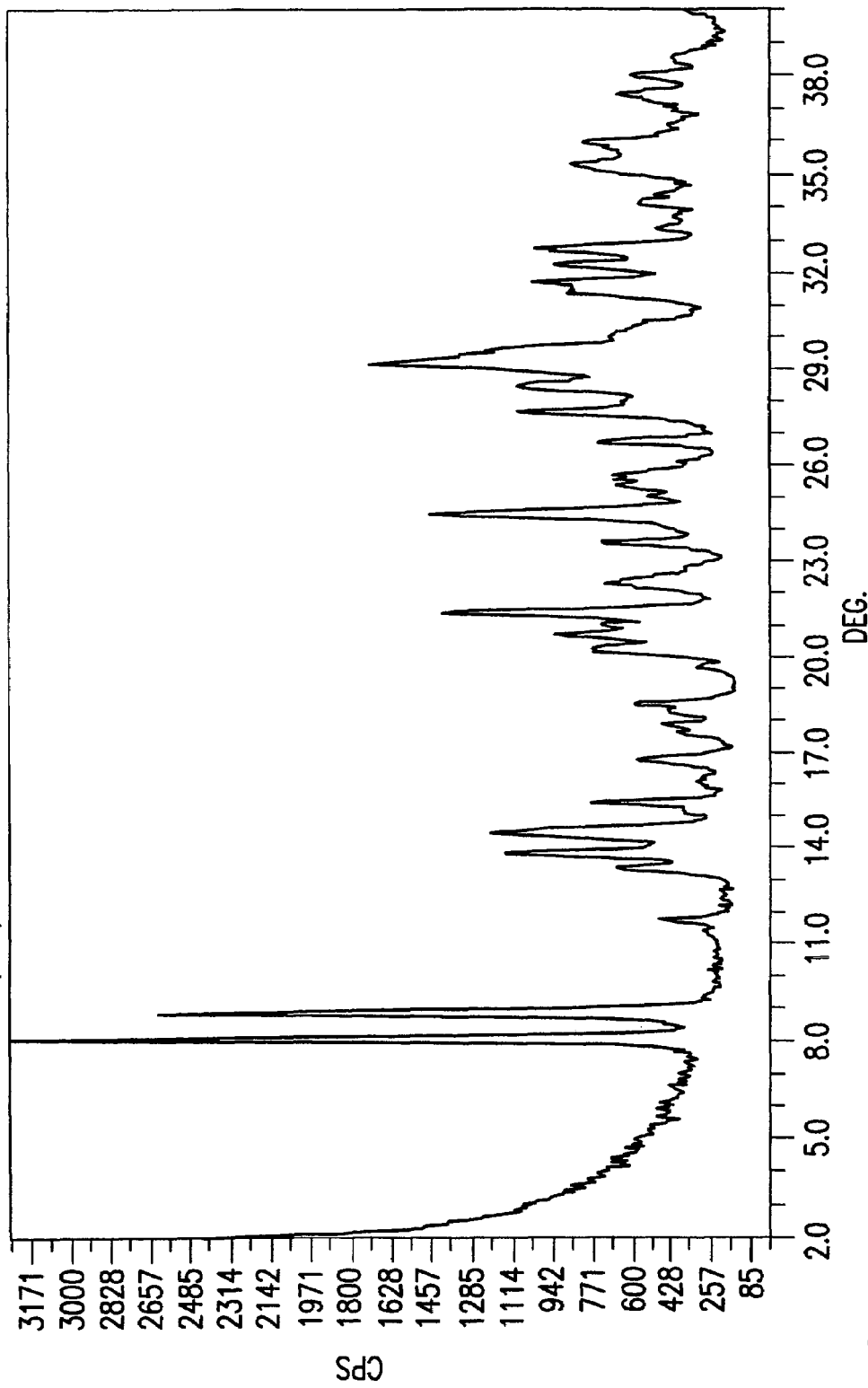
FIG. 11 is a representative PXRD pattern of zoledronate monosodium Form XVII.
Figure 12:
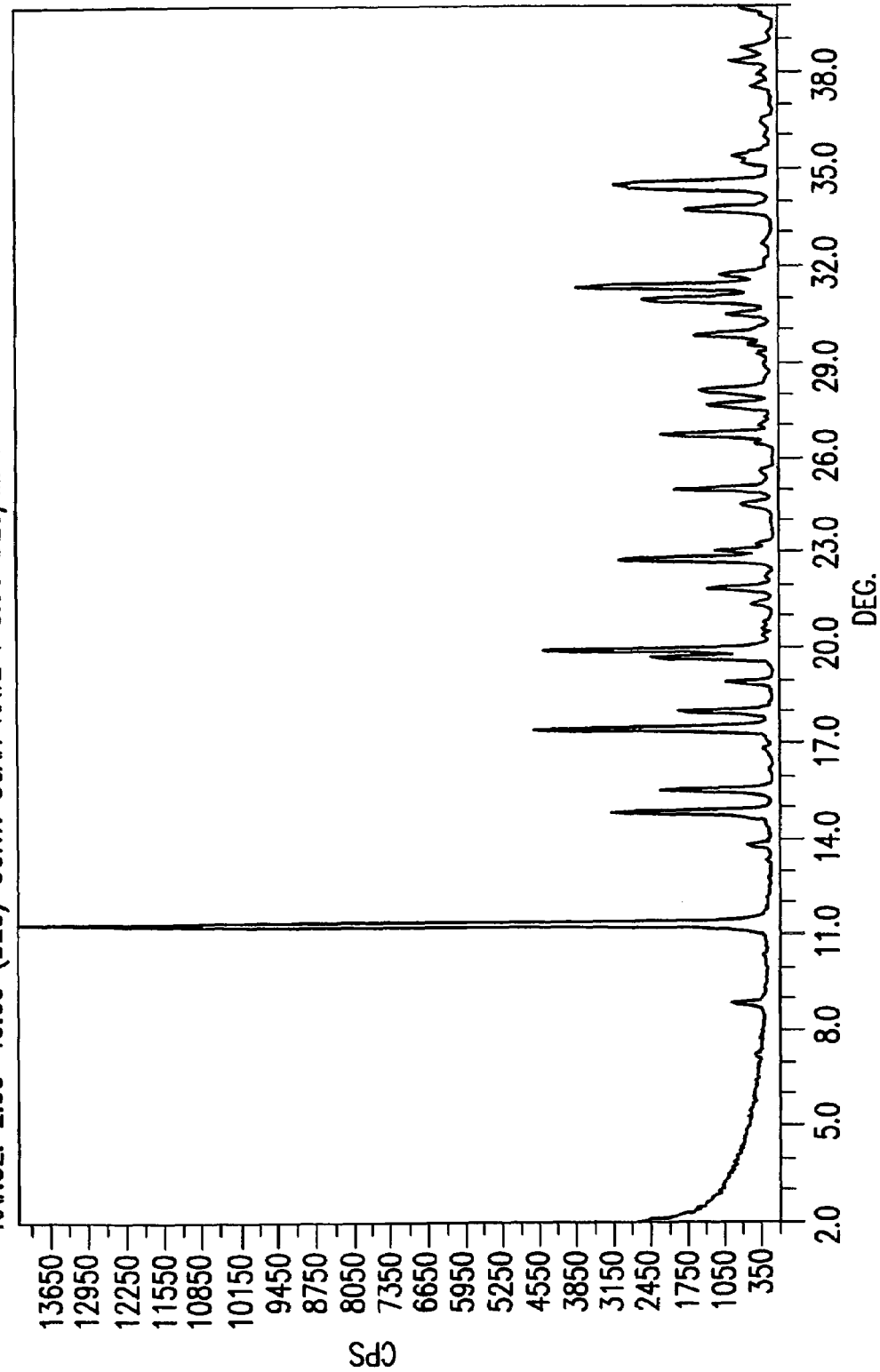
FIG. 12 is a representative PXRD pattern of zoledronate disodium Form V.
Figure 13:
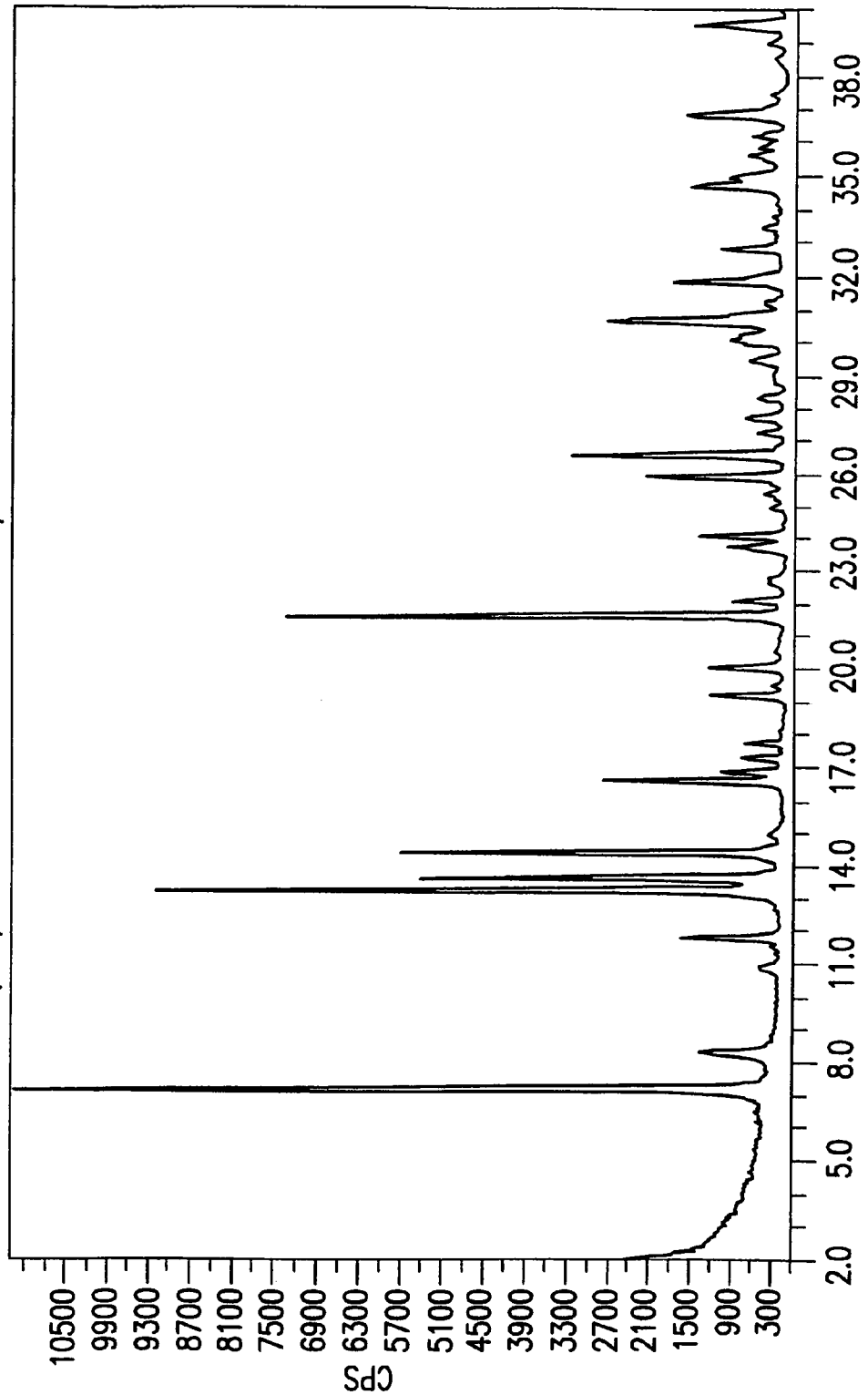
FIG. 13 is a representative PXRD pattern of zoledronate disodium Form VI.
Figure 14:
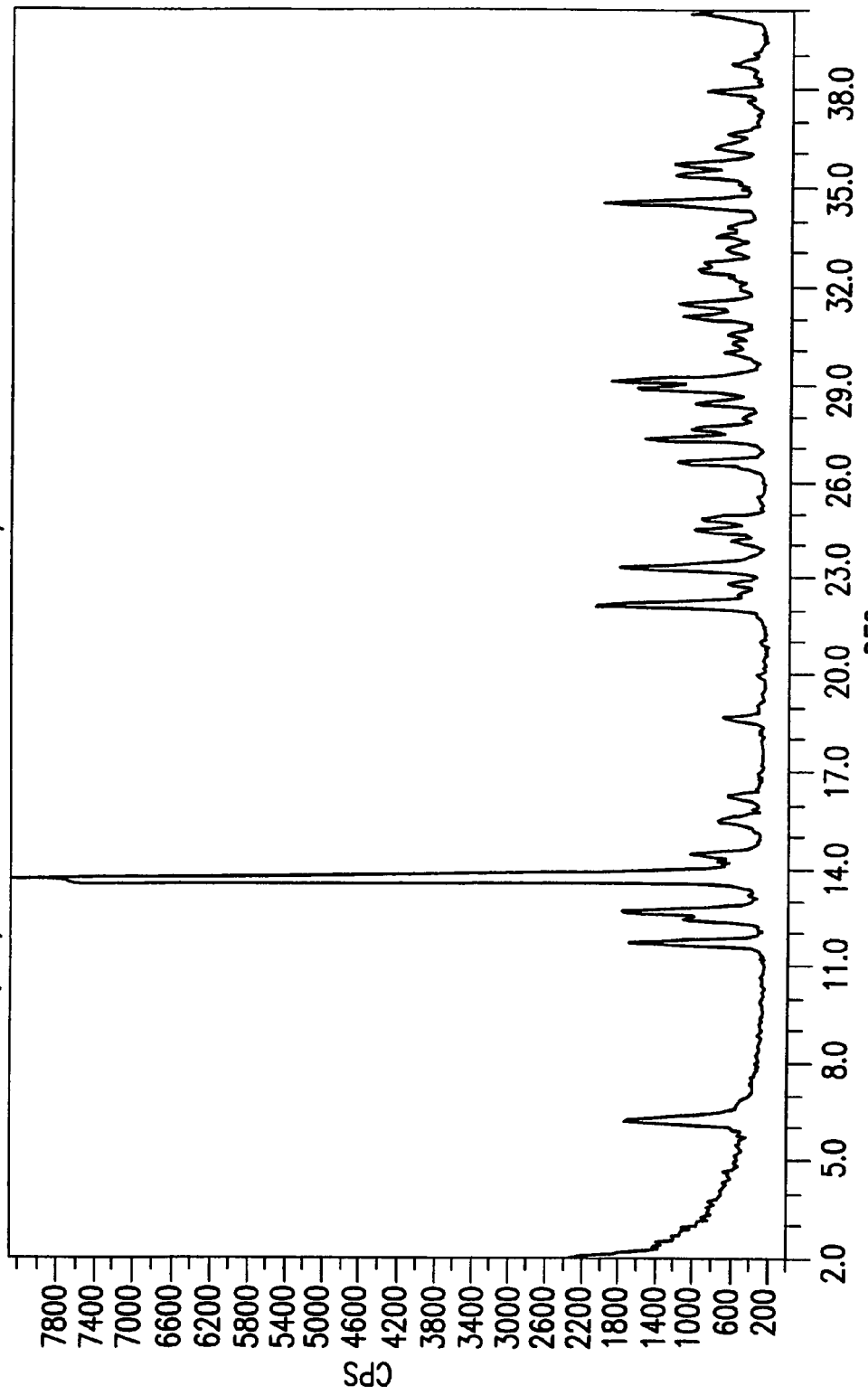
FIG. 14 is a representative PXRD pattern of zoledronate disodium Form VII.
Figure 15:
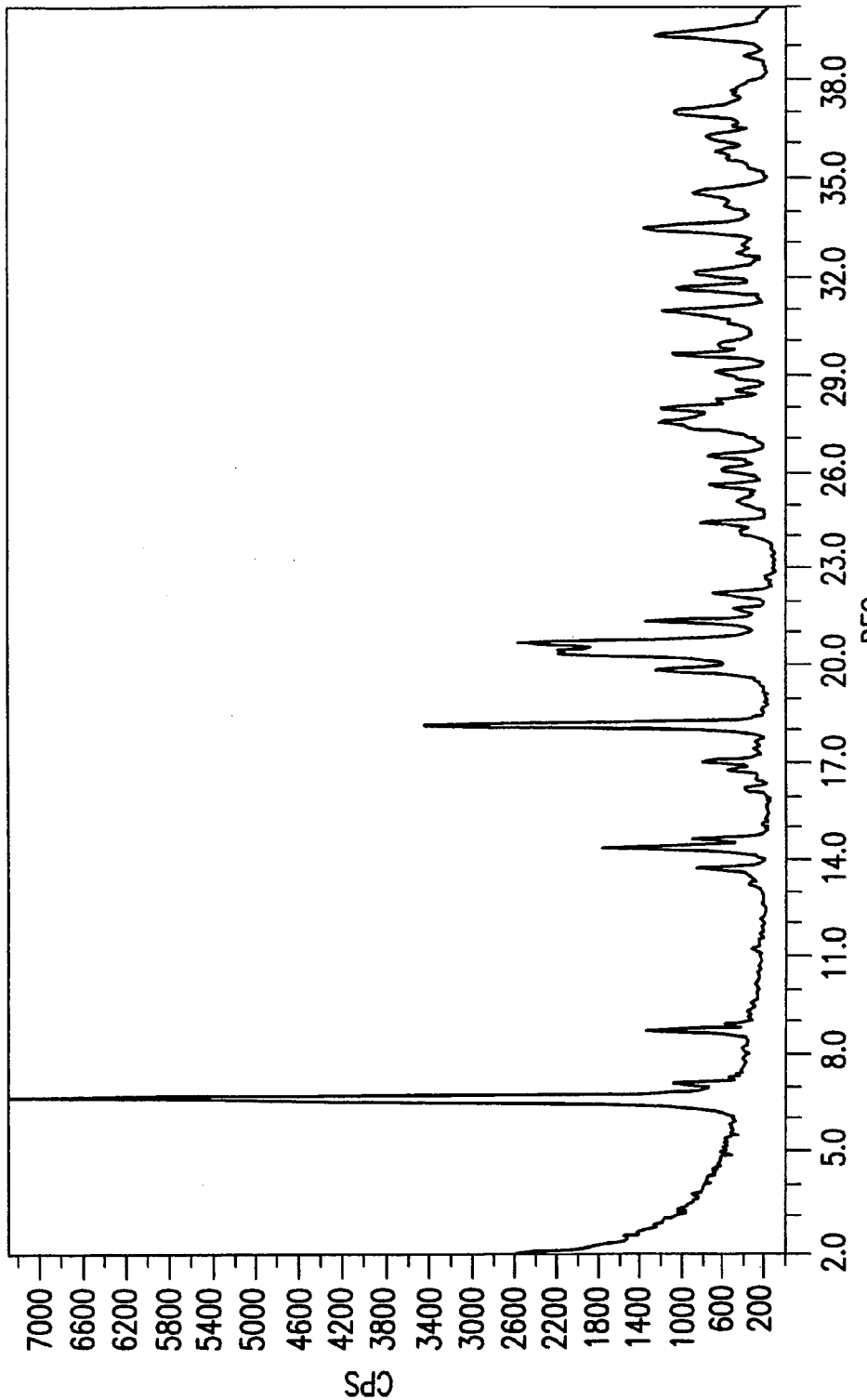
FIG. 15 is a representative PXRD pattern of zoledronate disodium Form X.
Figure 16:
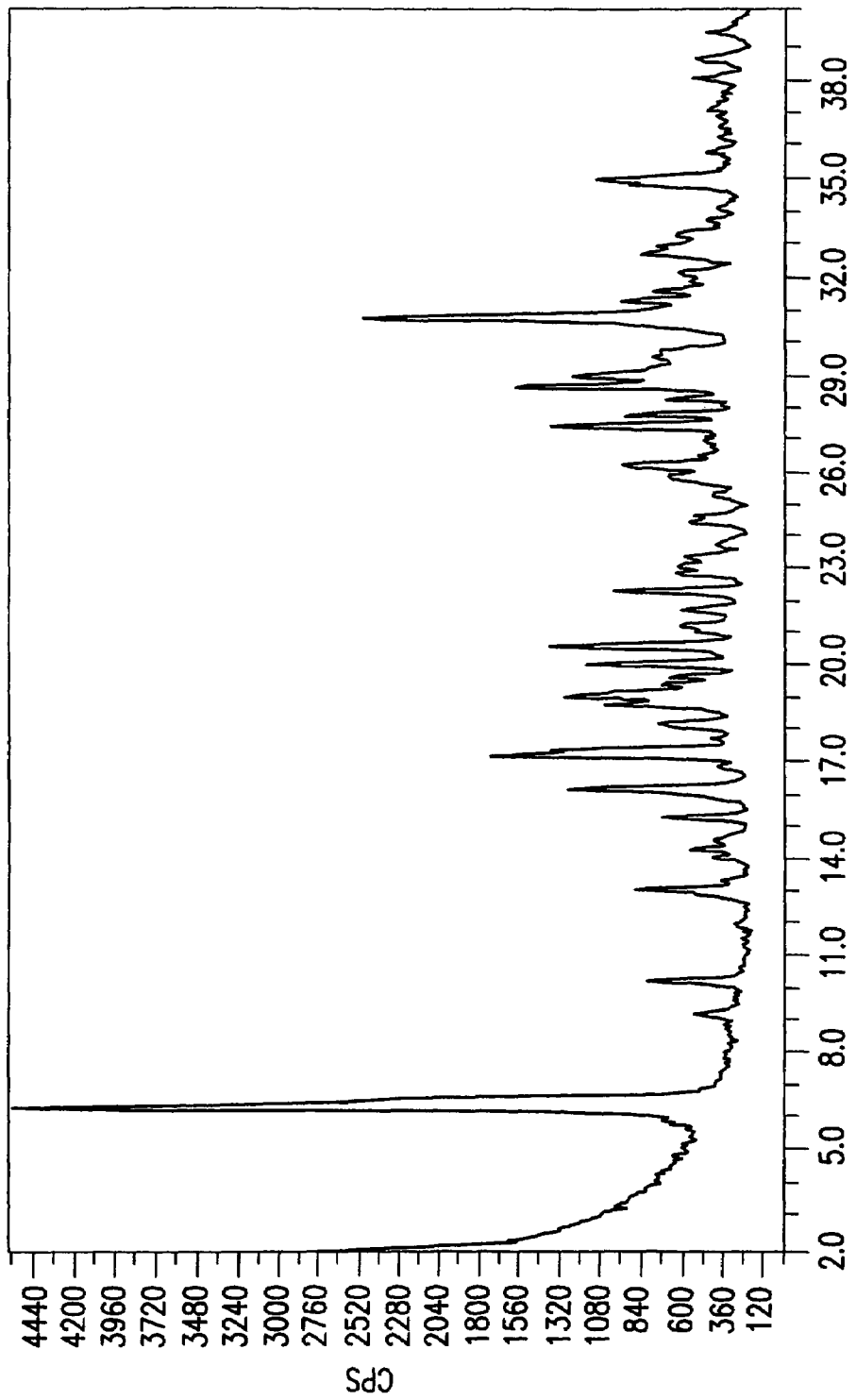
FIG. 16 is a representative PXRD pattern of zoledronate disodium Form XIII.
Figure 17:
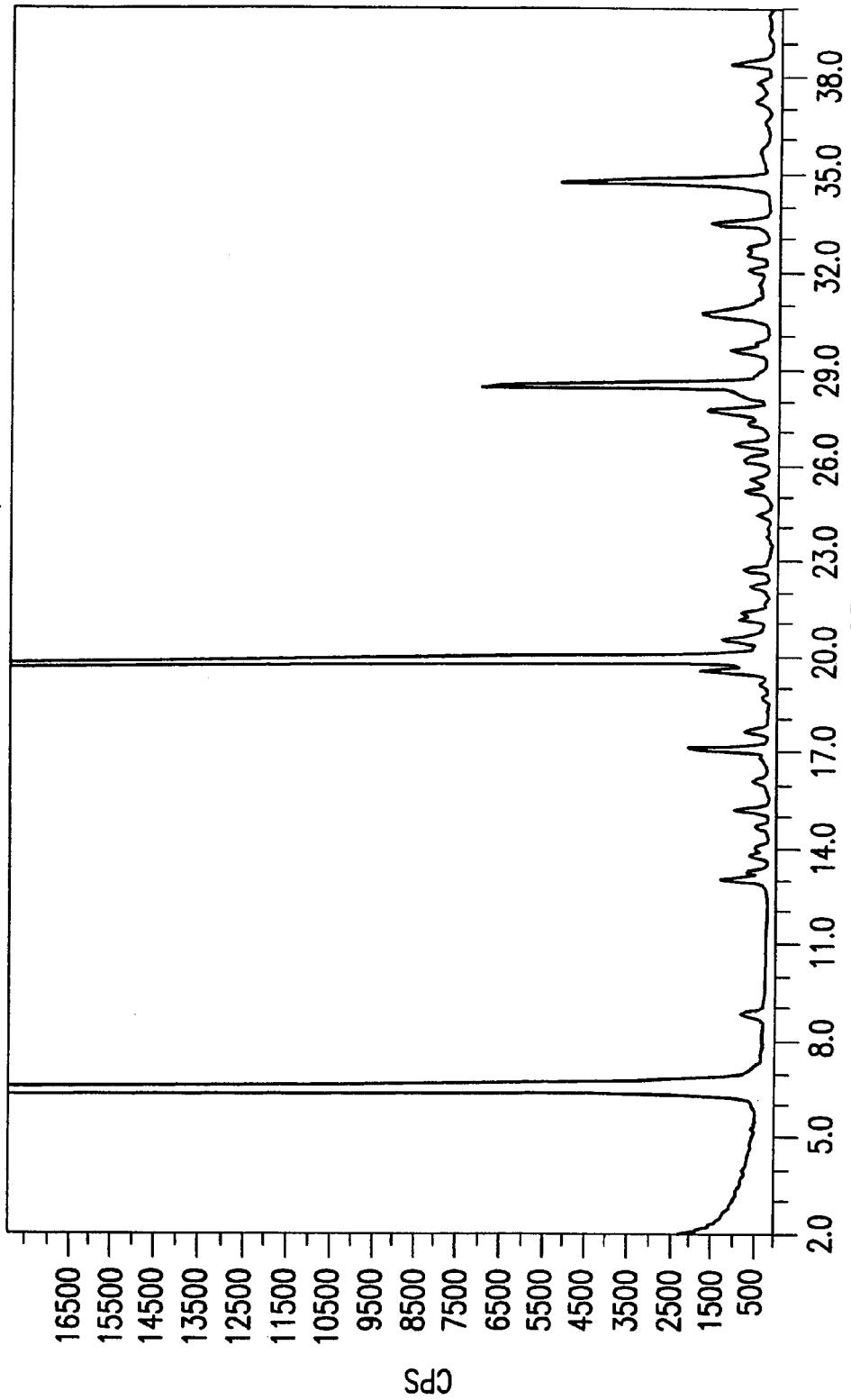
FIG. 17 is a representative PXRD pattern of zoledronate disodium Form XIV.
Figure 18:
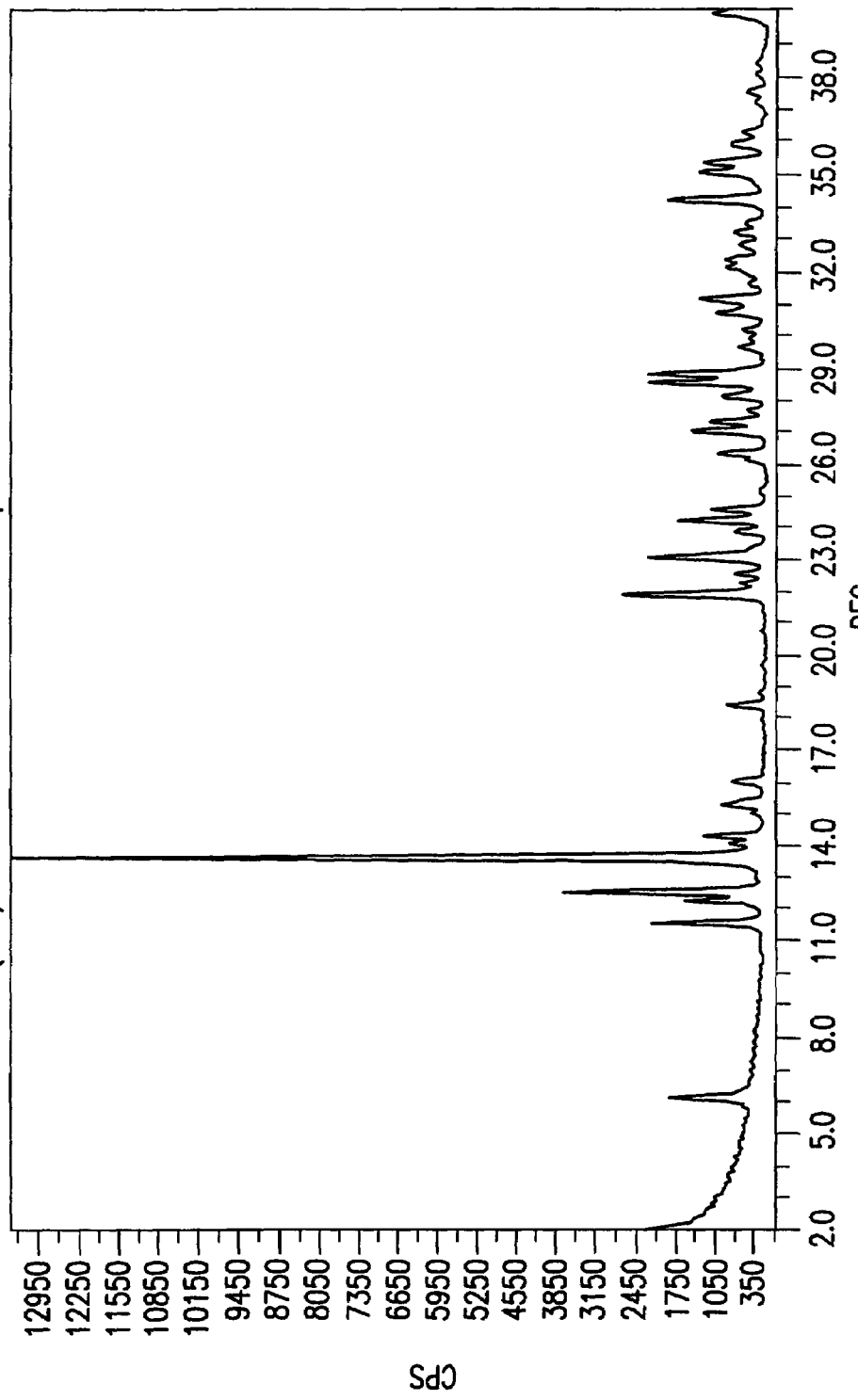
FIG. 18 is a representative PXRD pattern of zoledronate disodium Form XIX.
Figure 19:
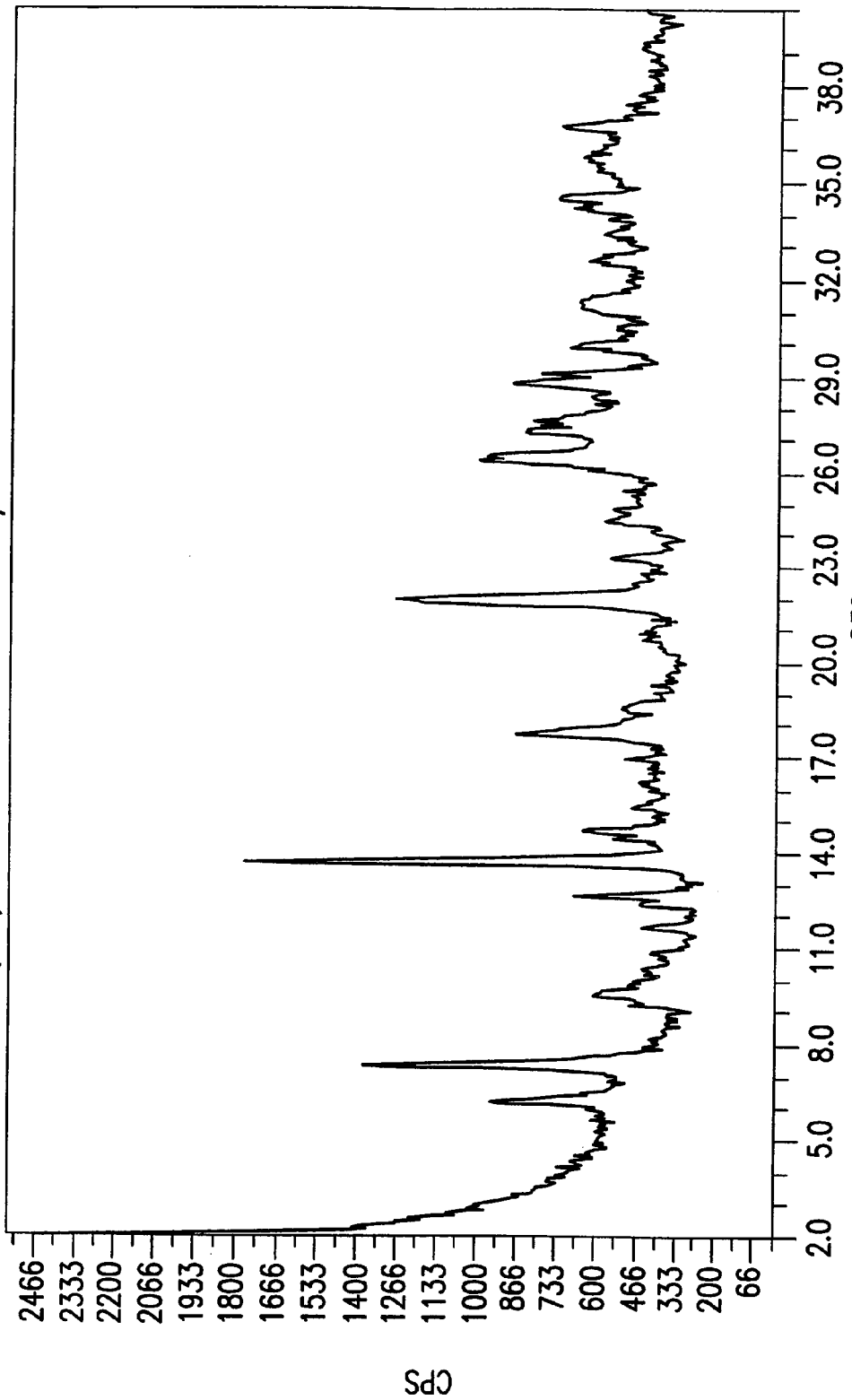
FIG. 19 is a representative PXRD pattern of zoledronate disodium Form XXV.
Figure 20:
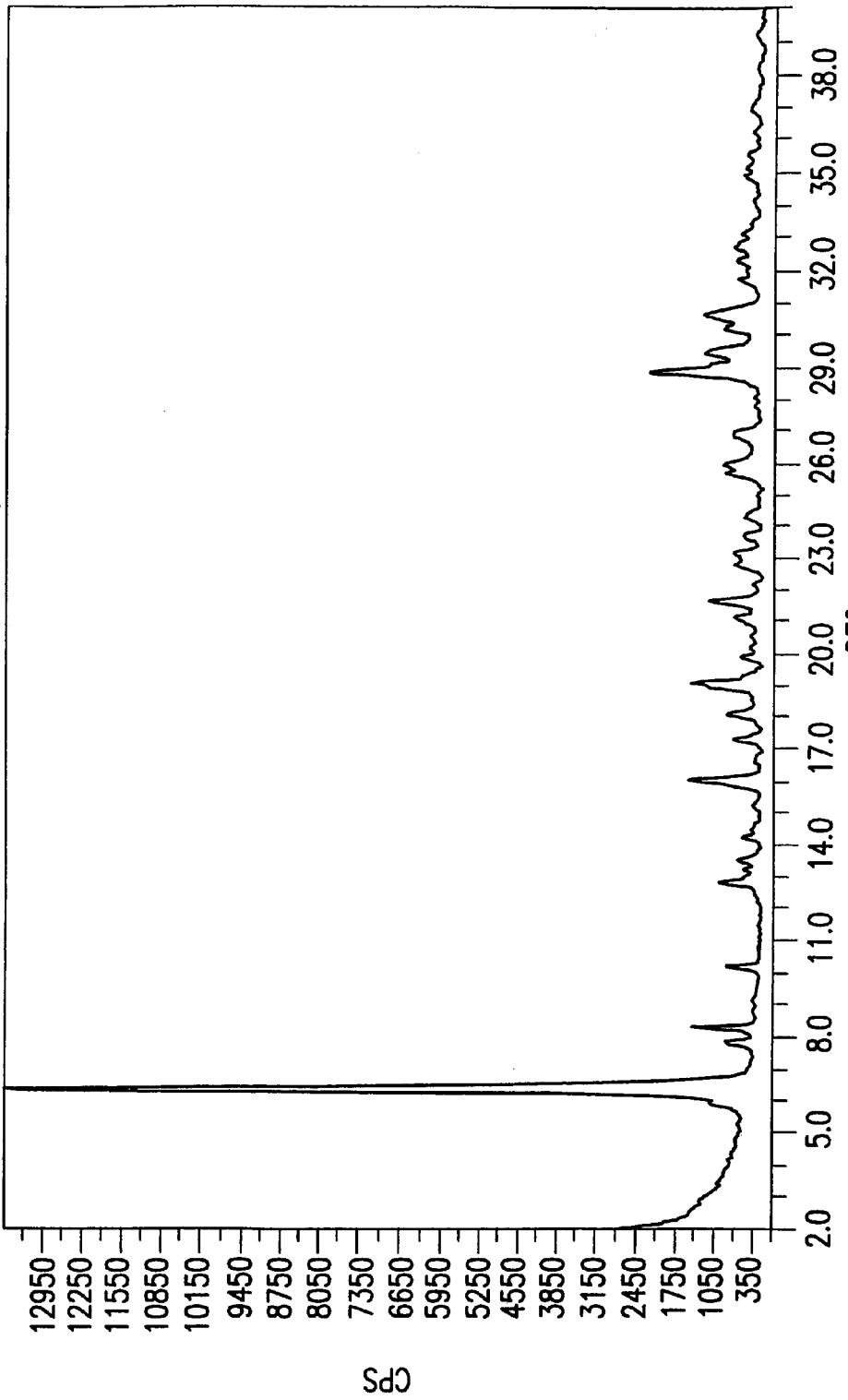
FIG. 20 is a representative PXRD pattern of zoledronate disodium Form XXVII.
Figure 21:
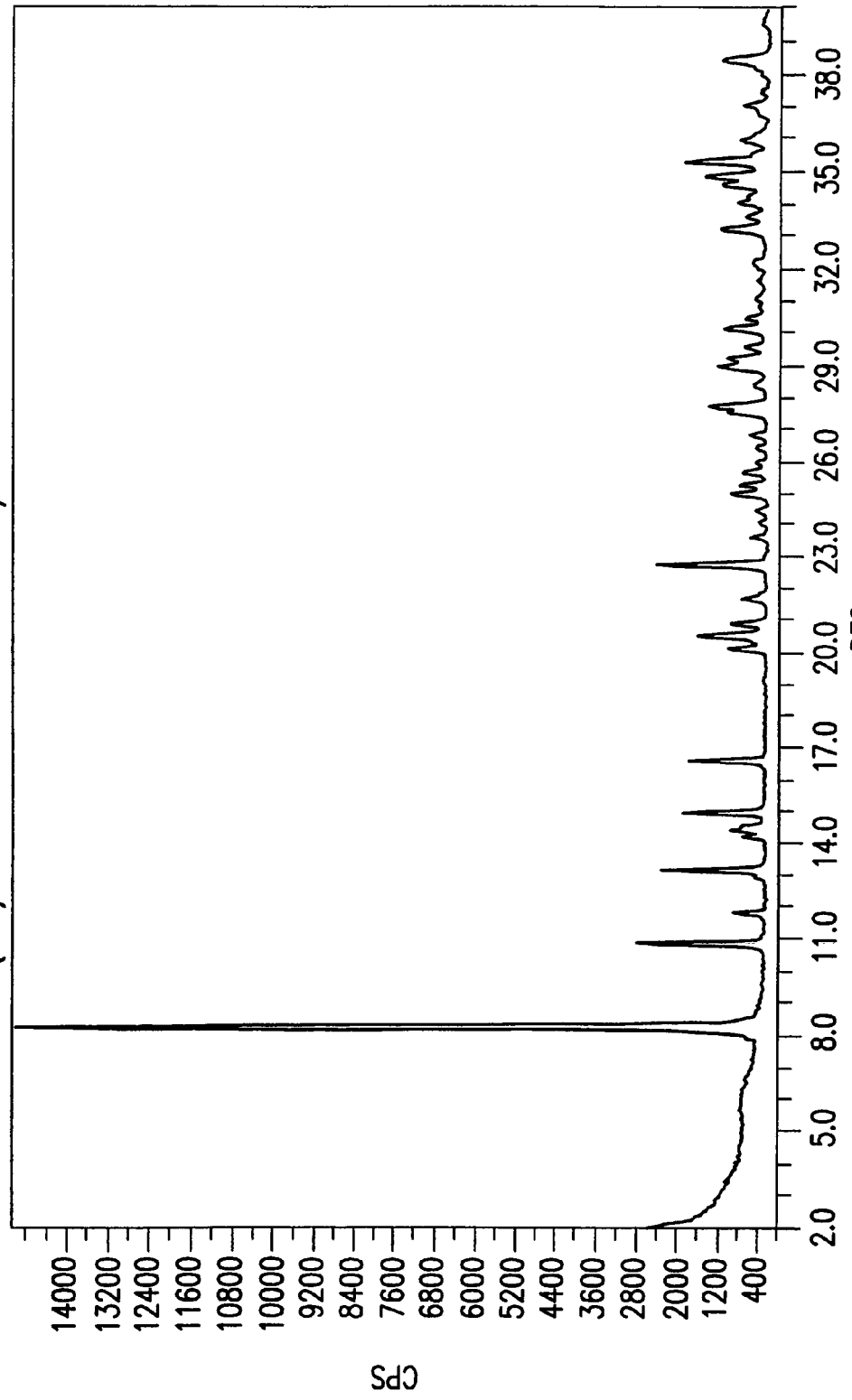
FIG. 21 is a representative PXRD pattern of zoledronate disodium Form IX.
Figure 22:
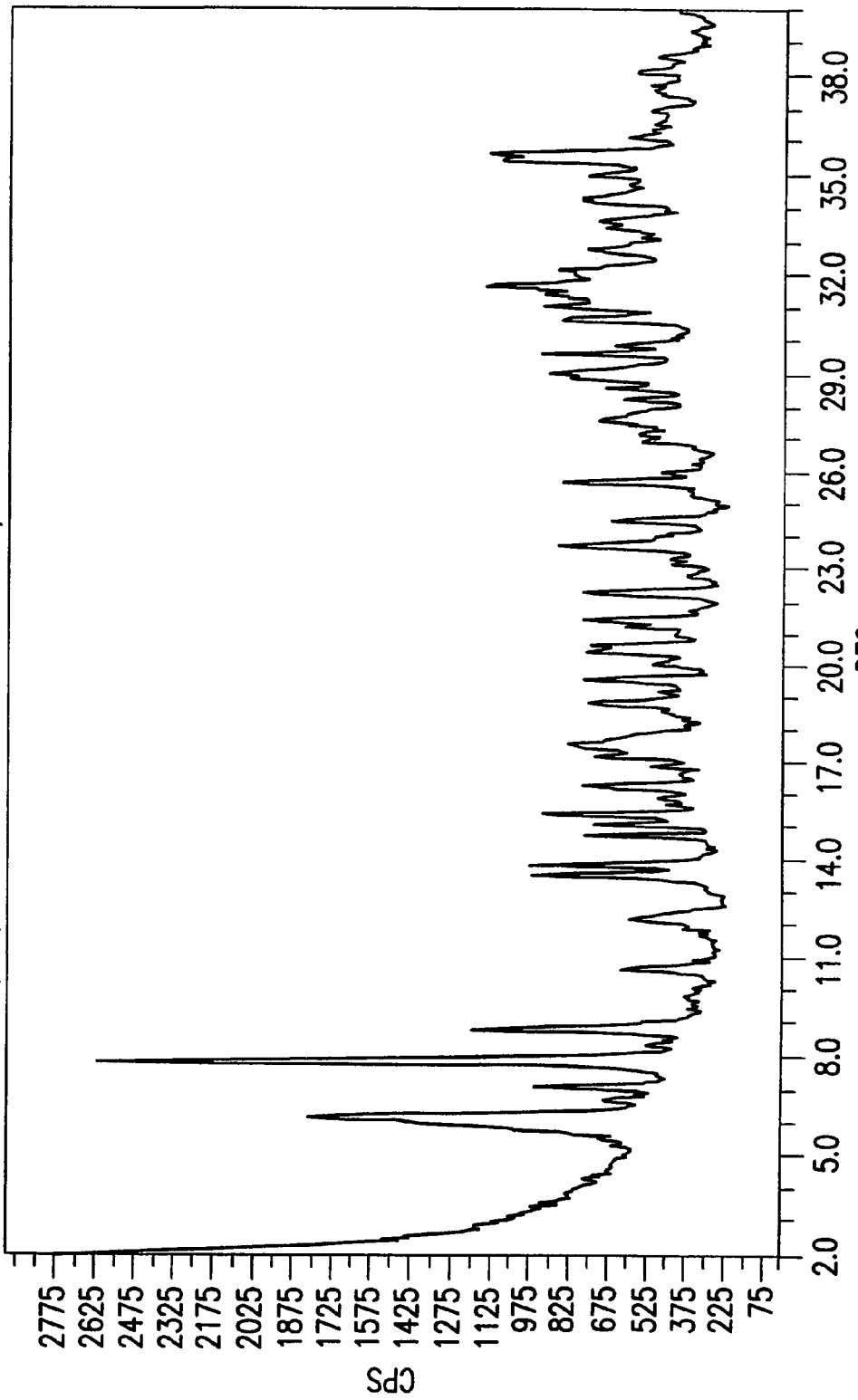
FIG. 22 is a representative PXRD pattern of zoledronate disodium Form XI.
Figure 23:
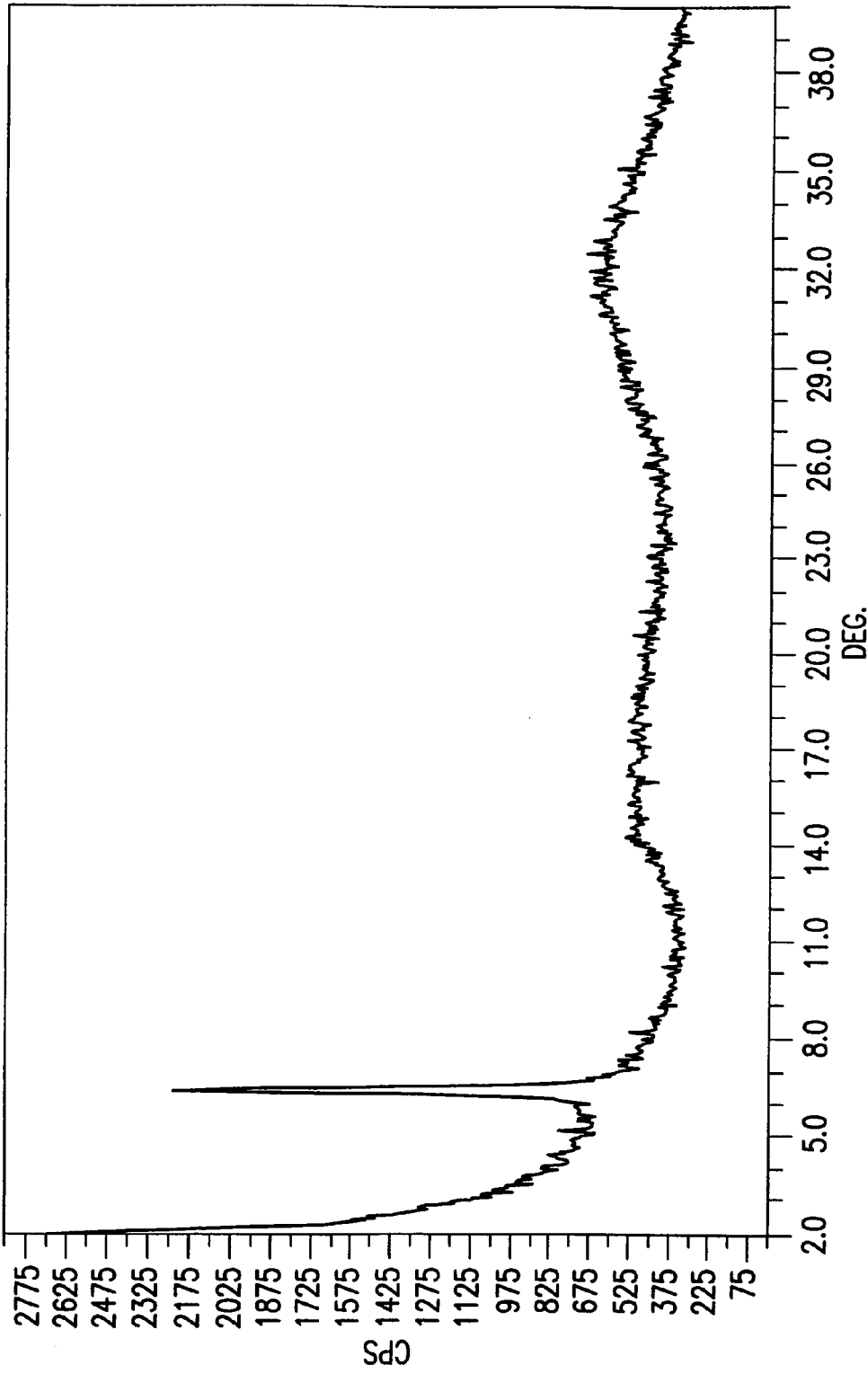
FIG. 23 is a representative PXRD pattern of zoledronate sodium amorphous.
Figure 24:
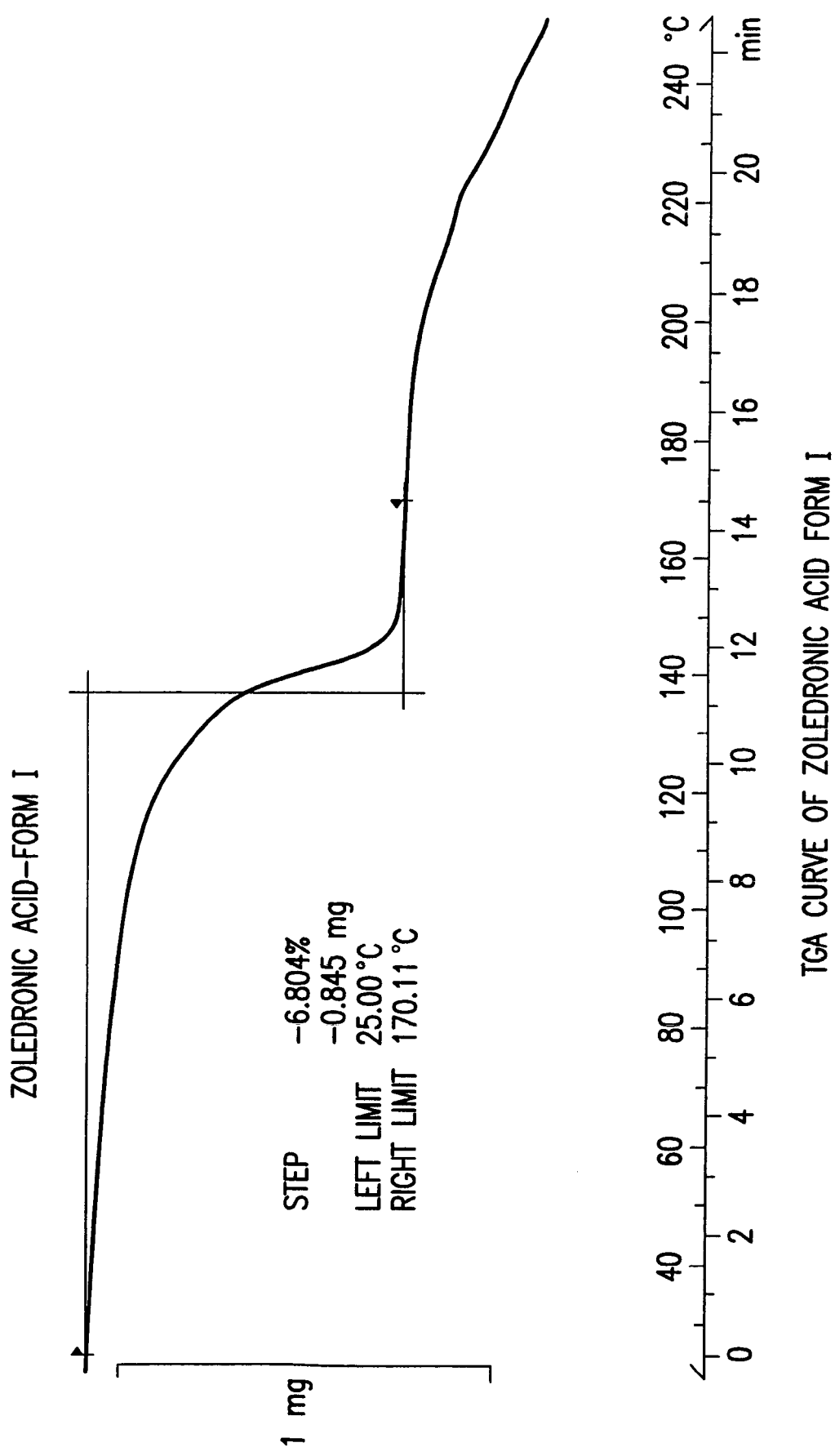
FIG. 24 is a representative TGA curve of zoledronic acid Form I.
Figure 25:
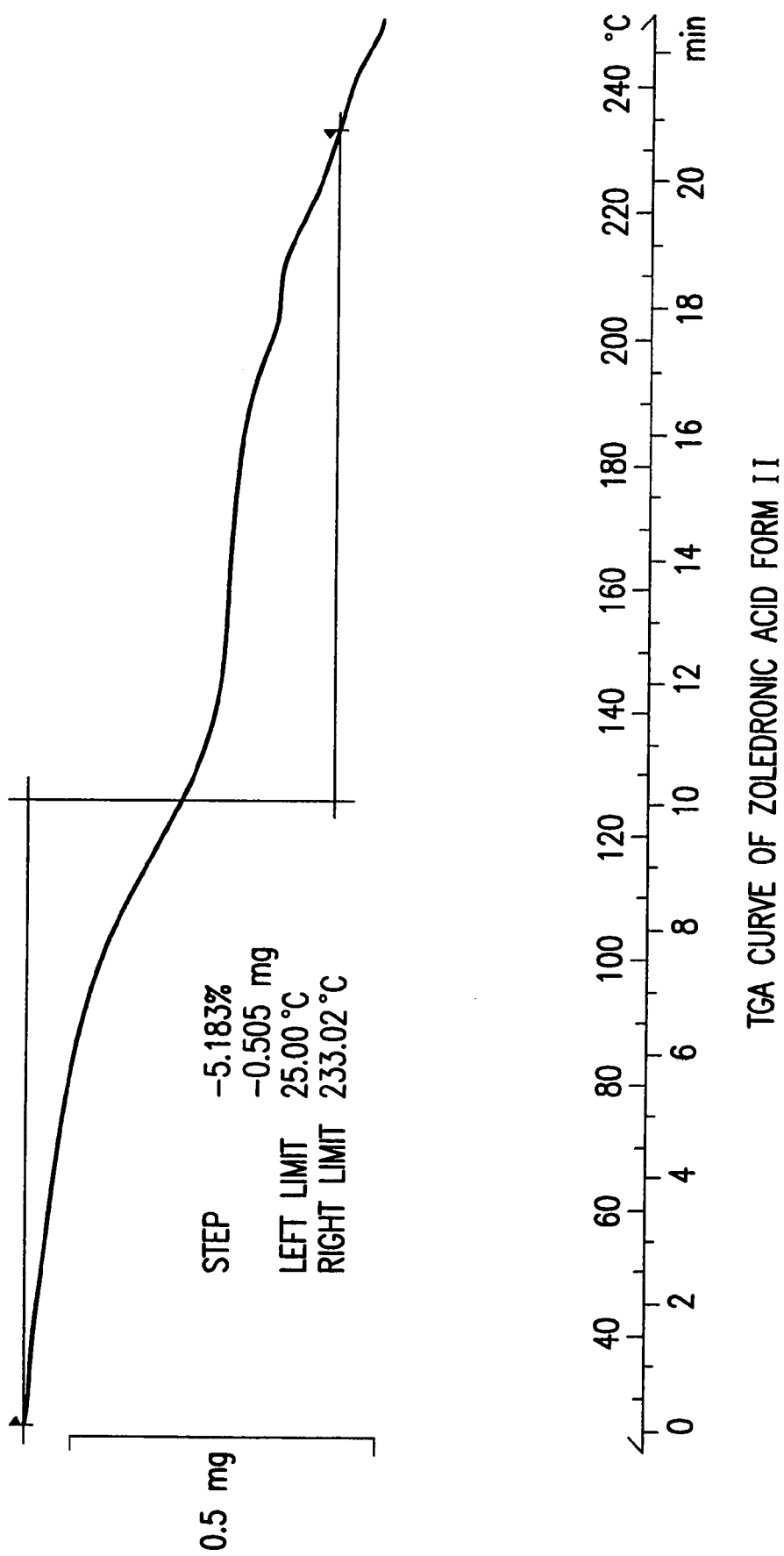
FIG. 25 is a representative TGA curve of zoledronic acid Form II.
Figure 26:
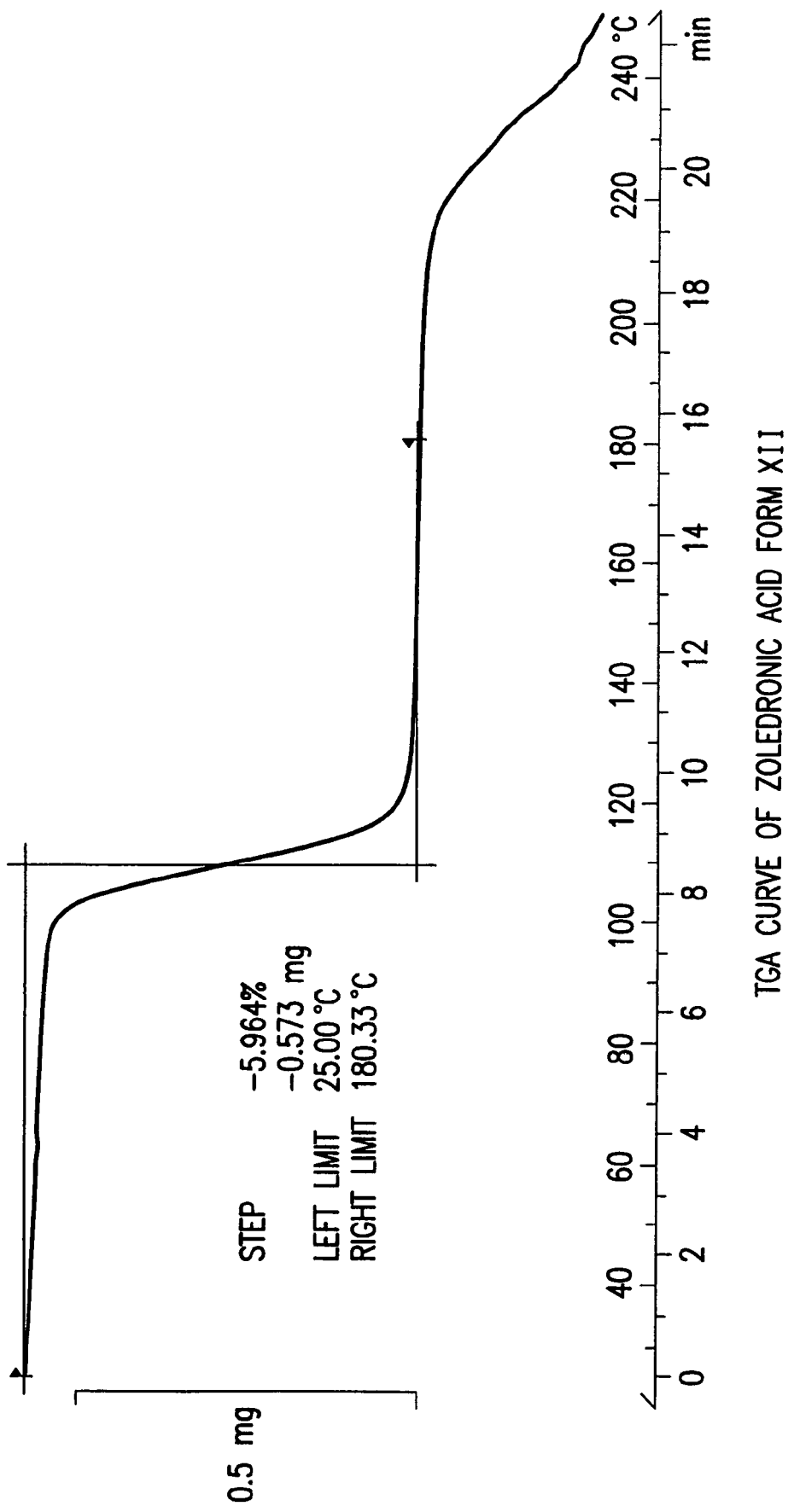
FIG. 26 is a representative TGA curve of zoledronic acid Form XII.
Figure 27:
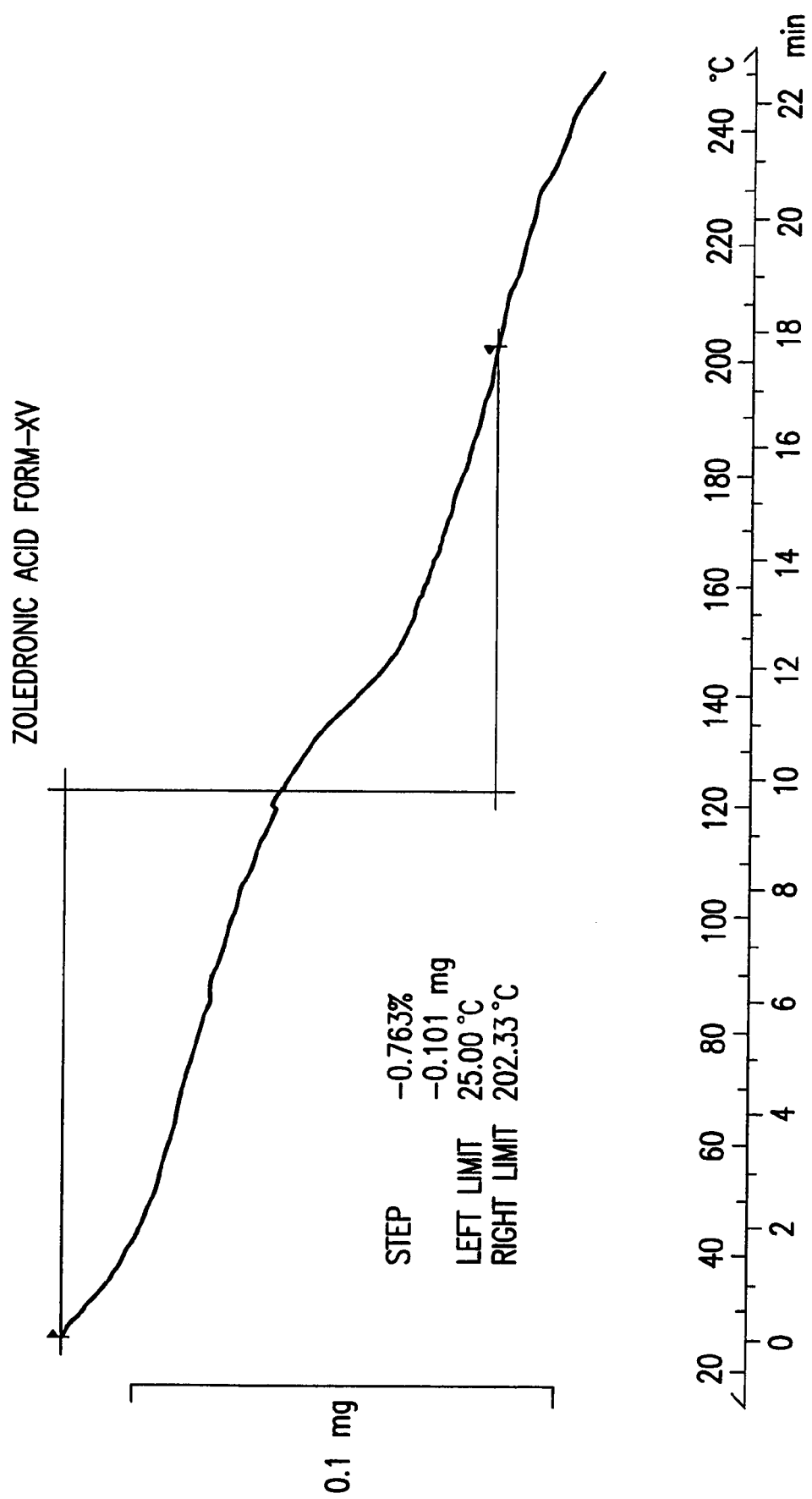
FIG. 27 is a representative TGA curve of zoledronic acid Form XV.
Figure 28:
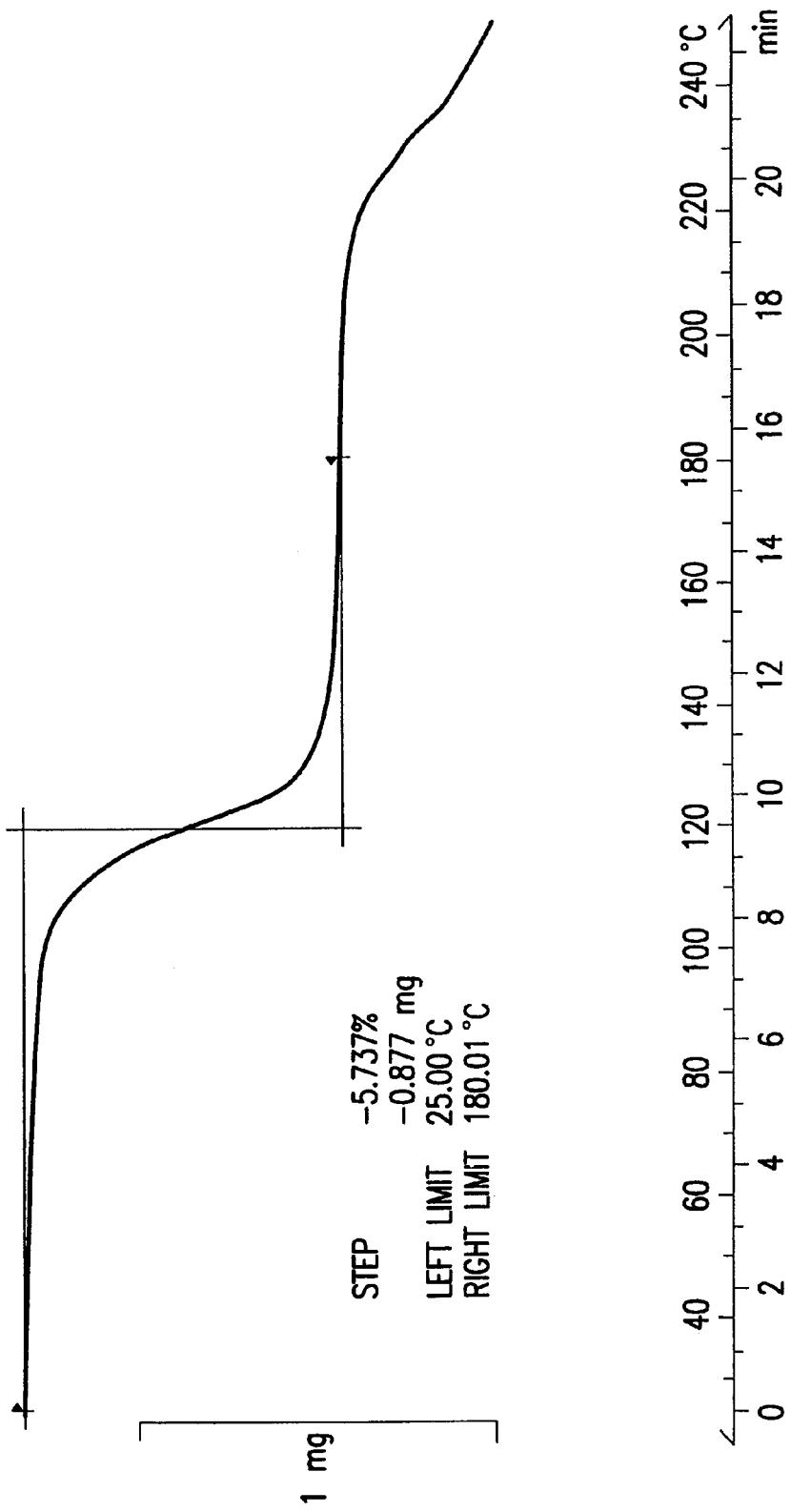
FIG. 28 is a representative TGA curve of zoledronic acid Form XVIII.
Figure 29:
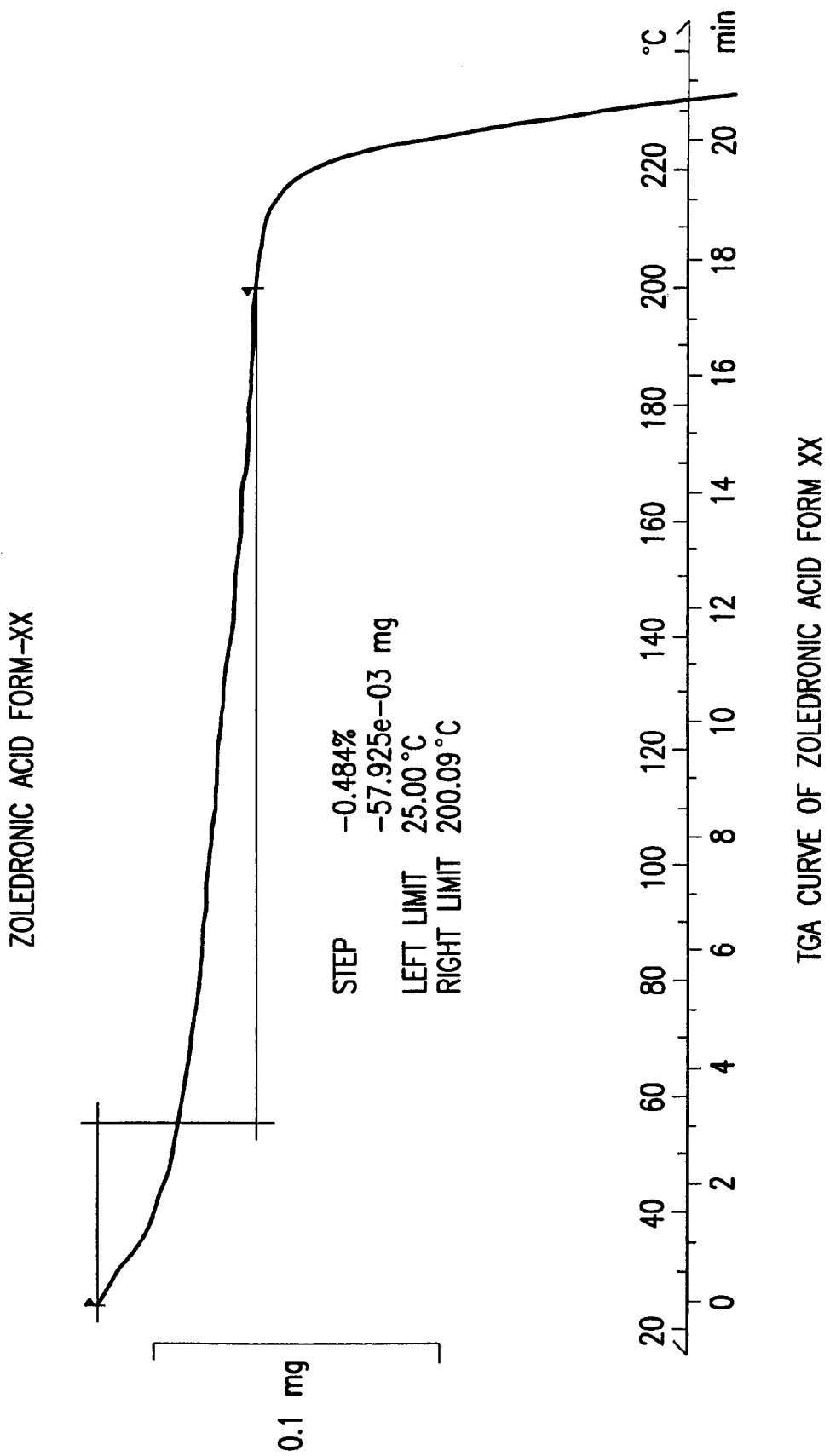
FIG. 29 is a representative TGA curve of zoledronic acid Form XX.
Figure 30:
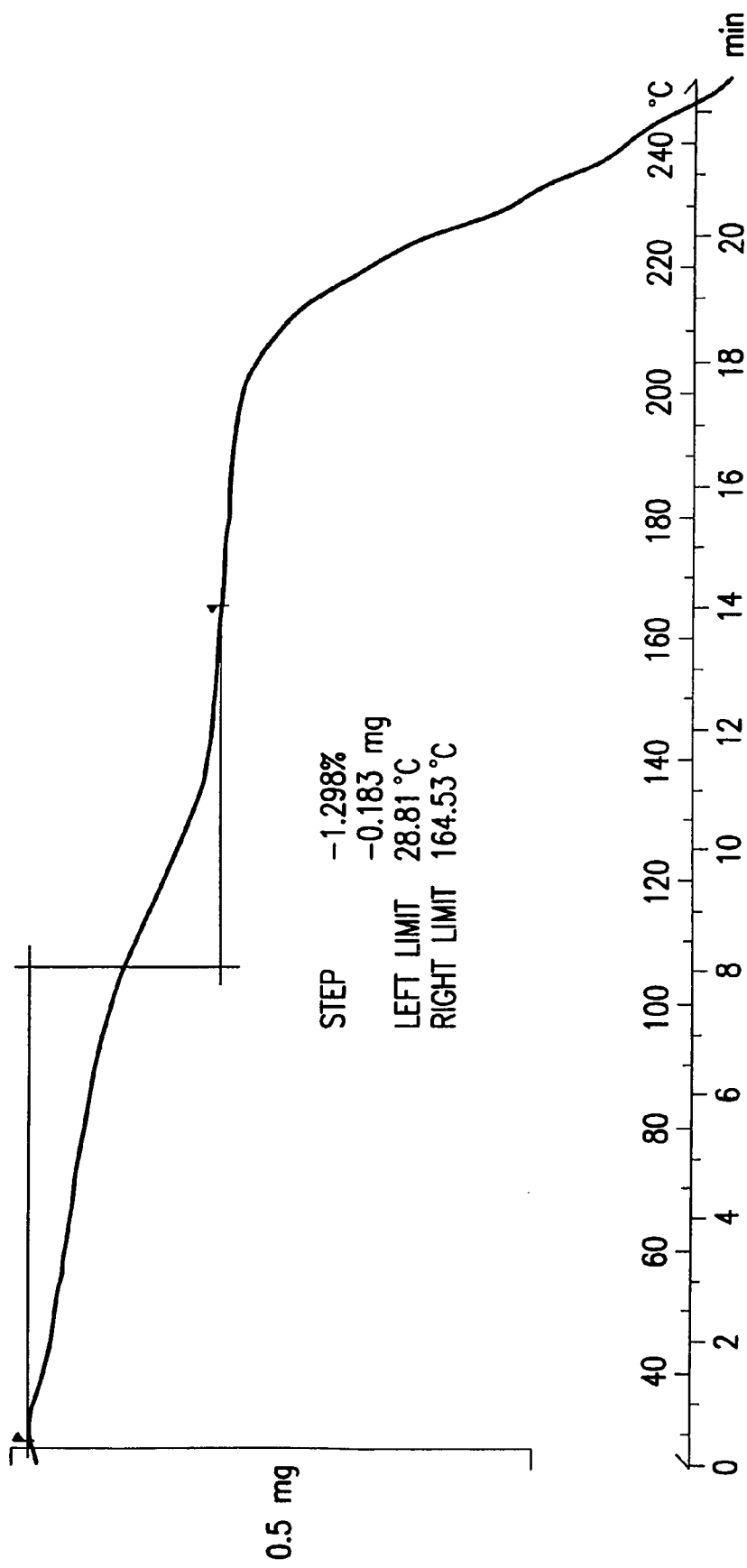
FIG. 30 is a representative TGA curve of zoledronic acid Form XXVI.
Figure 31:
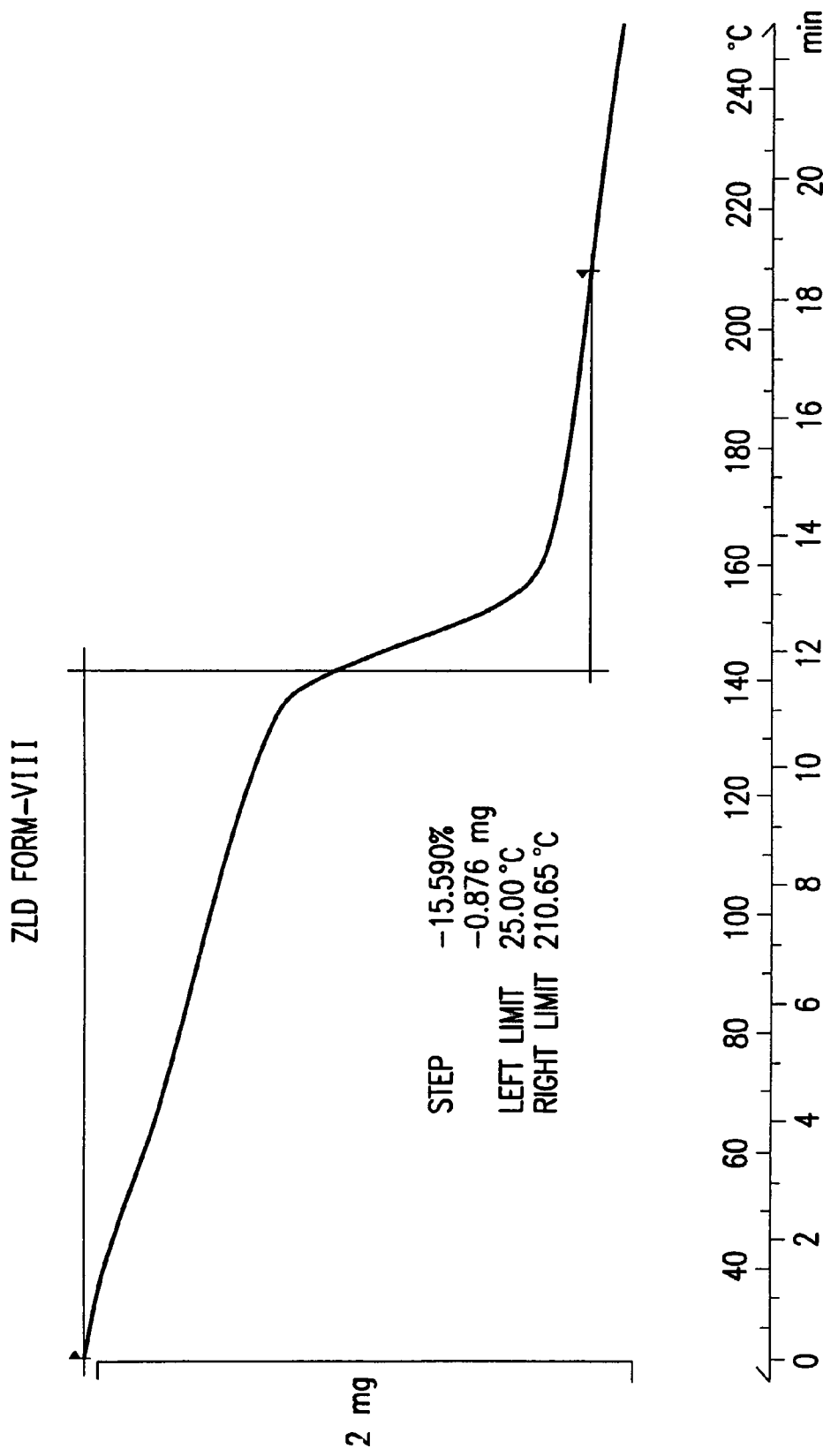
FIG. 31 is a representative TGA curve of zoledronate monosodium Form VIII.
Figure 32:
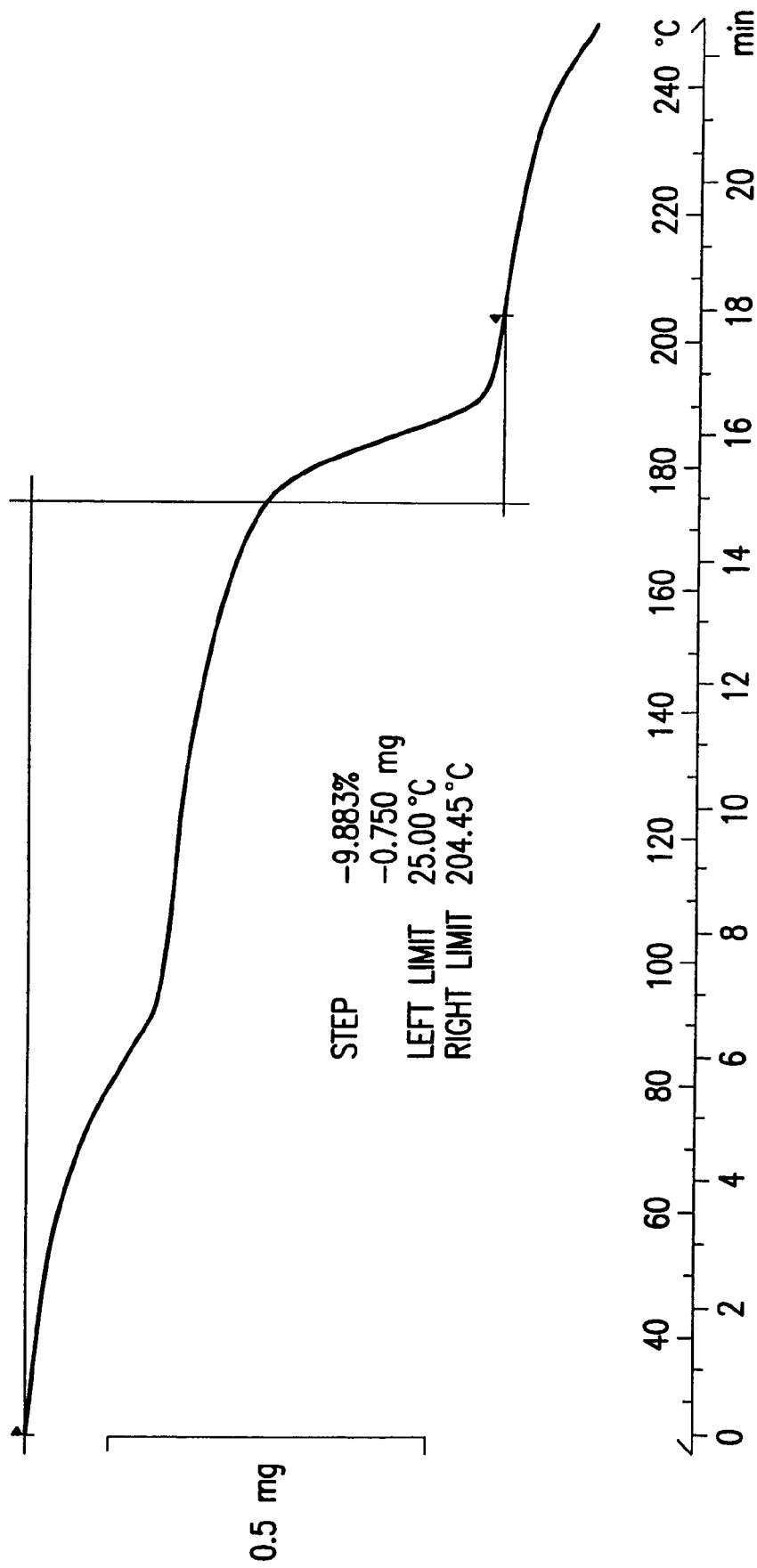
FIG. 32 is a representative TGA curve of zoledronate monosodium Form XVI.
Figure 33:
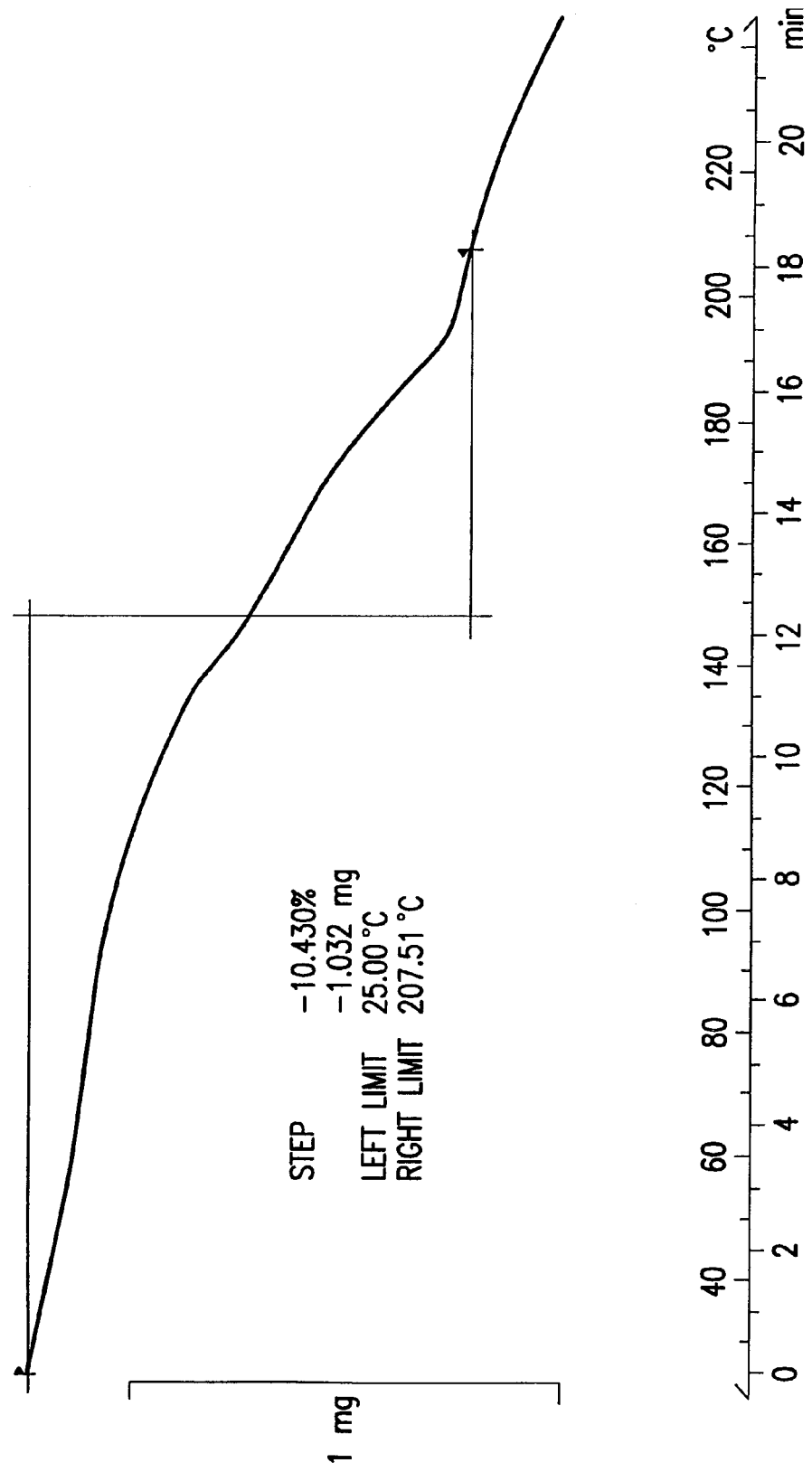
FIG. 33 is a representative TGA curve of zoledronate monosodium Form XVII.
Figure 34:
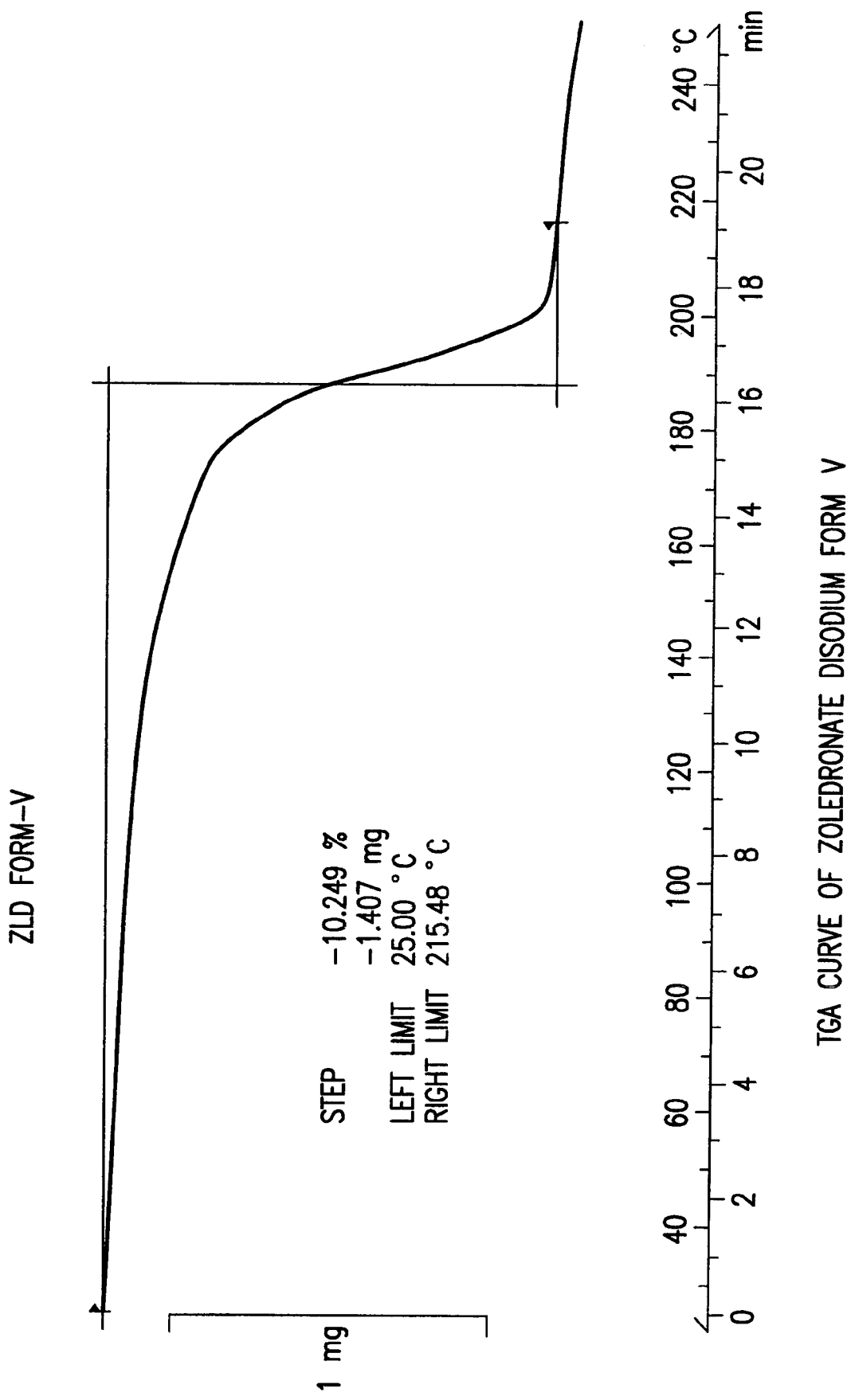
FIG. 34 is a representative TGA curve of zoledronate disodium Form V.
Figure 35:
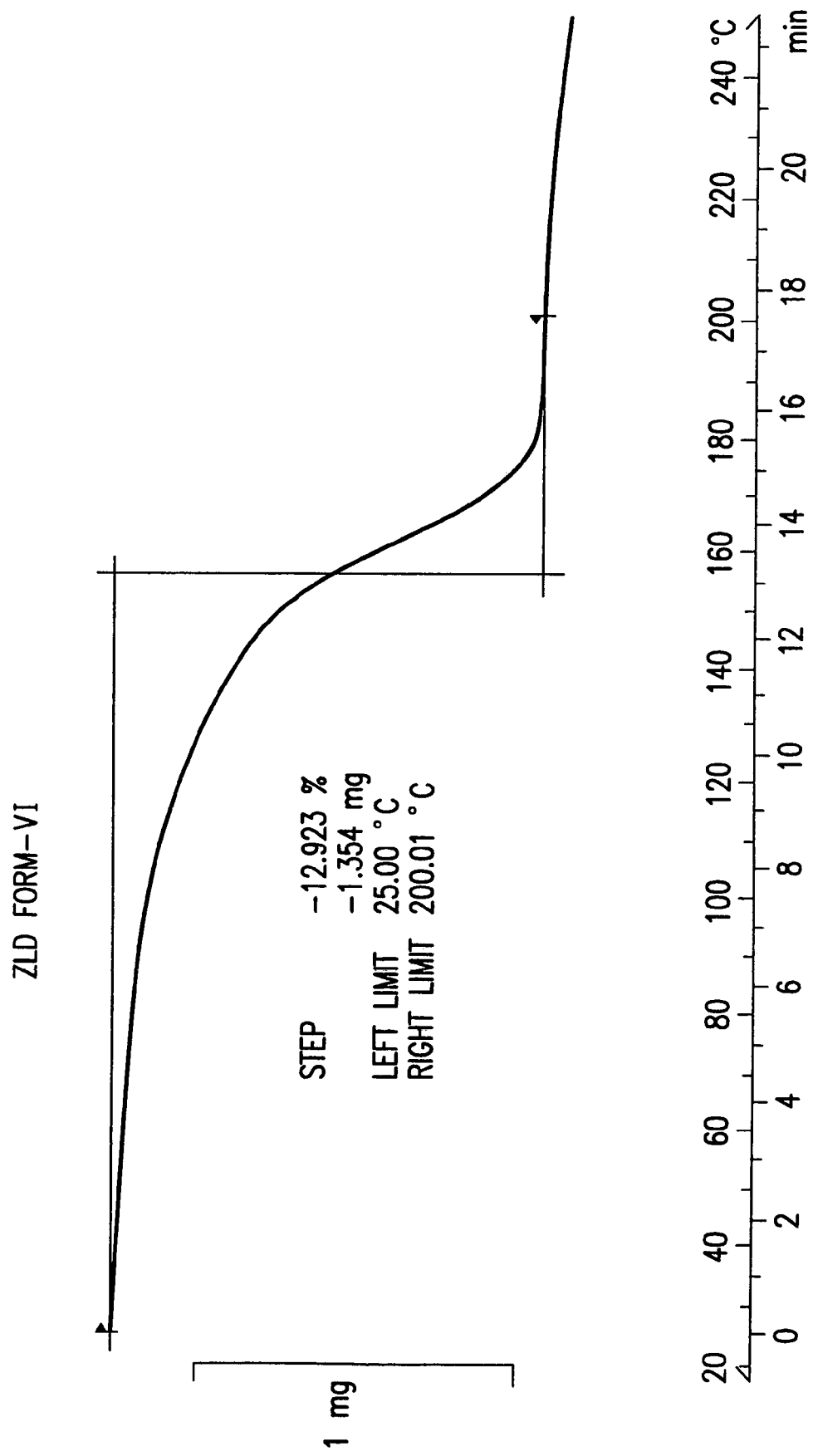
FIG. 35 is a representative TGA curve of zoledronate disodium Form VI.
Figure 36:
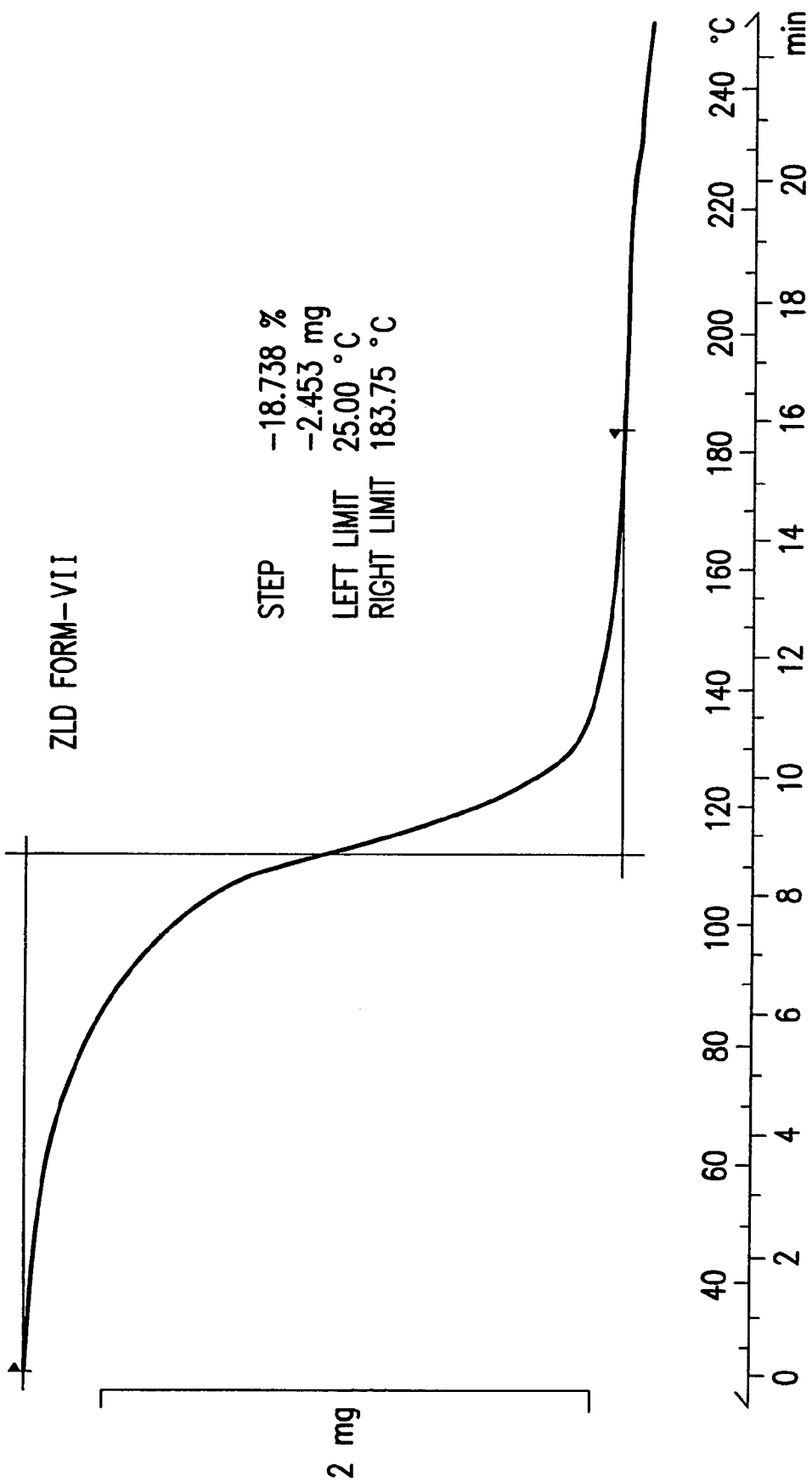
FIG. 36 is a representative TGA curve of zoledronate disodium Form VII.
Figure 37:
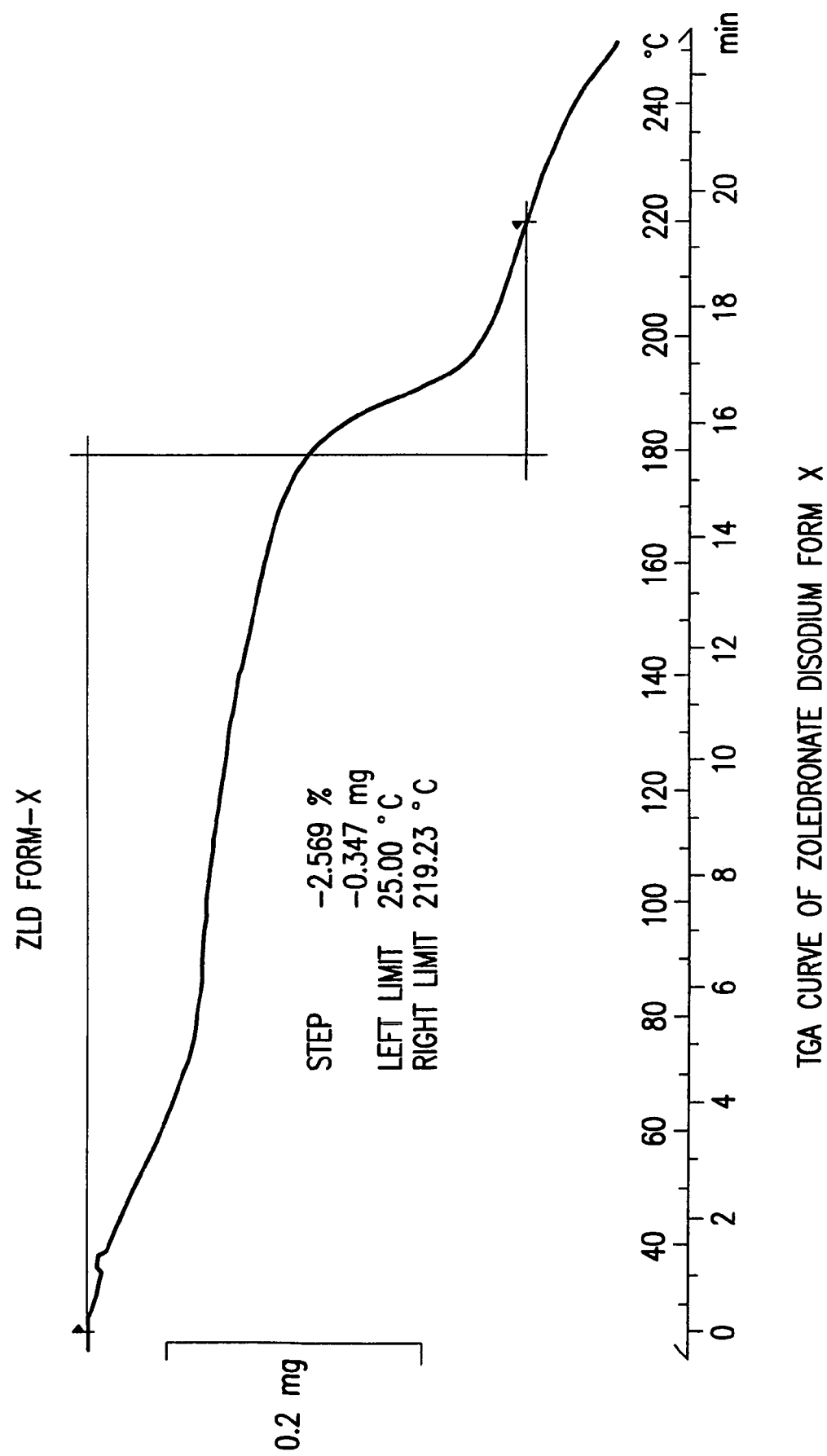
FIG. 37 is a representative TGA curve of zoledronate disodium Form X.
Figure 38:
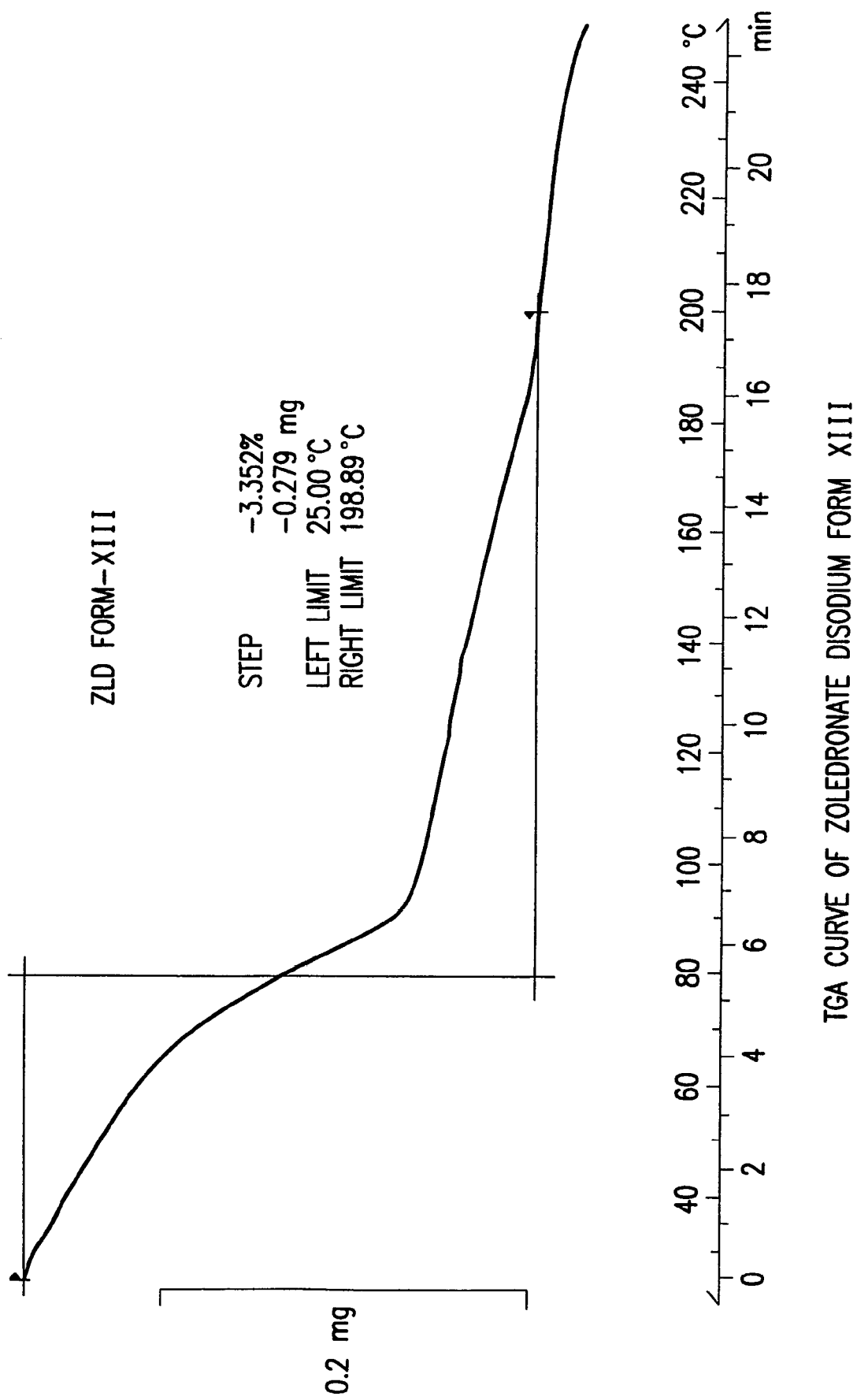
FIG. 38 is a representative TGA curve of zoledronate disodium Form XIII.
Figure 39:
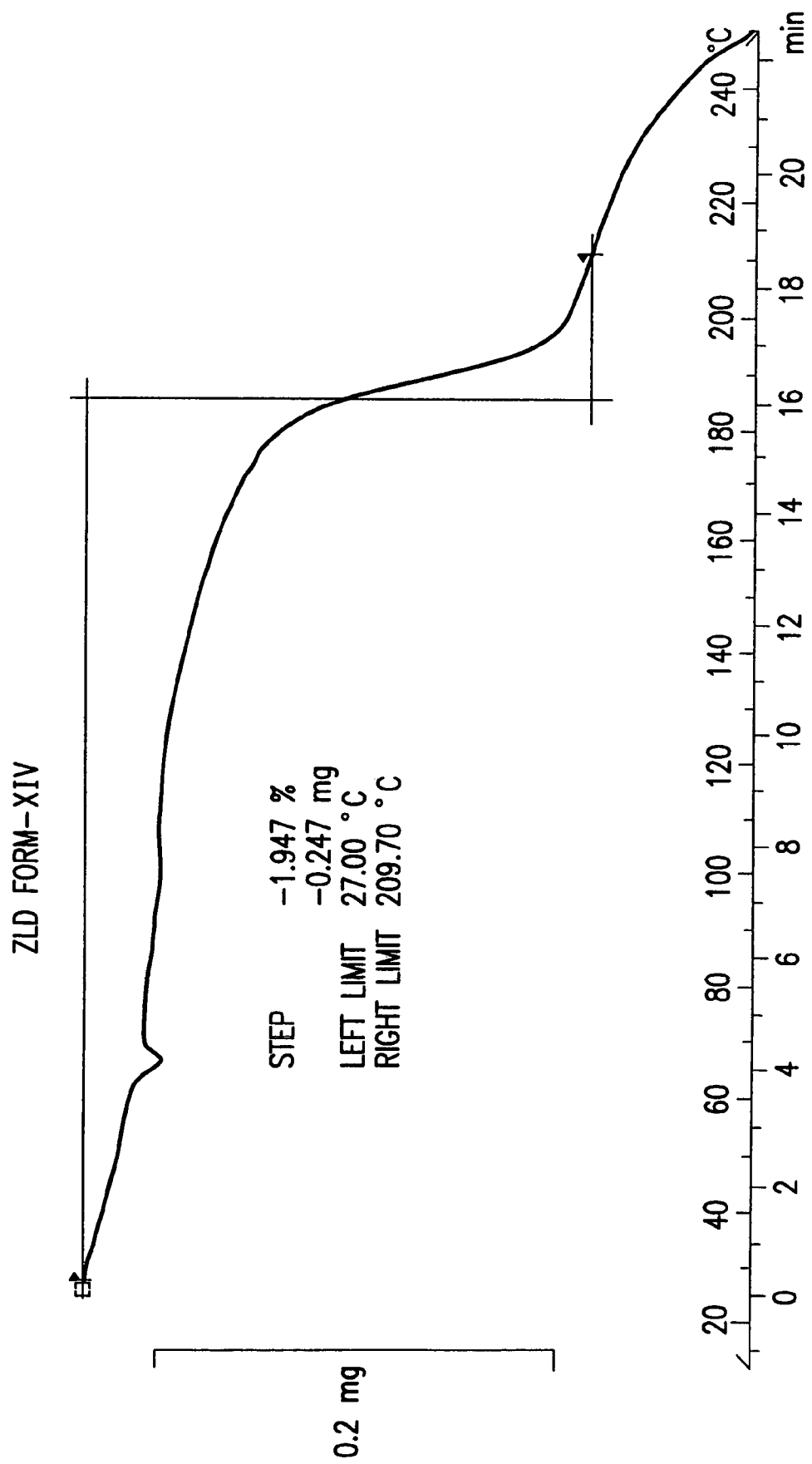
FIG. 39 is a representative TGA curve of zoledronate disodium Form XIV.
Figure 40:
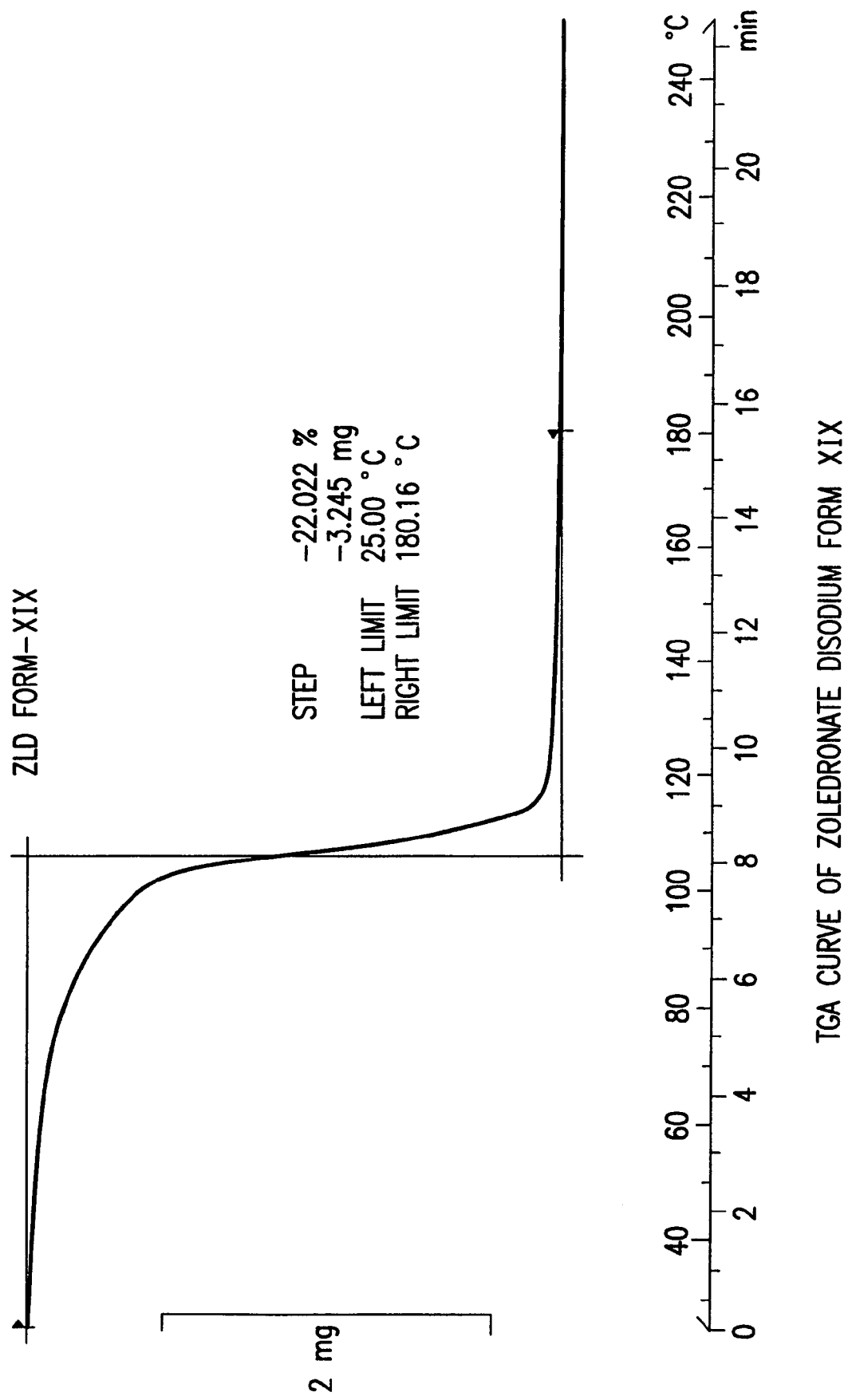
FIG. 40 is a representative TGA curve of zoledronate disodium Form XIX.
Figure 41:
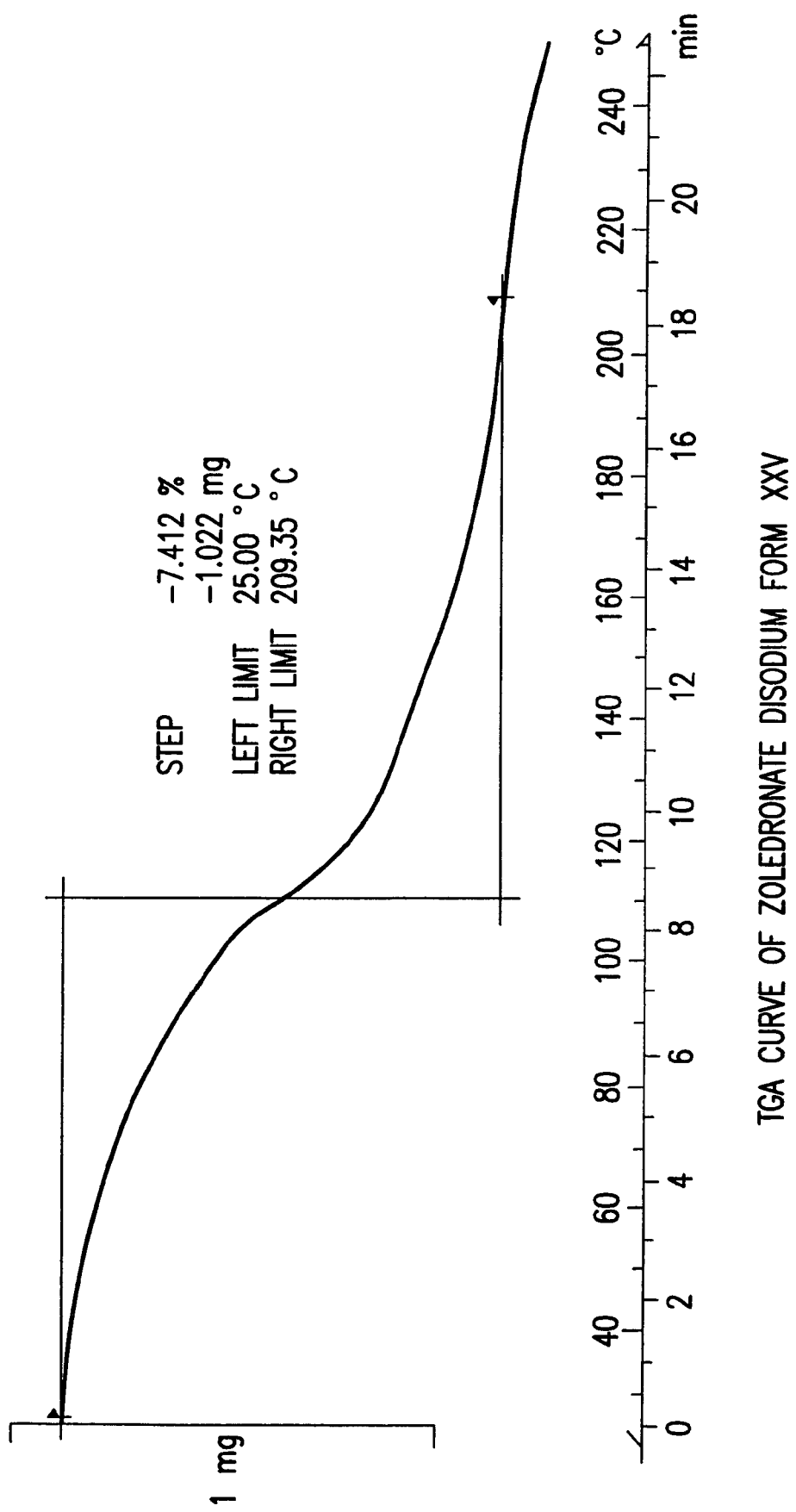
FIG. 41 is a representative TGA curve of zoledronate disodium Form XXV.
Figure 42:
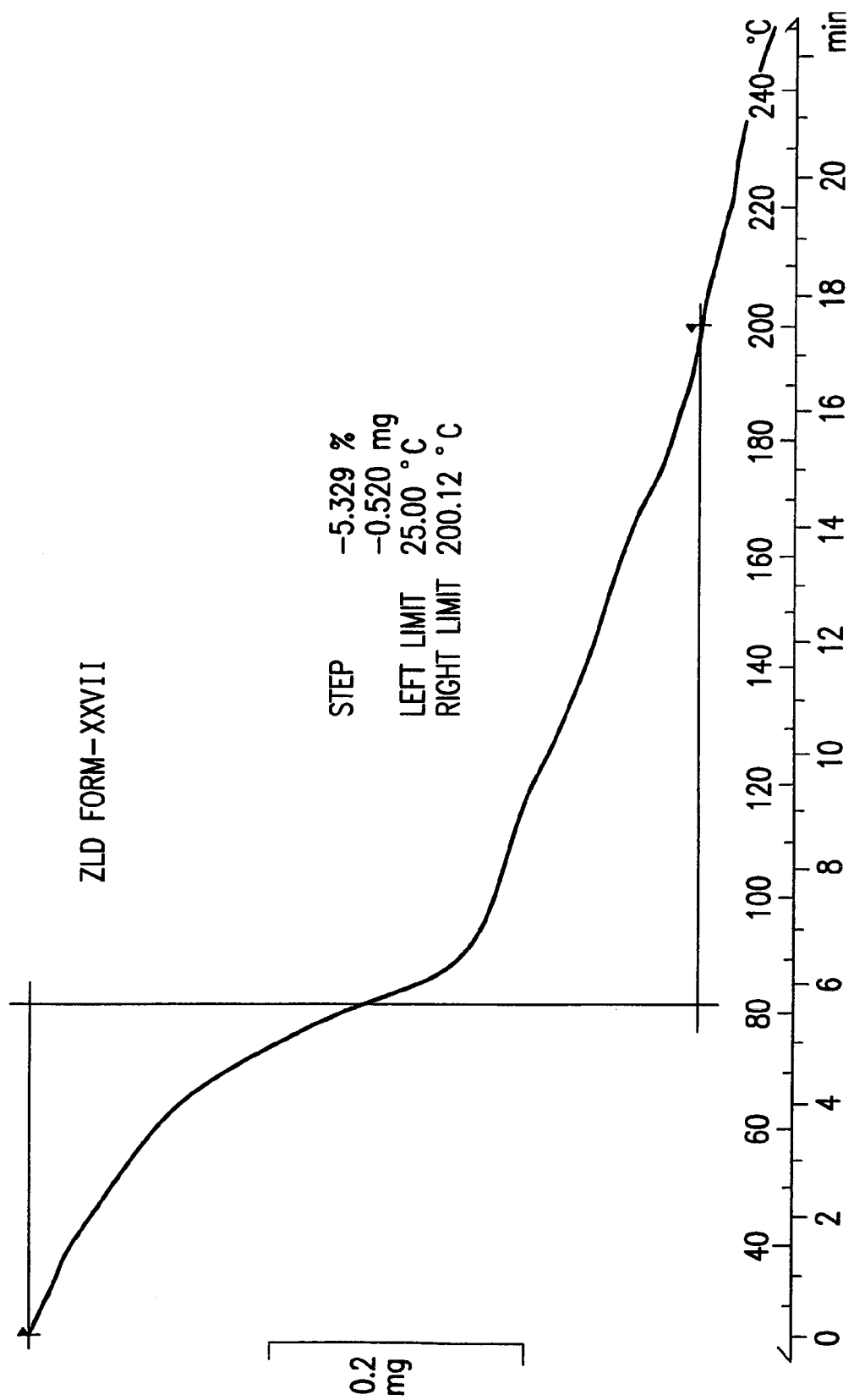
FIG. 42 is a representative TGA curve of zoledronate disodium Form XXVII.

In a seventh aspect, the invention provides a novel crystalline solid form of Zoledronic acid, denominated Form XXVI. Zoledronic acid Form XXVI can be identified by its PXRD pattern, a representative example of which is provided in FIG. 8. Particular characteristic peaks occur at 9.8°, 14.5°, 17.1°, 17.6°, and 18.3° 2θ±0.2° 2θ. Additional peaks occur at 18.8°, 19.7°, 21.4°, 25.7°, 26.6°, and 28.1° 2θ±0.2° 2θ. The TGA weight loss curve of Zoledronic acid form XXVI shows typically a LOD of about 1.3% (anhydrous) within the temperature range 25-220° C.

Zoledronic acid Form XXVI can be prepared by treating Zoledronic acid form I in 2-butanol, preferably at reflux temperature. The diluent/solid ratio being 15-25 volumes, preferably 10 volumes, for a duration of 5-20 hours, most preferably 10-16 hours.

Crystal Forms of Zoledronic Acid Sodium Salt

In addition, it was also discovered that Zoledronic acid sodium salt in a crystalline form could be obtained. Use of salts in drugs is very diffused, due to the improved physicochemical properties over the free acid or free base, mainly solubility or crystallinity properties. The crystalline state of a drug, in general, has an advantage over the amorphous state in that the physical (and chemical) properties are fully controlled and reproduced, and the capability of a material to crystallize in a solid form makes this material feasible for pharmaceutical uses. Hence, the novel crystalline Zoledronate sodium salt may have improved solubility. In addition, it was found that the sodium salts obtained have a purity of at least 99.9% area by HPLC.

Surprisingly, it was also discovered that Zoledronate sodium salt can crystallize in different crystal forms.

The level of sodium is measured by methods known in the art, like atomic absorption.

Zoledronate sodium can be found in a monosodium salt, disodium salt, trisodium salt, each of them in various hydration states. The Zoledronate monosodium salt has a sodium content in the range of 6-8% w/w. Zoledronate disodium has a sodium content in the range of 11-13% w/w, and Zoledronate trisodium has a sodium content in the range of 17-19% w/w.

The level of water in Zoledronate sodium is estimated by TGA (thermogravimetric analysis) weight loss. The Zoledronate sodium salt can be anhydrous (weight loss up to 2%), a hemihydrate (weight loss 3-4% w/w), a monohydrate (weight loss 5-6%), a sesquihydrate (weight loss 7-8%), a dihydrate (weight loss 9-12% w/w), a trihydrate (13-16% weight loss), or a tetrahydrate (weight loss 17-19% w/w).

In general, sodium salts of Zoledronic acid may be prepared by treating Zoledronic acid with a base, preferably NaOH, in organic solvents, like lower alcohols or DMF, and water in different proportions relative to the organic solvent. The reaction is preferably carried out at reflux temperature. In these procedures a solution of a base in a mixture of alcohol/water is added to a suspension of Zoledronic acid in an equivalent mixture of alcohol/water at reflux temperature. The volume ratio of diluent/Zoledronic acid is 6-14, preferably 10 volumes. The reaction mixture is stirred at reflux temperature for 10-20 hours, preferably 14-16 hours. The reaction mixture can be cooled to room temperature or less, and filtered, or filtered at higher temperatures.

Alternatively, sodium salts of Zoledronic acid may be prepared by dissolving Zoledronic acid in water, adding a base, preferably NaOH, and precipitating it by cooling, optionally with the aid of an organic solvent such as isopropyl alcohol.

Alternatively, sodium salts of Zoledronic acid may be recrystallized by treating the sodium salt of Zoledronic acid in water (20-30 volumes, preferably 25 volumes) at reflux temperature and then cooling the solution to less than room temperature to obtain a precipitate of ZLD-Na.

Zoledronate Monosodium Crystal Forms

Zoledronate monosodium can be found in crystal Form VIII, characterized by typical PXRD peaks at 8.2°, 15.5°, 18.6°, 23.6°, and 26.8° 2θ±0.2° 2θ, and additional peaks at 11.8°, 17.6°, 20.1°, 24.7°, 25.0°, 28.4°, 31.7°, 32.8° 2θ±0.2° 2θ. The TGA of form VIII shows a weight loss of 15-16% (trihydrate) within the temperature range 25-220° C.

Zoledronate monosodium can be found in crystal form XVI, characterized by typical XRD peaks at 7.3°, 8.8°, 14.7°, 21.8°, and 29.6° 2θ±0.2° 2θ, and additional peaks at 13.8°, 16.8°, 20.4°, 21.4°, 24.4°, 25.6°, 27.5°, 28.2°, and 31.7° 2θ±0.2° 2θ. The TGA curve of form XVI shows a weight loss of 9-10% (dihydrate) within the temperature range 25-220° C.

Zoledronate monosodium can be found in crystal form XVII, characterized by typical XRD peaks at 8.2°, 9.0°, 14.5°, 21.4°, 24.5°, 29.2° 2θ±0.2° 2θ, and additional peaks at 13.9°, 15.5°, 16.8°, 18.6°, 22.3°, 23.6°, 26.7°, 27.7°, and 32.3° 2θ±0.2° 2θ. The TGA of form XVII shows a weight loss of about 10% (dihydrate) within the temperature range 25-220° C.

Zoledronate monosodium form VIII may be prepared by dissolving Zoledronic acid in water, adding NaOH in pellets or in aqueous solution (40%). IPA may be added to improve the yield of crystallization. This solution is cooled to get form VIII.

Zoledronate monosodium form VIII may be also obtained by treating Zoledronic acid, preferably form I, and sodium hydroxide (ratio of acid/base 1:1) in water/ethanol 80%:20% v/v, water/methanol 80%:20% v/v, water/isopropanol 80%:20% v/v or 60%:40% v/v.

Zoledronate monosodium form XVI may be obtained by treating Zoledronic acid, preferably form I, and sodium hydroxide (ratio of acid/base 1:1) in water/ethanol 50%:50% v/v or water/isopropanol 50%:50% v/v, or water/methanol 50%:50% v/v.

Zoledronate monosodium form XVII may be obtained by dissolving Zoledronic acid in water, adding NaOH in aqueous solution (29%) drop-wise (ratio of acid/base 1:0.7) 2θ±0.2° 2θ, and additional peaks at 18.0°, 18.9°, 19.7°, 22.7°, 25.0°, 26.7°, 30.9°, and 34.5° 2θ±0.2° 2θ. The TGA curve of form V shows a weight loss of about 10-11% (dihydrate) within the temperature range 25° to 220° C.

Zoledronate disodium form V may be prepared by treating Zoledronic acid, preferably form XII, and sodium hydroxide (ratio of acid/base 1:1.1) in water/ethanol ratios between 20%-50% v/v water in ethanol, water/methanol ratios between 40%-50% v/v water in methanol, water/IPA ratios between 40%-50% v/v water in IPA.

Zoledronate disodium form V may also be prepared by treating Zoledronic acid, preferably form I, and sodium hydroxide (ratio of acid/base 1:2) in water/ethanol ratios between 20%-50% v/v water in ethanol, water/methanol 50%:50% v/v water in methanol, water/isopropanol ratios between 20%-50% v/v water in IPA.

Zoledronate disodium form V may also be prepared by treating Zoledronic acid, preferably form XII, and sodium hydroxide (ratio of acid/base 1:1.1) in water/ethanol ratios between 20%-50% v/v water in ethanol, water/methanol ratios between 40%-50% v/v water in methanol, water/IPA ratios between 40%-50% v/v water in IPA.

Zoledronate disodium can be found in form VI, characterized by typical peaks at 7.2°, 13.3°, 13.7°, 14.5°, 21.7° 2θ±0.2° 2θ, and additional peaks at 8.2°, 16.6°, 16.9°, 17.3°, 25.9°, 26.6°, 30.7°, 31.9°, 32.9° 2θ±0.2° 2θ. The TGA curve of form VI shows a weight loss of 13-16% (trihydrate) within the temperature range 25-220° C.

Zoledronate disodium form VI may be prepared by treating Zoledronic acid, preferably form XII, and sodium hydroxide (ratio of acid/base 1:1.1) in water/ethanol or water/methanol 60% v/v water in ethanol or methanol, or water/isopropanol 80% v/v water in IPA.

Zoledronate disodium form VI may also be obtained also by recrystallizing Zoledronate disodium, preferably form XIX, in water.

Zoledronate disodium can be found in form VII, characterized by typical peaks at 6.2°, 11.6°, 12.6°, and 13.7° 2θ±0.2° 2θ, and additional peaks at 22.0°, 23.2°, 26.4°, 27.1°, 28.6°, 28.8°, 34.2° 2θ±0.2° 2θ. The TGA curve of form VII shows a weight loss of 17-19% within the temperature range 25-220° C. (tetrahydrate). Less crystalline form VII is found with water content of 7-10% within the temperature range 25-220° C.

Zoledronate sodium form VII may be obtained by dissolving Zoledronic acid in water, adding a base, preferably NaOH (aqueous solution or pearls) until the pH of 5.5-7.5, preferably 5.7-7.0. The solution is cooled and optionally an organic solvent (preferably isopropanol) is added. Optionally the solution may be concentrated to obtain the solid material. The mixture may be further stirred for a period of 1-5 hours, preferably 2 hours.

Zoledronate disodium form VII may be also prepared by treating Zoledronic acid, preferably form XII, and sodium hydroxide (ratio of acid/base 1:1.1) in water/ethanol or water/methanol or water/isopropanol 80%:20% v/v of water in the alcohol.

Zoledronate disodium form VII may be also prepared by treating Zoledronic acid, preferably form XII, and sodium hydroxide (ratio of acid/base 1:1.1) in water/isopropanol 60%:40% v/v water in IPA.

Zoledronate disodium form VII may be also prepared by treating Zoledronic acid, preferably form I, and sodium hydroxide (ratio of acid/base 1:2) in water/ethanol 80%:20% v/v water in ethanol.

Zoledronate Disodium Crystal Forms

Zoledronate disodium can be found in form V, characterized by typical peaks at 11.3°, 14.8°, 15.5°, 17.4°, 19.9°

Zoledronate disodium can be found in form X, characterized by typical peaks at 6.7°, 14.4°, 18.2°, 20.4°, and 20.7°

2θ±0.2° 2θ, and additional peaks at 8.8°, 13.7°, 17.0°, 19.8°, 21.3°, 24.4°, 27.5°, 27.9°, 30.9°, and 33.4° 2θ±0.2° 2θ. The TGA curve of form X shows a weight loss of about 3% (hemihydrate) within the temperature range 25° to 220° C.

Zoledronate disodium form X may be obtained by treating Zoledronic acid, preferably form XII, and sodium hydroxide (ratio of acid/base 1:1.1) in water/isopropanol 20%:80% v/v water in IPA.

Zoledronate disodium can be found in form XIII, characterized by typical peaks at 6.5°, 13.0°, 16.1°, 17.2°, and 30.7° 2θ±0.2° 2θ, and additional peaks at 10.2°, 19.0°, 20.0°, 20.6°, 22.3°, 27.4°, 28.6°, 28.9°, 34.8° 2θ±0.2° 2θ. The TGA curve of form XIII shows a weight loss of about 3% (hemihydrate) within the temperature range 25-220° C.

Zoledronate disodium form XIII may be obtained by treating Zoledronic acid, preferably form I, and sodium hydroxide (ratio of acid/base 1:2) in water/ethanol 5%:95% v/v water in ethanol.

Zoledronate disodium can be found in form XIV, characterized by typical peaks at 6.6°, 19.9°, 28.5°, 34.8° 2θ±0.2° 2θ, and additional peaks at 13.0°, 15.1°, 17.1°, 20.5°, 27.7°, 29.6°, 30.7°, 33.5° 2θ±0.2° 2θ. The TGA curve of form XIV shows a weight loss of 1-2% (anhydrous) within the temperature range 25-220° C.

Zoledronate disodium form XIV may be obtained by treating Zoledronic acid, preferably form I, and sodium hydroxide (ratio of acid/base 1:2) in water/methanol 20%:80% v/v water in methanol.

Zoledronate disodium form XIV may be also obtained by treating Zoledronic acid, preferably form XII, and sodium hydroxide (ratio of acid/base 1:1) in water/DMF 20%:80% v/v water in DMF.

Zoledronate disodium can be found in form XIX, characterized by typical X-Ray peaks at 11.6°, 12.5°, 13.7°, 22.0°, 23.1 ° 2θ±0.2° 2θ, and additional peaks at 6.2°, 14.3°, 15.3°, 16.0°, 18.5°, 24.3°, and 28.6° 2θ±0.2° 2θ. The TGA curve of form XIX shows a weight loss of about 22% (pentahydrate) within the temperature range 25° to 220° C.

Zoledronate disodium form XIX may be obtained by treating Zoledronate disodium, preferably form VII, in water and precipitating the material, preferably by cooling.

Zoledronate disodium form XIX may be also obtained by dissolving Zoledronic acid in water, adding a base, preferably NaOH (aqueous solution or pearls) (ratio of acid/base 1:2), in reflux.

Zoledronate disodium can be found in form XXV, characterized by typical peaks at 7.4°, 13.7°, 17.6°, and 21.9° 2θ±0.2° 2θ, and additional peaks at 6.3°, 9.5°, 12.6°, 14.6°, 26.2°, 27.1°, and 28.6° 2θ±0.2° 2θ. The TGA curve of form XXV shows a weight loss of 7 to 8% (sesquihydrate) within the temperature range of 25° to 220° C.

Zoledronate disodium form XXV may be obtained by treating Zoledronic acid, preferably form I, and sodium hydroxide (ratio of acid/base 1:2) in water/methanol 80%:20% v/v water in methanol.

Zoledronate disodium can be found in form XXVII, characterized by typical peaks at 6.4°, 8.2°, 16.0°, 17.4°, 19.0°, 28.8° 2θ±0.2° 2θ, and additional peaks at 7.7°, 10.2°, 17.2°, 18.1°, 21.6°, 25.7°, 25.9° 2θ±0.2° 2θ. The TGA curve of form XXVII shows a weight loss of about 5-6% (monohydrate) within the temperature range 25-220° C.

Zoledronate disodium form XXVII may be prepared by treating Zoledronic acid, preferably form I, and sodium hydroxide (ratio of acid/base 1:2) in water/methanol 5%:95% v/v water in methanol and by treating Zoledronic acid, preferably form XII, and sodium hydroxide (ratio of acid/base 1:1) in water/methanol 20%:80% v/v water in methanol.

Zoledronate Trisodium Crystal Forms

Zoledronate trisodium can be found in form IX, characterized by typical peaks at 8.3°, 10.9°, 15.0°, 16.6°, and 22.8° 2θ±0.2° 2θ, and additional peaks at 13.1°, 20.2°, 20.6°, 20.9°, 25.0°, 27.8°, and 29.0° 2θ±0.2° 2θ. The TGA curve of form IX shows a weight loss of about 13-14% (trihydrate) within the temperature range 25-220° C.

Zoledronate trisodium form IX may be prepared by treating Zoledronic acid, preferably form XII, and sodium hydroxide (ratio of acid/base 1:2.1) in water/ethanol or water/methanol or water/isopropanol in ratios between 20%-80% v/v of water in the alcohol.

Zoledronate trisodium can be found in form XI, characterized by typical peaks at 6.2°, 7.9°, 8.8°, 10.6°, 12.2° 2θ±0.2° 2θ, and additional peaks at 15.0°, 15.4°, 17.5°, 18.8°, 19.6°, 20.5°, 22.3°, 23.7°, 25.7°, 29.6°, and 31.7° 2θ±0.2° 2θ. The TGA curve of form XI shows a weight loss of about 9% (dihydrate) within the temperature range 25-220° C.

Zoledronate disodium form XI may be prepared by treating Zoledronic acid, preferably form XII, and sodium hydroxide (ratio of acid/base 1:2.1) in water/ethanol or water/methanol 5%:95% v/v of water in ethanol or methanol.

Zoledronate Sodium Amorphous

Zoledronate sodium amorphous is prepared by treating Zoledronic acid and sodium hydroxide (ratio of acid/base 1:0.1 or 1:2.1 or 1:3.1) in water at room temperature, and precipitating the material by concentrating the solution by any means known in the art like evaporation of the solvent. Evaporation may be done using a vacuum.

EXAMPLES

Crystal Forms of Zoledronic Acid (ZLD-Ac)

Preparation of ZLD-Ac Crystal Form I

General procedure for the preparation of ZLD-Ac crystal form I starting from 1-Imidazoleacetic acid (IAA), Phosphorous acid ($H_3PO_3$) and Phosphorous oxychloride ($POCl_3$) (Examples 1-9, see Table 1):

A cylindrical reactor equipped with a mechanical stirrer, a thermometer, a reflux condenser and a dropping funnel, is loaded with 1-Imidazoleacetic acid (IAA), Phosphorous acid and a diluent (Toluene/Chlorobenzene/PEG-400/Silicon oil). The obtained suspension is heated to 75° C.-80° C. and Phosphorous oxychloride is added drop-wise. The reaction mixture is then heated to 75° C.-100° C. for 1-34 hours. Then water is added at 80° C.-100° C. The mixture is stirred vigorously for about 15 minutes. [In some cases, when Silicon oil is used as a diluent, there is a need to add Toluene in order to improve the separation between the oily phase and the aqueous phase]. Then the phases are separated. The aqueous phase is put in a clean reactor and heated to 95° C.-100° C. for 13.5-19 hours. Then it is cooled to 5° C. and absolute Ethanol is added to obtain a precipitate after stirring at 5° C. for 2.5-4 hours [In some cases a precipitate of Zoledronic acid is obtained without adding absolute Ethanol as an anti-solvent]. The white product is then filtered, washed with absolute Ethanol and dried in a vacuum oven at 50° C. for 17-24 hours to obtain Zoledronic acid crystal form I (LOD by TGA=6.3%-9.3%).

TABLE 1

Preparation of ZLD-Ac crystal form I starting from IAA, H$_3$PO$_3$ and POCl$_3$

| Example | Raw material (grams of IAA) | Ratio of reactants (equivalents) IAA/H$_3$PO$_3$/POCl$_3$ | Diluent/ volumes per grams of IAA | Temp. of reaction | Time of reaction | Amount of water for the hydrolysis step | Addition of Toluene to improve phases separation | Time of hydrolysis step | Amount of abs. EtOH/Acetone for the precipitation of ZLD-Ac | LOD by TGA | Yield (grams of ZLD-Ac) |
|---|---|---|---|---|---|---|---|---|---|---|---|
| 1 | IAA.HCl (5.4 g) | 1/3.6/4.5 | Silicon oil/ 6.5 vol. | 80° C. | 24 hrs | 45 ml | 50 ml | 19 hrs | 90 ml (EtOH) | 9.1% | 79% (7.8 g) |
| 2 | IAA.HCl (4.9 g) | 1/3.7/3.7 | Chloro-benzene/ 8.8 vol. | 100° C. | 1 hr | 50 ml | — | 15.5 hrs | 50 ml (EtOH) | — | — (8.2 g) |
| 3 | IAA.HCl (4.9 g) | 1/3/3 | PEG-400/ 5.5 vol. | 75° C. | 2 hrs | 27 ml | 27 ml | 13.5 hrs | 100 ml (Acetone) | — | — (1.1 g) |
| 4 | IAA.HCl (4.9 g) | 1/3/3.75 | Silicon oil/ 5.5 vol. | 80° C. | 22 hrs | 54 ml | 54 ml | 19 hrs | 54 ml (EtOH) | 6.8% | 76% (6.7 g) |
| 5 | IAA.HCl (4.9 g) | 1/3.7/3.7 | Toluene/ 8.8 vol. | 100° C. | 3 hrs | 44 ml | — | 16 hrs | 200 ml (EtOH) | 9.3% | 69% (6.2 g) |
| 6 | IAA.HCl (5.9 g) | 1/2/3 | Silicon oil/ 5.5 vol. | 80° C. | 23 hrs | 33 ml | — | 16 hrs | 200 ml (EtOH) | 7.9% | 38% (4.0 g) |
| 7 | IAA.HCl (6.0 g) | 1/4/4 | Silicon oil/ 5.5 vol. | 80° C. | 11 hrs | 33 ml | 33 ml | 16 hrs | 33 ml (EtOH) | 9.3% | 74% (8.2 g) |
| 8 MS-427 | IAA (12.0 g) | 1/3/3.75 | Silicon oil/ 6.0 vol. | 80° C. | 17 hrs | 72 ml | — | 16 hrs | — | 7.7% | 72% (20.0 g) |
| 9 | IAA (70 g) | 1/3/3.75 | Silicon oil/ 7.0 vol. | 80° C. | 34 hrs | 490 ml | 490 ml | 16 hrs | 490 ml (EtOH) (addition of EtOH at reflux temp.) | 6.3% | 59% (95.1 g) Purity by HPLC 98.3%* |

ZLD HPLC method:
Column: Phenomenex Phenyl-Hexyl 5 µm, 250 × 4.6 mm
Mobile phase: 40 mM Octansulfonic acid sodium salt in 1% HClO$_4$, 0.2% H$_3$PO$_4$:Methanol (85:15)
Detection: 220 nm Stability was measured versus the presence of Form II.

The stability data for example 4 in the table above is:

| | | TGA analysis | | | |
|---|---|---|---|---|---|
| Example | | Results | | | |
| No. 4 | Time Interval (months) | 25° C., 60% RH | 40° C., 75% RH | 55° C. | 2-8° C. |
| ZLD-Ac | 0 | I | I | I | I |
| | 1 M | | I | I | I |
| | 2 M | | I | I | |
| | 3 M | | I | I | |
| | 6 M | I | I | I | I |
| | 9 M | | | | |
| | 12 M | | | | |
| ZLD-Ac | 0 | | | | |
| | 1 M | | | | |
| | 2 M | | | 6.3 | 6.3 |
| | 3 M | | | 6.2 | 6.2 |
| | 6 M | | 6.5 | 6.5 | 6.4 |
| | 9 M | | | | |
| | 12 M | | | | |

Example 10

Sodium hydroxide (pearls, 91.1 g) was added to a suspension of Zoledronic acid crystal form XII (200.0 g) in water (2000 ml) at room temperature (pH=14) to obtain a clear solution. Then the pH of the solution was adjusted to pH 1 by addition of 32% aqueous HCl (300 ml). The solution was then cooled gradually to 5° C. and the white precipitate was filtered, washed with cold water (2×150 ml) and dried in a vacuum oven at 50° C. for 24 hours to obtain 161.7 g (84%) of Zoledronic acid crystal form I (LOD by TGA=6.7%). Purity by HPLC 99.9%.

Preparation of ZLD-Ac Crystal Form II

Example 11

A 250 ml three-necked flask equipped with a mechanical stirrer, a reflux condenser and a dropping funnel, was loaded with 1-Imidazoleacetic acid hydrochloride (4.9 g, 0.03 mole), phosphorous acid (4.9 g, 0.06 mole) and Silicon oil (Merck) (27 ml). The suspension was heated to 75° C. and phosphorous oxychloride (10.5 ml, 0.11 mole) was added drop-wise during 30 minutes. The reaction mixture was then heated to 80° C. for 27 hours. Then water (27 ml) and toluene (30 ml) were added at 80° C. The mixture was stirred vigorously for about 15 minutes. Then the toluene phase (containing the silicon oil) and the aqueous phase were separated. The aqueous phase was put in a clean flask and heated to 90° C. for 16 hours. Then it was cooled to room temperature and absolute Ethanol (27 ml) was added during the cooling process to obtain a white precipitate immediately. The mixture was stirred at 5° C. for 4 hours. The white product was then filtered, washed with absolute Ethanol (2×15 ml) and dried in a vacuum oven at 50° C. for 24 hours to obtain 4.9 g (58%) of Zoledronic acid crystal form II (LOD by TGA=5.2%).

Example 12

Zoledronic acid crystal form I (2.0 g) was stirred in Toluene (20 ml) at reflux temperature for 14 hours. Then the suspension was cooled to room temperature, filtered, washed with Toluene (1×15 ml) and dried in a vacuum oven at 50° C. for 24 hours to obtain 1.6 g of Zoledronic acid crystal form II.

Preparation of ZLD-Ac Crystal Form XII

Example 13

Zoledronic acid crystal form XVIII (10.0 g) was dissolved in water (260 ml) at reflux temperature. The obtained solution was stirred at reflux temperature for about 20 minutes to obtain a clear solution. Then it was cooled to 75° C. during 2 hours and stirred at this temperature for 1 hour. The turbid solution was further cooled to 25° C. during 4.5 hours and stirred at this temperature for 1 hour. After cooling to 0° C. during 2 hours and stirring at this temperature for 16 hours, the white precipitate was filtered and dried in a vacuum oven at 50° C. for 24 hours to obtain 7.8 g of Zoledronic acid crystal form XII.

Example 14

Zoledronic acid crystal form I (2.0 g) was stirred in Acetic acid (20 ml) at room temperature for 15.5 hours. Then it was filtered, washed with Acetic acid (2×5 ml) and dried in a vacuum oven at 50° C. for 24 hours to obtain 2.0 g of Zoledronic acid crystal form XII.

Preparation of ZLD-Ac Crystal Form XV

Example 15

A 250 ml flask was loaded with Zoledronic acid form I (4.8 g), Sodium hydroxide (0.7 g) and absolute Ethanol (10 volumes per grams of ZLD-Ac) (48 ml). The reaction mixture was heated to reflux temperature for 16 hours. Then it was cooled to room temperature. Further cooling was performed using an ice-bath. The precipitate was then filtered, washed with absolute Ethanol (2×20 ml) and dried in a vacuum oven at 50° C. for 23 hours to give 4.9 g (96%) of Zoledronate monosodium crystal form XV in a mixture with Zoledronic acid crystal form I (LOD by TGA=5.8%).

Example 16

A 250 ml flask was loaded with Zoledronic acid form I (4.8 g), Sodium hydroxide (0.7 g) and Methanol (10 volumes per grams of ZLD-Ac) (48 ml). The reaction mixture was heated to reflux temperature for 16 hours. Then it was cooled to room temperature. Further cooling was performed using an ice-bath. The precipitate was then filtered, washed with Methanol (2×10 ml) and dried in a vacuum oven at 50° C. for 22 hours to give 4.8 g (99%) of Zoledronate monosodium crystal form XV (LOD by TGA=0.8%). Purity by HPLC 99.9%.

Example 17

Zoledronic acid crystal form XII (2.0 g) was stirred in Methanol (20 ml) at reflux temperature for 19 hours. Then the suspension was cooled to room temperature, filtered, washed with Methanol (1×5 ml) and dried in a vacuum oven at 50° C. for 24 hours to obtain 1.8 g of a mixture of Zoledronic acid crystal forms XV and XVIII.

Preparation of ZLD-Ac Crystal Form XVIII

Example 18

A 3 liter reactor equipped with a mechanical stirrer, a thermometer, a reflux condenser and a dropping funnel, was loaded with 1-Imidazoleacetic acid (70.0 g, 0.56 mole), Phosphorous acid (136.7 g, 1.67 mole) and Silicon oil (M-350) (490 ml). The suspension was heated to 80° C. and Phosphorous oxychloride (194.4 ml, 2.08 mole) was added drop-wise during 4 hours. The reaction mixture was stirred at 80° C. for 22 hours. Then water (490 ml) was added slowly at 80° C. The mixture was stirred vigorously for about 30 minutes. Then the silicon oil phase and the aqueous phase were separated. The aqueous phase was put in a clean reactor and heated to 97° C. for 17.5 hours. Then absolute Ethanol (490 ml) was added and the solution was stirred at reflux (87° C.) for 2 hours. The solution was then cooled to 70° C.-72° C. during about 1 hour and was kept at this temperature for 1 hour. After cooling to 25° C. during 2.5 hours and stirring at this temperature for 1 hour, half of the product was filtered, washed with small amount of cold water and dried in a vacuum oven at 50° C. for 20 hours to obtain 50.8 g of Zoledronic acid crystal form XVIII (MS-507-crop I, LOD by TGA=1.9%). The rest of the suspension was cooled to 0° C. during 2 hours and was stirred at this temperature for about 16 hours. Then the product was filtered and dried in a vacuum oven at 50° C. for 24 hours to obtain 26 g of Zoledronic acid crystal form XVIII (MS-507-crop II, LOD by TGA=1.0%). The overall yield of the process is 50% purity by HPLC 97.7%.

Example 19

Zoledronic acid crystal form I (2.0 g) was stirred in Methanol (20 ml) at room temperature for 14.5 hours. Then it was filtered, washed with Methanol (2×10 ml) and dried in a vacuum oven at 50° C. for 25 hours to obtain 1.9 g of Zoledronic acid crystal form XVIII.

Example 20

Zoledronic acid crystal form I (2.0 g) was stirred in Methanol (20 ml) at reflux temperature for 16 hours. Then the suspension was cooled to room temperature and the white solid was filtered, washed with Methanol (2×5 ml) and dried in a vacuum oven at 50° C. for 24 hours to obtain 1.7 g of Zoledronic acid crystal form XVIII.

Example 21

Zoledronic acid crystal form I (2.0 g) was stirred in 1-Butanol (20 ml) at reflux temperature for 15.5 hours. Then the suspension was cooled to room temperature and the white solid was filtered, washed with 1-Butanol (1×5 ml) and dried in a vacuum oven at 50° C. for 24 hours to obtain 1.8 g of Zoledronic acid crystal form XVIII.

Example 22

Zoledronic acid crystal form I (2.0 g) was stirred in MTBE (20 ml) at reflux temperature for 15 hours. Then the suspension was cooled to room temperature and the white solid was filtered, washed with MTBE (1×10 ml) and dried in a vacuum oven at 50° C. for 25 hours to obtain 1.4 g of Zoledronic acid crystal form XVIII.

Example 23

Zoledronic acid crystal form I (2.0 g) was stirred in Acetonitrile (20 ml) at room temperature for 22 hours. Then the suspension was filtered, washed with Acetonitrile (2×5 ml) and dried in a vacuum oven at 50° C. for 23 hours to obtain 2.0 g of Zoledronic acid crystal form XVIII.

Example 24

Zoledronic acid crystal form I (2.0 g) was stirred in a mixture of Methanol/water (1:1 v/v) (20 ml) at reflux temperature for 18 hours. Then the suspension was cooled to 0° C., filtered and dried in a vacuum oven at 50° C. for 22 hours to obtain 1.8 g of Zoledronic acid crystal form XVIII.

Example 25

Zoledronic acid crystal form I (2.0 g) was stirred in a mixture of Ethanol/water (1:1 v/v) (20 ml) at reflux temperature for 18 hours. Then the suspension was cooled to 0° C., filtered and dried in a vacuum oven at 50° C. for 22 hours to obtain 1.8 g of Zoledronic acid crystal form XVIII.

Preparation of ZLD-Ac Crystal Form XX

Example 26

Zoledronic acid crystal form I (2.0 g) was stirred in absolute Ethanol (20 ml) at reflux temperature for 16 hours. The suspension was then cooled to room temperature and the white solid was filtered, washed with absolute Ethanol (2×5 ml) and dried in a vacuum oven at 50° C. for 22.5 hours to obtain 1.9 g of Zoledronic acid crystal form XX in a mixture with crystal form I.

Example 27

Zoledronic acid crystal form I (2.0 g) was stirred in 1-Propanol (20 ml) at reflux temperature for 11.5 hours. The suspension was then cooled to room temperature and the white solid was filtered, washed with 1-Propanol (2×5 ml) and dried in a vacuum oven at 50° C. for 24 hours to obtain 1.9 g of Zoledronic acid crystal form XX.

Example 28

Zoledronic acid crystal form I (2.0 g) was stirred in 2-Propanol (IPA) (20 ml) at reflux temperature for 14 hours. The suspension was then cooled to room temperature and the white solid was filtered, washed with IPA (2×5 ml) and dried in a vacuum oven at 50° C. for 24 hours to obtain 1.9 g of Zoledronic acid crystal form XX. Purity by HPLC 99.8%.

Preparation of ZLD-Ac Crystal Form XXVI

Example 29

Zoledronic acid crystal form I (2.0 g) was stirred in 2-Butanol (20 ml) at reflux temperature for about 15 hours. The suspension was then cooled to room temperature and the white solid was filtered, washed with 2-Butanol (2×5 ml) and dried in a vacuum oven at 50° C. for 24 hours to obtain 1.9 g of Zoledronic acid crystal form XXVI.

Crystal Forms of Zoledronate Monosodium (ZLD-Na)

Preparation of ZLD-Na Crystal Form VIII

Example 30

A 0.5 liter reactor equipped with a mechanical stirrer, a thermometer and a reflux condenser was loaded with Zoledronic acid form I (10.0 g) and water (247 ml). The suspension was heated to 94° C. to obtain a clear solution. Sodium hydroxide (pearls, 1.42 g) was added. A pH test of the sodium salt showed pH=4.54. The solution was cooled to 60° C. and IPA (10.5 ml) was added. The reaction mixture was cooled to room temperature during 2 hours and was stirred at this temperature for about 64 hours. After cooling to 5° C. and stirring at this temperature for 1 hour, the white precipitate was filtered, washed with cold water (1×10 ml) and dried in a vacuum oven at 50° C. for 23.5 hours to obtain 7.0 g of Zoledronate monosodium crystal form VIII (pH=4.32). Purity by HPLC 100.0%.

Example 31

A 0.5 liter reactor equipped with a mechanical stirrer, a thermometer, a reflux condenser and a dropping funnel, was loaded with Zoledronic acid form I (10.0 g) and water (247 ml). The suspension was heated to 94° C. to obtain a clear solution. A 40% aqueous solution of Sodium hydroxide (3.45 g) was added drop-wise. The solution was then cooled to 4° C. during 2 hours and was stirred at this temperature for about 64 hours to obtain a massive precipitate. The white precipitate was filtered, washed with cold water (1×10 ml) and dried in a vacuum oven at 50° C. for 26 hours to obtain 7.6 g (64%) of Zoledronate monosodium crystal form VIII (LOD by TGA=15.1%).

Example 32→

A 0.5 liter reactor equipped with a mechanical stirrer, a thermometer, a reflux condenser and a dropping funnel, was loaded with Zoledronic acid form I (10.0 g) and water (247 ml). The suspension was heated to 94° C. to obtain a clear solution. A 40% aqueous solution of Sodium hydroxide (3.45 g) was added drop-wise. The solution was then cooled to room temperature and stirred at this temperature for 16 hours. After cooling to 3° C. and stirring at this temperature for 1.5 hour, the white precipitate was filtered, washed with Methanol (2×15 ml) and dried in a vacuum oven at 50° C. for 25 hours to obtain 5.8 g (49%) of Zoledronate monosodium crystal form VIII (LOD by TGA=15.1%). The obtained Form VIII (2 g) was recrystallized form water (34 ml) to give 1.4 g (72%) of Zoledronic acid crystal form VIII (LOD by TGA=11.3%). Purity by HPLC 100.0%.

Remark:

Regarding the next examples: the composition of the reflux media is expressed on a volume per volume basis (abbreviated v/v). The amount of water that should be added to the reflux media is calculated according to the following formula:

(10 volumes of alcohol per grams of ZLD-Ac×100)/$X$
% of alcohol=$Y$ when $Y$ is the total amount of
alcohol and water together→$Y$×(100−$X$)% of
water/100=$Z$ when $Z$ is the volume of water that should be added].

Example 33

A solution of sodium hydroxide (0.7 g) in a mixture of water (80% v/v)/Ethanol (20% v/v, 10 volumes per grams of ZLD-Ac) (36 ml) was added drop-wise to a suspension of Zoledronic acid form I (4.8 g) in a mixture of water (80% v/v)/Ethanol (20% v/v, 10 volumes per grams of ZLD-Ac) (202 ml) at reflux temperature. The reaction mixture was heated at reflux temperature for additional 16 hours. Then the reaction mixture was cooled to room temperature. Further cooling was performed using an ice-bath. The precipitate was then filtered, washed with absolute Ethanol (2×20 ml) and dried in a vacuum oven at 50° C. for 22 hours to give 4.7 g (83%) of Zoledronate monosodium crystal form VIII (LOD by TGA=15.5%). Purity by HPLC 99.9%.

Example 34

A solution of sodium hydroxide (0.7 g) in a mixture of water (80% v/v)/Methanol (20% v/v, 10 volumes per grams of ZLD-Ac fprm I) (36 ml) was added drop-wise to a suspension of Zoledronic acid (4.8 g) in a mixture of water (80% v/v)/Methanol (20% v/v, 10 volumes per grams of ZLD-Ac form I) (202 ml) at reflux temperature. The reaction mixture was heated at reflux temperature for additional 16 hours. Then the reaction mixture was cooled to room temperature. Further cooling was performed using an ice-bath. The precipitate was then filtered, washed with Methanol (1×20 ml) and dried in a vacuum oven at 50° C. for 22 hours to give 4.7 g (81%) of Zoledronate monosodium crystal form VIII (LOD by TGA=16.03%). Purity by HPLC 99.9%.

Example 35

A solution of sodium hydroxide (0.7 g) in a mixture of water (80% v/v)/IPA (20% v/v, 10 volumes per grams of ZLD-Ac form I) (38 ml) was added drop-wise to a suspension of Zoledronic acid (5.0 g) in a mixture of water (80% v/v)/IPA (20% v/v, 10 volumes per grams of ZLD-Ac form I) (212 ml) at reflux temperature. The reaction mixture was heated at reflux temperature for additional 16 hours. Then the reaction mixture was cooled to room temperature. Further cooling was performed using an ice-bath. The precipitate was then filtered, washed with IPA (2×20 ml) and dried in a vacuum oven at 50° C. for 24 hours to give 4.7 g (79%) of Zoledronate monosodium crystal form VIII (LOD by TGA=15.40%). Purity by HPLC 99.95%.

Example 36

A solution of sodium hydroxide (0.7 g) in a mixture of water (60% v/v)/IPA (40% v/v, 10 volumes per grams of ZLD-Ac form I) (19 ml) was added drop-wise to a suspension of Zoledronic acid (5.0 g) in a mixture of water (60% v/v)/IPA (40% v/v, 10 volumes per grams of ZLD-Ac form I) (106 ml) at reflux temperature. The reaction mixture was heated at reflux temperature for additional 16 hours. Then the reaction mixture was cooled to room temperature. Further cooling was performed using an ice-bath. The precipitate was then filtered, washed with IPA (1×20 ml) and dried in a vacuum oven at 50° C. for 27 hours to give 0.6 g (10%) of Zoledronate monosodium crystal form VIII (LOD by TGA=15.0%).

Preparation of ZLD-Na Crystal Form XVI

Example 37

A solution of sodium hydroxide (0.7 g) in a mixture of water (50% v/v)/Ethanol (50% v/v, 10 volumes per grams of ZLD-Ac form I) (14 ml) was added drop-wise to a suspension of Zoledronic acid (4.8 g) in a mixture of water (50% v/v)/Ethanol (50% v/v, 10 volumes per grams of ZLD-Ac form I) (81 ml) at reflux temperature. The reaction mixture was heated at reflux temperature for additional 16 hours. Then the reaction mixture was cooled to room temperature. Further cooling was performed using an ice-bath. The precipitate was then filtered, washed with absolute Ethanol (2×20 ml) and dried in a vacuum oven at 50° C. for 18 hours to give 5.2 g (98%) of Zoledronate monosodium crystal form XVI (LOD by TGA=9.9%). Purity by HPLC 99.95%.

Example 38

A solution of sodium hydroxide (0.7 g) in a mixture of water (50% v/v)/IPA (50% v/v, 10 volumes per grams of ZLD-Ac form I) (15 ml) was added drop-wise to a suspension of Zoledronic acid (5.0 g) in a mixture of water (50% v/v)/IPA (50% v/v, 10 volumes per grams of ZLD-Ac form I) (85 ml) at reflux temperature. The reaction mixture was heated at reflux temperature for additional 16 hours. Then the reaction mixture was cooled to room temperature. Further cooling was performed using an ice-bath. The precipitate was then filtered, washed with IPA (2×20 ml) and dried in a vacuum oven at 50° C. for 24 hours to give 5.2 g (94%) of Zoledronate monosodium crystal form XVI (LOD by TGA=9.8%). Purity by HPLC 99.9%.

Example 39

A solution of sodium hydroxide (0.7 g) in a mixture of water (50% v/v)/Methanol (50% v/v, 10 volumes per grams of ZLD-Ac form I) (14 ml) was added drop-wise to a suspension of Zoledronic acid form I (4.8 g) in a mixture of water (50% v/v)/Ethanol (50% v/v, 10 volumes per grams of ZLD-Ac form I) (81 ml) at reflux temperature. The reaction mixture was heated at reflux temperature for additional 16 hours. Then the reaction mixture was cooled to room temperature. Further cooling was performed using an ice-bath. The precipitate was then filtered, washed with Methanol (1×25 ml) and dried in a vacuum oven at 50° C. for 25.5 hours to give 4.8 g (89%) of Zoledronate monosodium crystal form XVI (LOD by TGA=11.1%). Purity by HPLC 99.9%.

Preparation of ZLD-Na Crystal Form XVII

Example 40

A 0.5 liter reactor equipped with a mechanical stirrer, a thermometer, a reflux condenser and a dropping funnel, was loaded with Zoledronic acid form I (10.0 g) and water (247 ml). The suspension was heated to 94° C. to obtain a clear solution. A 29% aqueous solution of Sodium hydroxide (3.45 g) was added drop-wise. The solution was then cooled to room temperature and stirred at this temperature for 16 hours. After cooling to 3° C. the product was isolated by filtration. Further cooling of the mother-liquid led to the formation of a white precipitate. The precipitate was filtered and dried in a vacuum oven at 50° C. for 24 hours to obtain 0.6 g of Zoledronate monosodium crystal form XVII (LOD by TGA=10.3%).

Crystal Forms of Zoledronate Disodium (ZLD-Na$_2$)

Preparation of ZLD-Na$_2$ Crystal Form V

Example 41

A solution of sodium hydroxide (0.7 g) in a mixture of water (X % v/v)/Ethanol (Y % v/v, 10 volumes per grams of ZLD-Ac form XII) (10-15 ml) was added drop-wise to a suspension of Zoledronic acid form XII (4.98 g) in a mixture of water (X % v/v)/Ethanol (Y % v/v, 10 volumes per grams of ZLD-Ac) (53-85 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate disodium crystal form V.

| Sample No. | X % H$_2$O | Y % EtOH | Total volume of solution (H$_2$O/EtOH) | Yield (g/%) | LOD by TGA |
|---|---|---|---|---|---|
| 1 | 20% (13 ml) | 80% (50 ml) | 63 ml | 4.9 g/89% | 10.3% |
| 2 | 40% (33 ml) | 60% (50 ml) | 83 ml | 5.0 g/90% | 10.3% |
| 3 | 50% (50 ml) | 50% (50 ml) | 100 ml | 5.1 g/91% | 10.7% |

Example 42

A solution of sodium hydroxide (0.7 g) in a mixture of water (X % v/v)/Methanol (Y % v/v, 10 volumes per grams of ZLD-Ac form XII) (13-15 ml) was added drop-wise to a suspension of Zoledronic acid form XII (4.98 g) in a mixture of water (X % v/v)/Methanol (Y % v/v, 10 volumes per grams of ZLD-Ac) (70-85 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate disodium crystal form V.

| Sample No. | X % H$_2$O | Y % MeOH | Total volume of solution (H$_2$O/MeOH) | Yield (g/%) | LOD by TGA |
|---|---|---|---|---|---|
| 1 | 40% (33 ml) | 60% (50 ml) | 83 ml | 4.7 g/85% | 10.0% |
| 2 | 50% (50 ml) | 50% (50 ml) | 100 ml | 4.9 g/88% | 10.8% |

Example 43

A solution of sodium hydroxide (0.7 g) in a mixture of water (X % v/v)/IPA (Y % v/v, 10 volumes per grams of ZLD-Ac form XII) (13-15 ml) was added drop-wise to a suspension of Zoledronic acid (4.98 g) in a mixture of water (X % v/v)/IPA (Y % v/v, 10 volumes per grams of ZLD-Ac form XII) (70-85 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate disodium crystal form V.

| Sample No. | X % H$_2$O | Y % IPA | Total volume of solution (H$_2$O/IPA) | Yield (g/%) | LOD by TGA |
|---|---|---|---|---|---|
| 1 | 40% (33 ml) | 60% (50 ml) | 83 ml | 4.7 g | — |
| 2 | 50% (50 ml) | 50% (50 ml) | 100 ml | 4.8 g/85% | 11.2% |

Example 44

A solution of sodium hydroxide (1.4 g) in a mixture of water (X % v/v)/Ethanol (Y % v/v, 10 volumes per grams of ZLD-Ac form I) (10-15 ml) was added drop-wise to a suspension of Zoledronic acid form I (5.0 g) in a mixture of water (X % v/v)/Ethanol (Y % v/v, 10 volumes per grams of ZLD-Ac) (53-85 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate disodium crystal form V. Purity by HPLC 99.9%.

| Sample No. | X % H$_2$O | Y % EtOH | Total volume of solution (H$_2$O/EtOH) | Yield (g/%) | LOD by TGA |
|---|---|---|---|---|---|
| 1 | 20% (13 ml) | 80% (50 ml) | 63 ml | 6.0 g/96% | 9.7% |
| 2 | 50% (50 ml) | 50% (50 ml) | 100 ml | 6.0 g/94% | 10.9% |

Example 45

A solution of sodium hydroxide (1.4 g) in a mixture of water (X % v/v)/Methanol (Y % v/v, 10 volumes per grams of ZLD-Ac form I) (15 ml) was added drop-wise to a suspension of Zoledronic acid form I (5.0 g) in a mixture of water (X % v/v)/Methanol (Y % v/v, 10 volumes per grams of ZLD-Ac) (85 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate disodium crystal form V. Purity by HPLC 99.95%.

| Sample No. | X % H$_2$O | Y % MeOH | Total volume of solution (H$_2$O/MeOH) | Yield (g/%) | LOD by TGA |
|---|---|---|---|---|---|
| 1 | 50% (50 ml) | 50% (50 ml) | 100 ml | 6.0 g/94% | 11.1% |

Example 46

A solution of sodium hydroxide (1.4 g) in a mixture of water (X % v/v)/IPA (Y % v/v, 10 volumes per grams of ZLD-Ac form I) (10-15 ml) was added drop-wise to a suspension of Zoledronic acid (5.0 g) in a mixture of water (X % v/v)/IPA (Y % v/v, 10 volumes per grams of ZLD-Ac) (53-85 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate disodium crystal form V. Purity by HPLC 99.95%.

| Sample No. | X % H$_2$O | Y % IPA | Total volume of solution (H$_2$O/IPA) | Yield (g/%) | LOD by TGA |
|---|---|---|---|---|---|
| 1 | 20% (13 ml) | 80% (50 ml) | 63 ml | 5.7 g/91% | 10.3% |
| 2 | 50% (50 ml) | 50% (50 ml) | 100 ml | 5.7 g/90% | 10.6% |

Preparation of ZLD-Na$_2$ Crystal Form VI

Example 47

A solution of sodium hydroxide (0.7 g) in a mixture of water (60% v/v)/Ethanol or Methanol (40% v/v, 10 volumes per grams of ZLD-Ac form XII) (19 ml) was added drop-wise to a suspension of Zoledronic acid form XII (4.98 g) in a mixture of water (60% v/v)/Ethanol or Methanol (40% v/v, 10 volumes per grams of ZLD-Ac) (106 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate disodium crystal form VI.

| Sample No. | X % H$_2$O | Y % EtOH or MeOH | Total volume of solution (H$_2$O/EtOH or MeOH) | Yield (g/%) | LOD by TGA |
|---|---|---|---|---|---|
| 1 | 60% (75 ml) | 40% EtOH (50 ml) | 125 ml | 4.9 g/86% | 12.9% |
| 2 | 60% (75 ml) | 40% MeOH (50 ml) | 125 ml | 4.5 g/78% | 13.0% |

Example 48

A solution of sodium hydroxide (1.4 g) in a mixture of water (80% v/v)/IPA (20% v/v, 10 volumes per grams of ZLD-Ac form I) (38 ml) was added drop-wise to a suspension of Zoledronic acid form I (5.0 g) in a mixture of water (80% v/v)/IPA (20% v/v, 10 volumes per grams of ZLD-Ac) (212 ml) at reflux temperature. The reaction mixture was heated at reflux temperature for additional 16 hours. Then the reaction mixture was cooled to room temperature and the solution was evaporated to dryness. The obtained solid was dried in a vacuum oven at 50° C. for 5 hours to give 5.2 g (78%) of Zoledronate disodium crystal form VI (LOD by TGA=15.4%). Purity by HPLC 99.9%.

Example 49

Zoledronate disodium crystal form XIX (4.0 g) was dissolved in water (10 ml) at reflux temperature. After about 30 minutes at reflux temperature a precipitate was obtained. The suspension was then cooled to 0° C. using an ice-bath. The solid was isolated by filtration and dried in a vacuum oven at 50° C. for 17 hours to give 2.0 g (50%) of Zoledronate disodium crystal form VI.

Preparation of ZLD-Na$_2$ Crystal Form VII

Example 50

A 0.5 liter reactor equipped with a mechanical stirrer, a thermometer and a reflux condenser was loaded with Zoledronic acid form I (10.0 g) and water (260 ml). The suspension was heated to 80° C. to obtain a clear solution. Sodium hydroxide (pearls, 2.84 g) was added. A pH test of the sodium salt showed pH=7.35. The solution was cooled to 60° C. and IPA (10.5 ml) was added. The reaction mixture was cooled to room temperature during 2 hours and was stirred at this temperature for about 16 hours. After cooling to 5° C. and stirring at this temperature for 2 hours, the solution was evaporated to dryness to obtain a white solid. The obtained solid was reslurried in water (50 ml) and cooled to 4° C. The product was then isolated by filtration and dried in a vacuum oven at 50° C. for 24 hours to obtain 3.2 g of Zoledronate disodium crystal form VII (24%) (pH=7.27). Purity by HPLC 100.0%.

Example 51

A 0.5 liter reactor equipped with a mechanical stirrer, a thermometer, a reflux condenser and a dropping funnel, was loaded with Zoledronic acid form I (10.0 g) and water (130 ml). The suspension was heated to reflux temperature to obtain a clear solution. A 40% aqueous solution of Sodium hydroxide (6.9 g) was added drop-wise. The solution was then cooled to 4° C. during 2 hours and was stirred at this temperature for about 1.5 hours. The solution was concentrated to half of its volume to obtain a precipitate. The white precipitate was filtered and dried in a vacuum oven at 50° C. for 22 hours to obtain 2.7 g (22%) of Zoledronate disodium crystal form VII (LOD by TGA=10.7%).

Example 52

A 0.5 liter reactor equipped with a mechanical stirrer, a thermometer, a reflux condenser and a dropping funnel, was loaded with Zoledronic acid form I (10.0 g) and water (130 ml). The suspension was heated to reflux temperature (92° C.) to obtain a clear solution. A 40% aqueous solution of Sodium hydroxide (6.9 g) was added drop-wise. The solution was then cooled to 25° C. was stirred at this temperature for about 16 hours. The solution was then concentrated to half of its volume to obtain a precipitate. The white precipitate was filtered and dried in a vacuum oven at 50° C. for 18.5 hours to obtain 2.8 g (23%) of Zoledronate disodium crystal form VII (LOD by TGA=10.2%). Purity by HPLC 100.0%.

Example 53

A solution of sodium hydroxide (0.7 g) in a mixture of water (80% v/v)/Ethanol or Methanol or IPA (20% v/v, 10 volumes per grams of ZLD-Ac form XII) (38 ml) was added drop-wise to a suspension of Zoledronic acid form XII (4.98 g) in a mixture of water (80% v/v)/Ethanol or Methanol or IPA (20% v/v, 10 volumes per grams of ZLD-Ac) (212 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate disodium crystal form VII.

| Sample No. | X % H$_2$O | Y % EtOH or MeOH or IPA | Total volume of solution (H$_2$O/EtOH or MeOH or IPA) | Yield (g/%) | LOD by TGA |
|---|---|---|---|---|---|
| 1 | 80% (200 ml) | 20% EtOH (50 ml) | 250 ml | 4.9 g/89% | 9.2% |
| 2 | 80% (200 ml) | 20% MeOH (50 ml) | 250 ml | 4.5 g/83% | 7.6% |
| 3 | 80% (200 ml) | 20% IPA (50 ml) | 250 ml | 4.7 g/85% | 10.3% |

Example 54

A solution of sodium hydroxide (0.7 g) in a mixture of water (60% v/v)/IPA (40% v/v, 10 volumes per grams of ZLD-Ac form XII) (19 ml) was added drop-wise to a suspension of Zoledronic acid form XII (4.98 g) in a mixture of water (60% v/v)/IPA (40% v/v, 10 volumes per grams of ZLD-Ac) (106 ml) at reflux temperature. The reaction mixture was heated at reflux temperature for additional 16 hours. Then the reaction mixture was cooled to room temperature. Further cooling was performed using an ice-bath. The precipitate was then filtered, washed with IPA (1×20 ml) and dried in a vacuum oven at 50° C. for 24 hours to give Zoledronate monosodium crystal form VIII (crop I). Then the precipitate from the mother-liquid was isolated by filtration as well, and dried in a vacuum oven at 50° C. for 24 hours to give 2.8 g (13%) of Zoledronate disodium crystal form VII (crop II).

Example 55

A solution of sodium hydroxide (1.4 g) in a mixture of water (80% v/v)/Ethanol (20% v/v, 10 volumes per grams of ZLD-Ac form I) (38 ml) was added drop-wise to a suspension of Zoledronic acid form I (5.0 g) in a mixture of water (80% v/v)/Ethanol (20% v/v, 10 volumes per grams of ZLD-Ac) (212 ml) at reflux temperature. The reaction mixture was heated at reflux temperature for additional 18.5 hours. Then the reaction mixture was cooled to room temperature and the solution was evaporated to dryness to obtain 6.7 g (98%) of Zoledronate disodium crystal form VII (LOD by TGA=16.8%). Purity by HPLC 99.9%.

Preparation of ZLD-Na$_2$ Crystal Form X

Example 56

A solution of sodium hydroxide (0.7 g) in a mixture of water (20% v/v)/IPA (80% v/v, 10 volumes per grams of ZLD-Ac form XII) (10 ml) was added drop-wise to a suspension of Zoledronic acid form XII (4.98 g) in a mixture of water (20% v/v)/IPA (80% v/v, 10 volumes per grams of ZLD-Ac) (53 ml) at reflux temperature. The reaction mixture was heated at reflux temperature for additional 16 hours. Then the reaction mixture was cooled to room temperature. Further cooling was performed using an ice-bath. The precipitate was then filtered, washed with IPA (1×25 ml) and dried in a vacuum oven at 50° C. for 24 hours to give 4.7 g (91%) of Zoledronate disodium crystal form X (LOD by TGA=2.6%).

Preparation of ZLD-Na$_2$ Crystal Form XIII

Example 57

A solution of sodium hydroxide (1.4 g) in a mixture of water (5% v/v)/Ethanol (95% v/v, 10 volumes per grams of ZLD-Ac form I) (8 ml) was added drop-wise to a suspension of Zoledronic acid form I (5.0 g) in a mixture of water (5% v/v)/Ethanol (95% v/v, 10 volumes per grams of ZLD-Ac) (45 ml) at reflux temperature. The reaction mixture was heated at reflux temperature for additional 19.5 hours. Then the reaction mixture was cooled to room temperature. Further cooling was performed using an ice-bath. The precipitate was then filtered, washed with Ethanol (1×10 ml) and dried in a vacuum oven at 50° C. for 20 hours to give 4.9 g (84%) of Zoledronate disodium crystal form XIII (LOD by TGA=3.4%). Purity by HPLC 99.9%.

Preparation of ZLD-Na$_2$ Crystal Form XIV

Example 58

A solution of sodium hydroxide (0.7 g) in a mixture of water (20% v/v)/DMF (80% v/v, 10 volumes per grams of ZLD-Ac form XII) (10 ml) was added drop-wise to a suspension of Zoledronic acid form XII (4.98 g) in a mixture of water (20% v/v)/DMF (80% v/v, 10 volumes per grams of ZLD-Ac) (53 ml) at reflux temperature. The reaction mixture was heated at reflux temperature for additional 16 hours. Then the reaction mixture was cooled to room temperature. Further cooling was performed using an ice-bath. The precipitate was then filtered, washed with DMF (2×10 ml) and dried in a vacuum oven at 50° C. for 24 hours to give 4.8 g (92%) of Zoledronate disodium crystal form XIV (LOD by TGA=1.9%).

Example 59

A solution of sodium hydroxide (1.4 g) in a mixture of water (20% v/v)/Methanol (80% v/v, 10 volumes per grams of ZLD-Ac form I) (10 ml) was added drop-wise to a suspension of Zoledronic acid form I (5.0 g) in a mixture of water (20% v/v)/Methanol (80% v/v, 10 volumes per grams of ZLD-Ac) (53 ml) at reflux temperature. The reaction mixture was heated at reflux temperature for additional 17 hours. Then the reaction mixture was cooled to room temperature. Further cooling was performed using an ice-bath. The precipitate was then filtered, washed with Methanol (1×10 ml) and dried in a vacuum oven at 50° C. for 26 hours to give 5.6 g (97%) of Zoledronate disodium crystal form XIV (LOD by TGA=1.4%). Purity by HPLC 99.9%.

Preparation of ZLD-Na$_2$ Crystal Form XIX

Example 60

Zoledronate disodium crystal form VII (1.0 g) was dissolved in water (19 ml) at reflux temperature. After about 30 minutes at reflux temperature a light precipitate was obtained. The suspension was then cooled to 0° C. using an ice-bath and was concentrated under vacuum to obtain a massive precipitation. The solid was isolated by filtration after further stirring at 0° C., and dried in a vacuum oven at 50° C. for 27 hours to give 0.4 g (40%) of Zoledronate disodium crystal form XIX.

Example 61

A 0.5 liter reactor equipped with a mechanical stirrer, a thermometer, a reflux condenser and a dropping funnel, was loaded with Zoledronic acid form I (20.0 g) and water (260 ml). The suspension was heated to reflux temperature (92° C.) to obtain a clear solution. A 40% aqueous solution of Sodium hydroxide (13.8 g) was added drop-wise. The solution was then cooled to 25° C. and was stirred at this temperature for about 16 hours. The solution was then concentrated to half of its volume to obtain a precipitate. After stirring at 0° C. for 72 hours, the white precipitate was filtered and dried in a vacuum oven at 50° C. for 23 hours to obtain 10.4 g of Zoledronate disodium crystal form XIX.

Preparation of ZLD-Na$_2$ Crystal Form XXV

Example 62

A solution of sodium hydroxide (1.4 g) in a mixture of water (80% v/v)/Methanol (20% v/v, 10 volumes per grams of ZLD-Ac form I) (38 ml) was added drop-wise to a suspension of Zoledronic acid form I (5.0 g) in a mixture of water (80% v/v)/Methanol (20% v/v, 10 volumes per grams of ZLD-Ac) (212 ml) at reflux temperature. The reaction mixture was heated at reflux temperature for additional 19 hours. Then the reaction mixture was cooled to room temperature. Further cooling was performed using an ice-bath. The solution was then evaporated to dryness to obtain 6.1 g (99%) of Zoledronate disodium crystal form XXV (LOD by TGA=7.4%). Purity by HPLC 99.9%.

Preparation of ZLD-Na$_2$ Crystal Form XXVII

Example 63

A 100 ml flask was loaded with Zoledronic acid form I (4.9 g), Sodium hydroxide (1.4 g), Methanol (50 ml) and water (2.5 ml) [=5% v/v water in Methanol]. The reaction mixture was heated to reflux temperature for 21 hours. Then the reaction mixture was cooled to room temperature. Further cooling was performed using an ice-bath. The precipitate was then filtered, washed with absolute Ethanol (2×75 ml) and dried in a vacuum oven at 50° C. for 27.5 hours to give 5.7 g (93%) of Zoledronate disodium crystal form XXVII (LOD by TGA=5.3%). Purity by HPLC 99.9%.

Example 64

A solution of sodium hydroxide (0.7 g) in a mixture of water (20% v/v)/Methanol (80% v/v, 10 volumes per grams of ZLD-Ac form XII) (10 ml) was added drop-wise to a suspension of Zoledronic acid form XII (4.98 g) in a mixture of water (20% v/v)/Methanol (80% v/v, 10 volumes per grams of ZLD-Ac) (53 ml) at reflux temperature. The reaction mixture was heated at reflux temperature for additional 16 hours. Then the reaction mixture was cooled to room temperature. Further cooling was performed using an ice-bath. The precipitate was then filtered, washed with Methanol (2×15 ml) and dried in a vacuum oven at 50° C. for 24 hours to give 4.85 g (90%) of Zoledronate disodium crystal form XXVII (LOD by TGA=7.5%).

Crystal Forms of Zoledronate Trisodium (ZLD-Na$_3$)

Preparation of ZLD-Na$_3$ Crystal Form IX

Example 65

A solution of sodium hydroxide (1.4 g) in a mixture of water (20% v/v)/Ethanol or Methanol or IPA (80% v/v, 10 volumes per grams of ZLD-Ac form XII) (10 ml) was added drop-wise to a suspension of Zoledronic acid form XII (5.0 g) in a mixture of water (20% v/v)/Ethanol or Methanol or IPA (80% v/v, 10 volumes per grams of ZLD-Ac) (53 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate trisodium crystal form IX.

| Sample No. | X % H$_2$O | Y % EtOH or MeOH or IPA | Total volume of solution (H$_2$O/EtOH or MeOH or IPA) | Yield (g/%) | LOD by TGA |
|---|---|---|---|---|---|
| 1 | 20% (13 ml) | 80% EtOH (50 ml) | 63 ml | 5.6 g/84% | 13.6% |
| 2 | 20% (13 ml) | 80% MeOH (50 ml) | 63 ml | 5.9 g/88% | 13.7% |
| 3 | 20% (13 ml) | 80% IPA (50 ml) | 63 ml | 5.6 g/85% | 13.5% |

Example 66

A solution of sodium hydroxide (1.4 g) in a mixture of water (40% v/v)/Ethanol or Methanol or IPA (60% v/v, 10 volumes per grams of ZLD-Ac form XII) (13 ml) was added drop-wise to a suspension of Zoledronic acid form XII (5.0 g) in a mixture of water (40% v/v)/Ethanol or Methanol or IPA (60% v/v, 10 volumes per grams of ZLD-Ac) (71 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate trisodium crystal form IX.

| Sample No. | X % H$_2$O | Y % EtOH or MeOH or IPA | Total volume of solution (H$_2$O/EtOH or MeOH or IPA) | Yield (g/%) | LOD by TGA |
|---|---|---|---|---|---|
| 1 | 40% (33 ml) | 60% EtOH (50 ml) | 83 ml | 5.7 g/68% | 13.9% |
| 2 | 20% (33 ml) | 60% MeOH (50 ml) | 83 ml | 5.5 g | — |
| 3 | 20% (33 ml) | 60% IPA (50 ml) | 83 ml | 5.7 g/85% | 14.3% |

Example 67

A solution of sodium hydroxide (1.4 g) in a mixture of water (50% v/v)/Ethanol or Methanol or IPA (50% v/v, 10 volumes per grams of ZLD-Ac form XII) (15 ml) was added drop-wise to a suspension of Zoledronic acid form XII (5.0 g) in a mixture of water (50% v/v)/Ethanol or Methanol or IPA (50% v/v, 10 volumes per grams of ZLD-Ac) (85 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate trisodium crystal form IX.

| Sample No. | X % H$_2$O | Y % EtOH or MeOH or IPA | Total volume of solution (H$_2$O/EtOH or MeOH or IPA) | Yield (g/%) | LOD by TGA |
|---|---|---|---|---|---|
| 1 | 50% (50 ml) | 50% EtOH (50 ml) | 100 ml | 5.5 g/84% | 11.6% |
| 2 | 50% (50 ml) | 50% MeOH (50 ml) | 100 ml | 5.2 g/77% | 14.6% |
| 3 | 50% (50 ml) | 50% IPA (50 ml) | 100 ml | 5.3 g/85% | 8.6% |

Example 68

A solution of sodium hydroxide (1.4 g) in a mixture of water (60% v/v)/Ethanol or Methanol or IPA (40% v/v, 10 volumes per grams of ZLD-Ac form XII) (19 ml) was added drop-wise to a suspension of Zoledronic acid form XII (5.0 g) in a mixture of water (60% v/v)/Ethanol or Methanol or IPA (40% v/v, 10 volumes per grams of ZLD-Ac) (106 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate trisodium crystal form IX.

| Sample No. | X % H$_2$O | Y % EtOH or MeOH or IPA | Total volume of solution (H$_2$O/EtOH or MeOH or IPA) | Yield (g/%) | LOD by TGA |
|---|---|---|---|---|---|
| 1 | 60% (75 ml) | 40% EtOH (50 ml) | 125 ml | 5.1 g/58% | 16.8% |
| 2 | 60% (75 ml) | 40% MeOH (50 ml) | 125 ml | 4.1 g/64% | 11.8% |

-continued

| Sample No. | X % $H_2O$ | Y % EtOH or MeOH or IPA | Total volume of solution ($H_2O$/EtOH or MeOH or IPA) | Yield (g/%) | LOD by TGA |
|---|---|---|---|---|---|
| 3 | 60% (75 ml) | 40% IPA (50 ml) | 125 ml | 5.3 g/79% | 14.1% |

Example 69

A solution of sodium hydroxide (1.4 g) in a mixture of water (80% v/v)/Ethanol or Methanol or IPA (20% v/v, 10 volumes per grams of ZLD-Ac form XII) (38 ml) was added drop-wise to a suspension of Zoledronic acid form XII (5.0 g) in a mixture of water (80% v/v)/Ethanol or Methanol or IPA (20% v/v, 10 volumes per grams of ZLD-Ac) (212 ml) at reflux temperature. The reaction mixture was heated at reflux temperature for additional 16 hours. Then the reaction mixture was cooled to room temperature. Further cooling was performed using an ice-bath. The precipitate was then filtered, washed and dried in a vacuum oven at 50° C. for 24 hours to give Zoledronate trisodium crystal form IX.

| Sample No. | X % $H_2O$ | Y % EtOH or MeOH or IPA | Total volume of solution ($H_2O$/EtOH or MeOH or IPA) | Yield (g/%) | LOD by TGA |
|---|---|---|---|---|---|
| 1 | 80% (200 ml) | 20% EtOH (50 ml) | 250 ml | 5.7 g/84% | 15.1% |
| 2 | 80% (200 ml) | 20% MeOH (50 ml) | 250 ml | 5.6 g/86% | 12.4% |
| 3 | 80% (200 ml) | 20% IPA (50 ml) | 250 ml | 5.6 g/83% | 14.5% |

Preparation of ZLD-Na$_3$ Crystal Form XI

Example 70

A 250 ml flask was loaded with Zoledronic acid form XII (5.0 g), Sodium hydroxide (1.4 g), absolute Ethanol (50 ml) and water (2.5 ml) [=5% v/v water in Ethanol]. The reaction mixture was heated to reflux temperature for 20 hours. Then the reaction mixture was cooled to room temperature. Further cooling was performed using an ice-bath. The precipitate was then filtered, washed with absolute Ethanol (2×25 ml) and dried in a vacuum oven at 50° C. for 24 hours to give 5.4 g (86%) of Zoledronate trisodium crystal form XI (LOD by TGA=8.9%).

Example 71

A 250 ml flask was loaded with Zoledronic acid form XII (5.0 g), Sodium hydroxide (1.4 g), Methanol (50 ml) and water (2.5 ml) [=5% v/v water in Methanol]. The reaction mixture was heated to reflux temperature for 22 hours. Then the reaction mixture was cooled to room temperature. Further cooling was performed using an ice-bath. The precipitate was then filtered, washed with Methanol (2×50 ml) and dried in a vacuum oven at 50° C. for 24 hours to give 5.4 g (84%) of Zoledronate trisodium crystal form XI in a mixture with crystal form IX (LOD by TGA=10.5%).

General Procedure for the Preparation of Amorphous Zoledronate Sodium

Example 72

A 100 ml flask was loaded with Zoledronic acid crystal form XII (2.0 g), Sodium hydroxide (0.57 g) and water (10 ml). The reaction mixture was stirred at room temperature to obtain a clear solution. Then the solution was concentrated under vacuum to obtain a precipitate. Further cooling was performed using an ice-bath. The precipitate was then filtered, washed with water (2×10 ml) and dried in a vacuum oven at 50° C. for 24 hours to give 0.76 g of amorphous Zoledronate sodium.

Summarizing Tables—Crystals Forms of Zoledronate Sodium Salts

1. Preparation of Zoledronate monosodium salt:

| | EtOH | MeOH | IPA |
|---|---|---|---|
| 0% v/v $H_2O$ | I (ZLD-Ac) + XV(ZLD-Ac) | XV(ZLD-Ac) | No reaction |
| 20% v/v $H_2O$ | | XII(ZLD-Ac) > IV | |
| 50% v/v $H_2O$ | XVI | No reaction | XVI |
| 80% v/v $H_2O$ | VIII >> XII(ZLD-Ac) | VIII | VIII |

Using ZLD-Ac (assay 100%, Form I) as a starting material

2. Preparation of Zoledronate disodium salt:

| | EtOH | MeOH | IPA |
|---|---|---|---|
| 5% v/v $H_2O$ | XIII | XXVII | No reaction |
| 20% v/v $H_2O$ | V | XIV | V |
| 50% v/v $H_2O$ | V > VI + IX | V >> IX? | V |
| 80% v/v $H_2O$ | VII | XXV | VI |

Using ZLD-Ac (assay 100%, Form I) as a starting material

| | EtOH | MeOH | IPA | DMF |
|---|---|---|---|---|
| 20% v/v $H_2O$ | V | V + XXVII | X | XIV |
| 40% v/v $H_2O$ | V | V > XII | V | = |
| 50% v/v $H_2O$ | V | V > VIII | V > VIII | = |
| 60% v/v $H_2O$ | VI | VI + 11.3 | VIII (crop I) VII + 8.2 (crop II) | = |
| 80% v/v $H_2O$ | VII | VII | VII + 8.2, 9.1 | — |
| 100% v/v $H_2O$ | | | Amorphous | |

Using ZLD-Ac (assay 90%, Form XII) as a starting material

3. Preparation of Zoledronate trisodium salt:

| | EtOH | MeOH | IPA |
|---|---|---|---|
| 5% v/v $H_2O$ | XI | IX + XI | — |
| 20% v/v $H_2O$ | IX + IV | IX > IV + 9.9 | IX + 6.4, 6.7 |
| 40% v/v $H_2O$ | IX | IX + V | IX + IV |
| 50% v/v $H_2O$ | IX + IV | IX + V >> IV | IX + IV + amorph. + 7.1 |
| 60% v/v $H_2O$ | IX + IV | IX > IV | IX |
| 80% v/v $H_2O$ | IX | IX | IX |
| 100% v/v $H_2O$ | Amorphous | | |

Using ZLD-Ac (assay 90%, Form XII) as a starting material

What is claimed:

1. Crystalline solid zoledronic acid (Form XII) characterized by a powder X-ray pattern having peaks at 9.0°, 13.9°, 14.8°, 21.5°, 24.7°, and 29.8° 2θ±0.2° 2θ.

2. The crystalline zoledronic acid of claim 1, further characterized by a powder X-ray diffraction pattern with peaks at 17.0°, 20.6°, 20.8°, 22.4°, 25.8°, 27.7°, 28.4°, 28.7°, 29.1°, 30.8°, 31.9°, 32.3°, and 32.9° 2θ±0.2° 2θ.

* * * * *